US008106007B2

(12) United States Patent
Bos et al.

(10) Patent No.: US 8,106,007 B2
(45) Date of Patent: Jan. 31, 2012

(54) CONJUGATES OF A POLYPEPTIDE AND A PENTASACCHARIDE

(75) Inventors: Ebo Sijbren Bos, Oss (NL); Martin De Kort, Oss (NL); Meertinus Jan Smit, Oss (NL); Constant Adriaan Anton Van Boeckel, Oss (NL)

(73) Assignee: N.V. Organon, Oss (NL)

( * ) Notice: Subject to any disclaimer, the term of this patent is extended or adjusted under 35 U.S.C. 154(b) by 966 days.

(21) Appl. No.: 11/815,131

(22) PCT Filed: Jan. 31, 2006

(86) PCT No.: PCT/EP2006/050551
§ 371 (c)(1),
(2), (4) Date: Jan. 25, 2008

(87) PCT Pub. No.: WO2006/082184
PCT Pub. Date: Aug. 10, 2006

(65) Prior Publication Data
US 2008/0139459 A1 Jun. 12, 2008

(30) Foreign Application Priority Data
Feb. 1, 2005 (EP) .................................. 05100688

(51) Int. Cl.
A61K 38/28 (2006.01)
A61K 31/70 (2006.01)
C07K 14/62 (2006.01)
A01N 43/04 (2006.01)
C07G 3/00 (2006.01)
C07G 11/00 (2006.01)
C07H 15/00 (2006.01)
C07H 17/00 (2006.01)
C07H 1/00 (2006.01)

(52) U.S. Cl. .............. 514/5.9; 514/25; 514/56; 536/4.1; 536/123.1

(58) Field of Classification Search .................... 514/5.9, 514/25, 56; 536/4.1, 123.1
See application file for complete search history.

(56) References Cited

U.S. PATENT DOCUMENTS

| 4,179,337 | A | 12/1979 | Davis et al. | |
| 4,431,740 | A | 2/1984 | Bell et al. | |
| 4,652,525 | A | 3/1987 | Rutter et al. | |
| 5,206,344 | A | 4/1993 | Katre et al. | |
| 5,268,453 | A | 12/1993 | Andy et al. | |
| 5,506,202 | A | 4/1996 | Vertesy et al. | |
| 5,514,646 | A | 5/1996 | Chance et al. | |
| 5,700,662 | A | 12/1997 | Chance et al. | |
| 6,486,129 | B1 * | 11/2002 | Tromp et al. | 514/32 |
| 6,514,500 | B1 | 2/2003 | Bridon et al. | |
| 6,534,481 | B1 | 3/2003 | Driguez | |
| 6,670,338 | B1 | 12/2003 | Petitou | |
| 2004/0024197 | A1 | 2/2004 | Duchaussoy et al. | |
| 2005/0152848 | A1 | 7/2005 | Patton et al. | |

FOREIGN PATENT DOCUMENTS

| EP | 0454220 | 10/1991 |
| EP | 0529715 | 3/1993 |
| JP | 02/231077 | 9/1990 |
| WO | WO92/22331 | 12/1992 |
| WO | WO98/02460 | 1/1998 |
| WO | WO98/03554 | 1/1998 |
| WO | WO98/08871 | 3/1998 |
| WO | WO99/36428 | 7/1999 |
| WO | WO99/46283 | 9/1999 |
| WO | WO00/24893 | 5/2000 |
| WO | WO00/40253 | 7/2000 |
| WO | WO00/69911 | 11/2000 |
| WO | WO01/42262 | 6/2001 |
| WO | WO01/87922 | 11/2001 |
| WO | WO02/098232 | 12/2002 |
| WO | WO03/013573 | 2/2003 |
| WO | WO2004/022577 | 3/2004 |
| WO | WO2004/032971 | 4/2004 |
| WO | WO2004/060404 | 7/2004 |
| WO | WO2004/091494 | 10/2004 |
| WO | WO2004/093823 | 11/2004 |
| WO | WO2005/012346 | 2/2005 |
| WO | WO2005/058954 | 6/2005 |

OTHER PUBLICATIONS

Chan, A., Berry, L., O'Brodovich, H., Klement, P., Mitchell, L., Baranowski, B., Monagle, P., Andrew, M. (1997) Covalent Antithrombin-Heparin Complexes with High Anticoagulant Activity. The Journal of Biological Activity, vol. 272, No. 35, p. 22111-22117.*

Zhang, F., Ronca, F., Linhardt, R.J., Margolis, R.U. (2004) Structural determinants of heparan sulfate interactions with Slit proteins. Biochemical and Biophysical Research Communications, vol. 317, p. 352-357.*

Buijsman, R.C., Basten, J.E.M., Dreef-Tromp, C.M., van der Marel, G.A., van Boeckel, C.A.A., van Boom, J.H. (1999) Synthesis of Heparin-Like Antithrombotics Having perphosphorylated Thrombin Binding Domains. Bioorganic & Medicinal Chemistry, vol. 7, p. 1881-1890.*

Hermanson, G.T. (1996) "Heterobifunctional Cross-linkers" in Bioconjugate Techniques, p. 228-248, Published by Academic Press, Elsevier.*

Dennis, M.S., Henzel, W.J., Pitti, R.M., Lipari, M.T., Napier, M.A., Deisher, T.A., bunting, S., Lazarus, R.A. (1989) Platelet glycoprotein IIb-IIIa protein antagonists from snake venoms: Evidence for a family of platelet-aggregation inhibitors. Proceedings of the National Academy of Sciences, vol. 87, p. 2471-2475.*

(Continued)

Primary Examiner — Shaojia Anna Jiang
Assistant Examiner — Scarlett Goon
(74) Attorney, Agent, or Firm — John David Reilly; Immac J. Thampoe

(57) ABSTRACT

The present invention relates to conjugates of a polypeptide and an oligosaccharide, wherein the polypeptide is conjugated to at least one oligosaccharide-spacer residue, the oligosaccharide being a synthetic sulfated oligosaccharide comprising 4-18 monosaccharide units and per se having affinity to antithrombin III and the spacer being a bond or an essentially pharmacologically inactive flexible linking residue, or a pharmaceutically acceptable salt thereof. The conjugates of the invention have improved pharmacokinetic properties when compared to the original polypeptides (i.e. the corresponding non-conjugated polypeptides per se).

13 Claims, 22 Drawing Sheets

OTHER PUBLICATIONS

Figure 1:
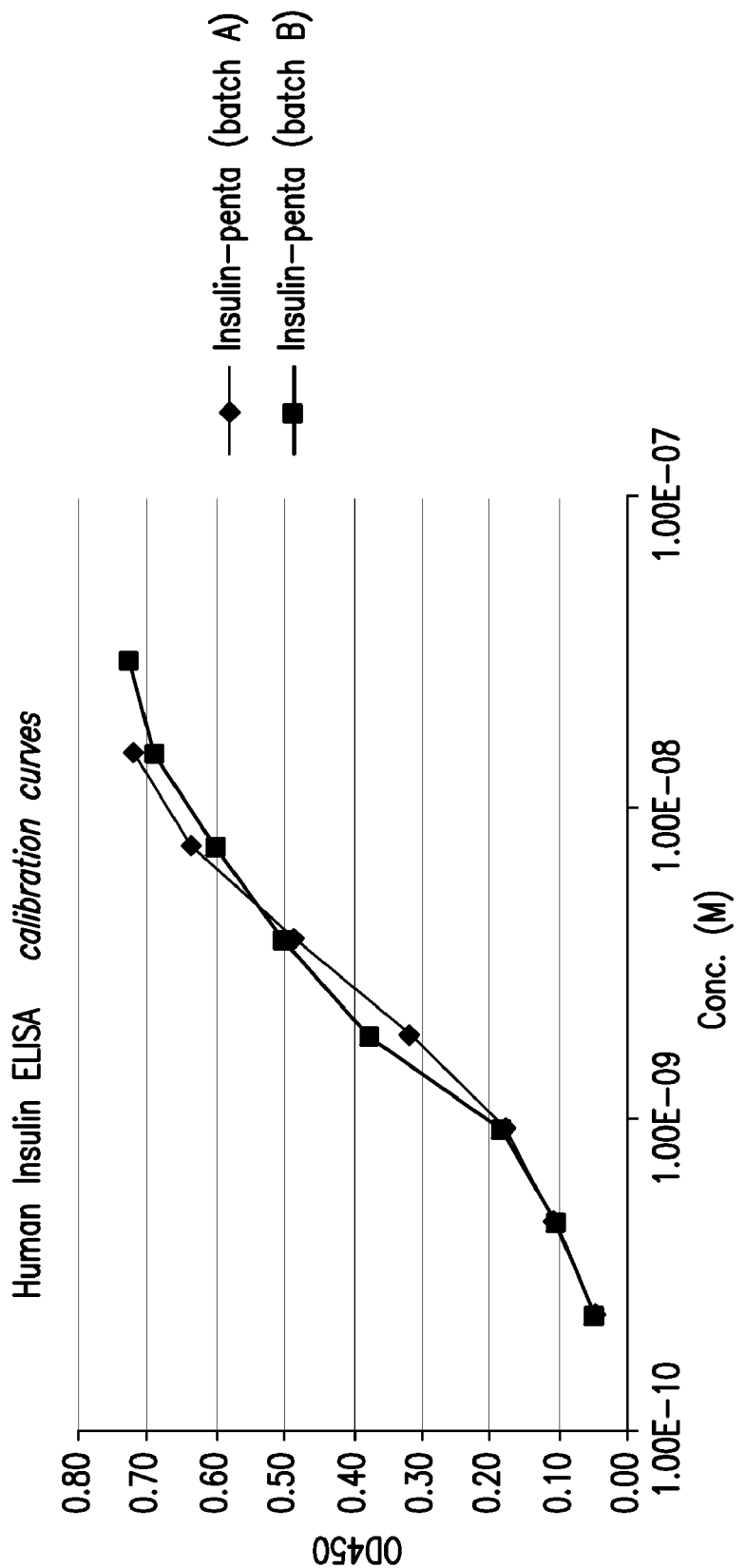

International Search reported for PCT/EP2006/050551 dated Mar. 30, 2007.
English-language abstracts of JP 02/231077 (JP 1990/230177).
Database WPI, Section Ch, Week 200454, Derwent Publications Ltd., London, GB & WO2004/060404 Abstract.
"2001 Guidelines for Authors," *J. Org. Chem.* 66 (2001) 18A-24A.
Alban, S., "The precautionary principle and its impact on medicine," *Krankenhauspharmazie* 24 (2003) 367-373.
Amsterdam et al., "Synthetic analogues of the antithrombin III-binding pentasaccharide sequence of heparin prediction of in vivo residence times," *Arteriosclerosis, Thrombosis and Vascular Biology* 15 (1995) 495-503.
Arnarp et al., "Synthesis of oligosaccharides that form parts of the complex type of carbohydrate moieties of glycoproteins. Three glycosides prepared for conjugation to proteins," *Acta Chemica Scandinavica. Series B: Organic Chemistry and Biochemistry* 37 (1983) 329-334.
Baudys et al., "Extending insulin action in vivo by conjugation to carboxymethyl dextran", *Bioconjugate Chemistry* 9 (1998) 176-183.
Buijsman et al., "Design and synthesis of a novel synthetic NAPAP-penta-saccharide conjugate displaying a dual antithrombotic action," *Bioorganic & Medicinal Chemistry Letters* 9, (1999) 2013-2018.
Buijsman et al., "Synthesis of a pentasaccharide-oligodeoxyribonucleotide conjugate: a novel antithrombotic agent," *Chemistry—A European Journal* 2 (1996) 1572-1577.
Cai et al., "Adrenomedullin$_{(27-52)}$ inhibits vascular calcification in rats," *Regulatory Peptides* 129 (2005) 125-132.
Chan, et al., "Disposition of RS-26306, A Potent Luteinizing Hormone-Releasing Hormone Antagonist, in Monkeys and Rats After Single Intravenous and Subcutaneous Administration," *Drug. Metab. Dispos* 19 (1991) 858-864.
Cornish et al., "Adrenomedullin—a regulator of bone formation," *Regulatory Peptides* 112 (2003) 79-86.
Donat et al., "The Pharmacokinetics of Fondaparinux Sodium in Healthy Volunteers," *Clin. Pharmacokinet 41 Suppl. 2* (2002) 1-9.
Duttaroy et al., "Development of a Long-Acting Insulin Analog Using Albumin Fusion Technology," *Diabetes* 54 (2005) 251-258.
Ekwall et al., "Identification of salmonellae of serogroup C-1 by immuno fluorescence and co agglutination with anti serum against and oligo saccharide protein conjugate," *Journal of Medical Microbiology* 15 (1982) 173-180.
Gillis et al., "T Cell Growth Factor: Parameters of Production and a Quantitative Microassay for Activity," *J. Immunol.* 120 (1978) 2027-2032.
Hård et al., "O-Mannosylation of recombinant human insulin-like growth factor I (IGF-I) produced in *Saccharomyces cerevisiae*," *FEBS Letters* 248 (1989) 111-114.
Hee et al., "PEGylation of Octreotide: II. Effect of N-terminal Mono-PEGylation on Biological Activity and Pharmacokinetics," *Pharm. Res.* 22 (2005) 743-749.
Hinds et al., "Effects of PEG conjugation on insulin properties," *Adv. Drug Del. Rev.* 54 (2002) 505-530.
Hoeg-Jensen et al., "Insulins with built-in glucose sensors for glucose responsive insulin release," *J. Pept. Sci.* 11 (2005) 339-346.
Jain et al., "Polysialylated insulin: synthesis, characterization and biological activity in vivo," *Biochim. Biophys. Act.* 1622 (2003) 42-49.
Jones, J.H., ed., "A Short Guide to Abbreviations and Their Use in Polypeptide Science", *J. Polypeptide. Sci* 5 (1999) 465-471.
Keam et al., "Fondaparinux Sodium," *Drugs* 62 (2002) 1673-1685.
Kiick et al., "Incorporation of azides into recombinant proteins for chemoselective modification by the Staudinger ligation," *Proc. Nat. Acad. Sci.* 99 (2002) 19-24.
Kim et al., "Synthesis, bioactivity and specificity of glucagon-I ike peptide-1 (7-37)/polymer conjugate to isolated rat islets," *Biomaterials* 26 (2005) 3597-3606.
Kudryashov et al., "Immunogenicity of synthetic conjugates of Lewisy oligosaccharide with proteins in mice: Towards the design of anticancer vaccines," *Cancer Immunology Immunotherapy* 45 (1998) 281-286.

Lahmann et al., "Synthesis of a polyphosphorylated GPI-anchor core structure," *Canadian Journal of Chemistry* 80 (2002) 1105-1111.
Lee et al., "Preparation and Characterization of Polyethylene-Glycol-Modified Salmon Calcitonins," *Pharm. Dev. Technol.* 4 (1999) 269-275.
Lee et al., "Synthesis and Biological Properties of Insulin-Deoxycholic Acid Chemical Conjugates," *Bioconj. Chem.* 16 (2005) 615-620.
Lee et al., "Synthesis, Characterization, and Pharmacokinetic Studies of PEGylated Glucagon-like Peptide-1," *Bioconj. Chem.* 16 (2005) 377-382.
Léger et al., "Identification of CJC-1131-albumin bioconjugate as a stable and bioactive GLP-1(7-36) analog," *Bioorg. Med. Chem. Lett.* 14 (2004) 4395-4398.
Lewinska et al., "A Novel Method for the N-Terminal Modification of Native Proteins," *Bioconjugate Chem.* 15 (2004) 231-234.
Lindahl et al., "Generation of "Neoheparin" from *E. coli* K5 Capsular Polysaccharide," *J. Med. Chem* 48 (2005) 349-352.
Machalonis, J.J., "An Enzymic Method for the Trace Iodination of Immunoglobulins and other Proteins," *Biochem J.* 113 (1969) 299-305.
Meeran et al., "Circulating Adrenomedullin Does Not Regulate Systemic Blood Pressure but Increases Plasma Prolactin after Intravenous Infusion in Humans: A Pharmacokinetic Study," *J. Clin. Endocrin. Met.* 82 (1997) 95-100.
Meurer et al., "Properties of native and in vitro glycosylated forms of the glucagon-like peptide-1 receptor antagonist exendin (9-39)," *Metabolism, Clinical and Experimental* 48 (1999) 716-724.
Nestor et al., "Potent Gonadotropin Releasing Hormone Antagonists with Low Histamine-Releasing Activity," *J. Med. Chem.* 35 (1992) 3942-3948.
Nilsson et al., "Synthesis of the saccharide moiety of galactosylgloboside (SSEA-3) and its conjugation to bovine serum albumin and Sepharose," *Carbohydrate Research* 272 (1995) 9-16.
Paolucci et al., "Fondaparinux Sodium Mechanism of Action," *Clin. Pharmacokinet 41 Suppl. 2* (2002) 11-18.
Petitou et al., "A synthetic antithrombin III binding pentasaccharide is now a drug What comes next?" *Angewandte Chemie* 43 (2004) 3118-3133.
Sabbatini et al., "Immunization of ovarian cancer patients with a synthetic Lewisy-protein conjugate vaccine: A phase 1 trial," *International Journal of Cancer* 87 (2000) 79-85.
Salhanick et al., "Contribution of site-specific PEGylation to the dipeptidyl peptidase IV stability of glucose-dependent insulinotropic polypeptide," *Bioorg. Med. Chem. Lett.* 15 (2005) 4114-4117.
Sato et al., "Glycoinsulins: Dendritic Sialyloligosaccharide-Displaying Insulins Showing a Prolonged Blood-Sugar-Lowering Activity," *J. Am. Chem. Soc.* 126 (2004) 14013-14022.
Szymkowski et al., "Creating the next generation of protein therapeutics through rational drug design," *Curr. Opin. Drug Disc. Dev.* 8 (2005) 590-600.
Tessmar et al., "Toward the Development of Biomimetic Polymers by Protein Immobilization: PEGylation of Insulin a as a Model Reaction," *Tissue Engin.* 10 (2004) 441-453.
The Rembrandt Investigators, "Treatment of Proximal Deep Vein Thrombosis With a Novel Synthetic Compound (SR90107A/ORG31540) With Pure Anti-Factor Xa Activity," *Circulation* 102 (2000) 2726-2731.
Uchio et al., "Site-specific insulin conjugates with enhanced stability and extended action profile," *Advanced Drug Delivery Reviews* 35 (1999) 289-306.
van Boeckel et al., "The Unique Antithrombin III Binding Domain of Heparin: A Lead to New Synthetic Antithrombotics," *Angew. Chem. Intl. Ed. Engl.* 32 (1993) 1671-1690.
Veronese et al., "PEGylation, successful approach to drug delivery," *Drug Discovery Today* 10 (2005) 1451-1458.
Vogel et al., "Antithrombotic properties of a direct thrombin inhibitor with a prolonged half life and at-mediated factor XA inhibitory activity," *Journal of Thrombosis and Haemostasis 1* (2003) 1945-1954.

Walenga et al., "Antithrombotic activity of a synthetic heparin pentasaccharide in arabbit stasis thrombosis model using different thrombogenic challenges," *Thrombosis Research 46* (1987) 187-198.

Westerduin et al., "Feasible Synthesis and Biological Properties of Six 'Non-Glycosamino' Glycan Analogues of the Antithrombin III Binding Heparin Pentasaccharide," *Bioorg. Med. Chem. 2* (1994) 1267-1280.

Westerduin et al., "Synthesis of tailor-made glycoconjugates showing ATIII-metidated inhibition of blood coagulation factors Xa and Thrombin," *Angewandte Chemie 35* (1996) 331-333.

Zou et al., "Synthesis and NMR assignments of galactosylgloboside and its beta-D-GalNAc-(1 fwdarw 4)-alpha-D-Gal-linked positional isomer in a conjugatable form," *Carbohydrate Research 315* (1999) 251-261.

* cited by examiner

CONJUGATES OF A POLYPEPTIDE AND A PENTASACCHARIDE

CROSS REFERENCE TO RELATED APPLICATION

This application claims priority based on International Patent Application No. PCT/EP2006/050551, filed on Jan. 31, 2006, which claims benefit of EP Application No. 05100688.0 filed Feb. 1, 2005.

FIELD OF THE INVENTION

The present invention relates to new conjugates of polypeptides and oligosaccharides, a process for their preparation, pharmaceutical compositions containing the compounds as active ingredients, as well as the use of said compounds for the manufacture of medicaments.

BACKGROUND OF THE INVENTION

Recent developments of recombinant DNA techniques and advanced peptide synthetic methods have permitted the commercial production of medically useful quantities of therapeutic polypeptides. The short half-life of many therapeutic polypeptides, however, has historically posed a challenge to the administration of these compounds. There are several important polypeptide-based drugs currently in use which would benefit from increased half-life. Examples are erythropoietin, insulin, interferon α-2b, interferon β, interferon γ, granulocyte colony stimulating factor, human growth hormone, granulocyte macrophage colony stimulating factor, relaxin, urokinase, streptokinase, tissue plasminogen activator, calcitonin, interleukin-2 and tumor necrosis factor with half-lives (significantly) less than a few hours. Insulin, for example, has a half-life of only about 12 minutes in man. Other examples of polypeptides that are being developed as potential therapeutic agents but suffer from short half-lives are adrenomedullin, glucagon like peptide (GLP-1) and kisspeptin (metastin). Extending the half-life of therapeutic polypeptides can improve current treatment by allowing dosing amounts and frequency of dosing to be reduced (*Curr. Opin. Drug Disc. Dev.* 2005, 8, 590-600).

Many proteins have already been subjected to studies aimed at extending the in vivo half-life employing e.g. adaptation by PEGylation (i.e. conjugation with a ~1-30 kDa polyethylene glycol-moiety; *Drug Discovery Today* 2005, 10, 1451-1458). Currently available are for example PEGylated analogs of insulin with an extended half-life. Beside the reduced clearance rate, important aspects of the latter insulin derivatives are the reduced immunogenicity (e.g. U.S. Pat. No. 4,179,337) and increased solubility. Further, developments in PEGylation of insulin also led to physically and proteolytically more stable conjugates than native insulin (see for example WO 2004/091494, WO 2002/098232, US 2005/0152848).

PEGylated erythropoietin with a longer serum half-life is for example described in WO 2004/022577. It has further been found that by altered glycosylation of erythropoietin, the half-life increases. In addition, hyperglycosylated analogs of erythropoietin were reported to have higher in vivo activity (WO 2000/24893). Other examples of PEGylated (poly)peptides with prolonged duration of action are glucagon-like peptide-1 (GLP-1) (WO 2005/058954, WO 2004/093823; *Bioconjugate Chem.* 2005, 16, 377-382; *Biomaterials*, 2005, 26, 3597-3606), glucose-dependent insulinotropic polypeptide (GIP) (*Bioorg. Med. Chem. Lett.*, 2005, 15, 4114-4117), calcitonin (*Pharm. Dev. Technol.* 1999, 4, 269-275) and octreotide (*Pharm. Res.* 2005, 22, 743-749).

Still, the use of PEG has limitations. PEG is obtained by chemical synthesis and, like all synthetic polymers, is polydisperse. This means that a batch of PEG consists of molecules having different numbers of monomers, resulting in a Gaussian distribution of the molecular weights. When a polypeptide is PEGylated, this leads to a collection of conjugates, which may have different biological properties, in particular in half-lives and immunogenicity. Reproducibility of the pharmacological activities of PEGylated polypeptides may therefore be a serious drawback of the technique. Also, it is known that PEGylation of proteins is often accompanied by loss of biological activity. Further, the use of PEG may cause problems relating to excretion from the body. At high molecular weights PEGs can accumulate in the liver, leading to macromolecular syndrome. Consequently, PEGylation of drugs should be performed with great care.

Similar results as with PEGylation were obtained by derivatization of polypeptides with polysaccharides, in particular with polysialic acid chains (e.g. WO 92/22331 and WO 2001/87922).

In JP 02/231077, heparin-superoxide dismutase (SOD) conjugates are described. Preferably, a number of heparin molecules are attached to SOD resulting in conjugates having a longer half-life than native SOD while retaining about 90% of the enzymatic activity.

Other conjugates of polypeptides with increased half-life are exemplified by conjugated derivatives of insulin (WO 2003/013573, WO 05/012346) or GLP-1 (*Bioorg. Med. Chem. Lett.* 2004, 14, 4395-4398) which bind to circulating serum albumin. The binding to serum albumin in those compounds is based in particular on hydrophobic interactions of the binding moiety within the conjugate with human serum albumin. The higher the hydrophobicity of that moiety, the stronger the binding affinity to human serum albumin. Although a wide range of binding moieties is suitable, a drawback of such conjugates is the low affinity and selectivity of the interaction of the conjugates with human serum albumin with as a result a poor predictability of the pharmacodynamic behavior. Alternatively, fusing the gene for human insulin directly to that for human serum albumin results in a long-acting form of insulin that is active in reducing blood glucose levels for a prolonged period after subcutaneous administration (Duttaroy et al. *Diabetes* 2005, 54, 251-258). However, in this case the bioavailability of the fused polypeptide, as well as the binding affinity for the target receptor, is reduced.

Further, in WO 2000/40253 conjugates of, for instance, a peptide and, specifically, glycosaminoglycan chain(s) are disclosed, which are considered as synthetic proteoglycans. In those conjugates the pharmacological activity of the conjugated glycosaminoglycan has a significant impact on the therapeutic activity of the conjugates.

Also, oligosaccharides are attached to pharmaceutically active compounds in order to increase the solubility thereof (WO 2004/03971).

DETAILED DESCRIPTION OF THE INVENTION

The present invention relates to new conjugates of polypeptides with increased half-lives, being conjugates of a polypeptide and an oligosaccharide, wherein the polypeptide is conjugated to at least one synthetic sulfated oligosaccharide-spacer residue, the oligosaccharide comprising 4-18 monosaccharide units and per se having affinity to antithrombin III and the spacer being a bond or an essentially pharmacologically inactive flexible linking residue, or a pharmaceutically acceptable salt thereof. Preferred oligosaccharides consist of 4-6 monosaccharide units and in particular preferred are pentasaccharides. The conjugates of the invention have improved pharmacokinetic properties—and thus improved pharmacological properties—when compared to the original polypeptides (i.e. the corresponding non-conjugated polypeptides per se).

The present invention further relates to a novel technology based on a process for the preparation of a therapeutically active conjugate comprising a polypeptide and having negligible anti-thrombotic activity, comprising a step wherein a synthetic sulfated oligosaccharide, in particular a pentasaccharide, which per se has affinity to antithrombin III (ATIII), is covalently attached to a polypeptide through a bond or an essentially pharmacologically inactive flexible linking residue.

ATIII is a serine protease inhibitor, present in blood plasma, which interrupts the coagulation cascade to provide a feed back loop. The half-life of a sulfated pentasaccharide is essentially based on its affinity to ATIII (see e.g. F. Paolucci et al. *Clin. Pharmacokinet.* 2002; 41 Suppl. 2: 11-18). In the conjugates of this invention the serum half-life is longer than the half-life of the original polypeptide as a result of the half-life of the pentasaccharide which largely accounts for the half-life of the conjugate. Furthermore, the conjugates of the invention not only have a longer half-life, but they also have tunable pharmacokinetic properties based on the specific interaction between the pentasaccharide part of the conjugate and ATIII (the latter interaction is described e.g. in Westerduin et. al. *Bioorg. Med. Chem.* 1994, 1267-1280; van Amsterdam et al., *Arterioscler Thromb Vasc Biol.* 1995; 15:495-503). In an embodiment of the present invention the oligosaccharide-polypeptide conjugate (the oligosaccharide in particular consisting of 4-6 monosaccharide units and most particularly being a pentasaccharide) has a circulating plasma level of ≦50 nM. Up to this concentration the ATIII-mediated anticoagulant activity of the oligosaccharide (in particular pentasaccharide) is insignificant in particular with respect to bleeding risks. (see for instance (1) F. Donat et al., *Clin. Pharmacokinet.* 2002; 41 Suppl. 2: 1-9; (2) S. J. Keam et al. *Drugs* 2002; 62 (11):1673-1685 and (3) The Rembrandt Investigators *Circulation* 2000; 102: 2726-2731). According to an embodiment of this invention, the oligosaccharide (in particular consisting of 4-6 monosaccharide units and most particularly being a pentasaccharide) used in the conjugates per se has an anticoagulant activity which is of subtherapeutic level when compared to the pharmacological activity of the polypeptide per se. Subtherapeutic in this respect means: having a lower than therapeutic effect and without side-effects, such as bleeding risks. For example, diabetes type 1 patients require (long half-life) insulin injections to complement (basal) therapeutic plasma levels of ~[0.1-1.0] nM, which is well in the subtherapeutic range of the pentasaccharides used in the present conjugates. A person skilled in the art will understand how to select conjugates with a proper balance between the therapeutic levels of the polypeptide and the pentasaccharide, respectively.

The polypeptides in the conjugates of the present invention retain their biological activity. Furthermore, the linear pharmacokinetic behavior of ATIII-bound pentasaccharide in the conjugates of this invention accounts for a highly predictable therapeutic effect of the conjugated polypeptides, since the conjugates remain largely in the intravascular compartment after i.v. or s.c. dosing.

The oligosaccharide residue in the conjugates of this invention is a residue from a synthetic sulfated oligosaccharide which per se has affinity to antithrombin III (ATIII). Sulfated oligosaccharides, and in particular pentasaccharides, generally have affinity to ATIII, however, a person skilled in the art can easily check the affinity of an oligosaccharide to ATIII (van Amsterdam et al., *Arterioscler Thromb Vasc Biol.* 1995; 15:495-503) and select the desired affinity level. Suitable synthetic oligosaccharide residues and in particular pentasaccharide residues may be derived from the oligo- and pentasaccharides disclosed in EP 0,454,220, EP 0,529,715, WO 98/03554, WO 99/36428, *J. Med. Chem.* 2005; 48, 349-352, *Angew. Chem. Intl. Ed. Engl.* 1994, 32, 1671-1690 and the like.

The oligo- and pentasaccharide residues may be conjugated to the polypeptide directly or via a linking residue attached to any chemically suitable position within the pentasaccharide residue. Therefore, in an embodiment of this invention the conjugates are conjugates wherein the oligosaccharide-spacer residue has the structure (I)

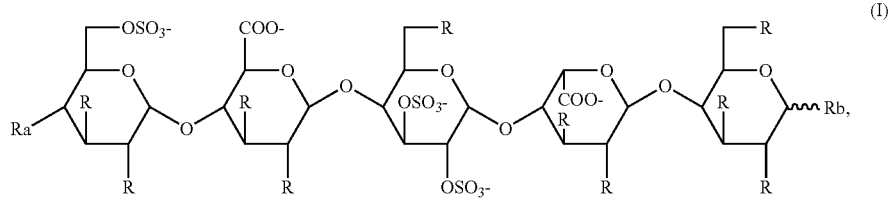

wherein one essentially pharmacologically inactive flexible linking residue is present and wherein
R is independently $OSO_3^-$, (1-8C)alkoxy or an essentially pharmacologically inactive flexible linking residue, and
Ra is independently $OSO_3^-$, (1-8C)alkoxy, an essentially pharmacologically inactive flexible linking residue or an oligosaccharide residue, comprising 1-13 monosaccharide units, and
Rb is independently (1-8C)alkoxy, an essentially pharmacologically inactive flexible linking residue or an oligosaccharide residue, comprising 1-13 monosaccharide units,
the charge being compensated by positively charged counterions.

More preferred are conjugates wherein the oligosaccharide-spacer residue is a pentasaccharide-spacer residue having the structure (II)

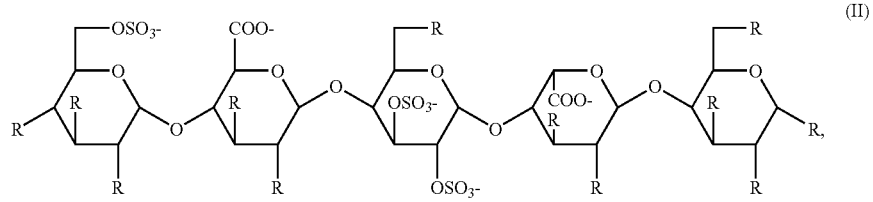

wherein one essentially pharmacologically inactive flexible linking residue is present and wherein R is independently $OSO_3^-$ or (1-8C)alkoxy, or an essentially pharmacologically inactive flexible linking residue, the charge being compensated by positively charged counter ions.

Further preferred are conjugates wherein the pentasaccharide residue has the structure (III)

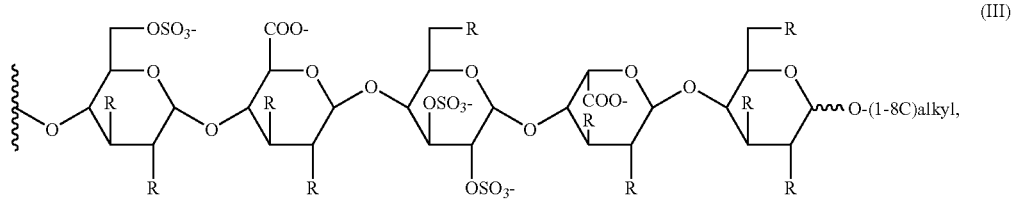

wherein R is independently $OSO_3^-$ or (1-8C)alkoxy, the charge being compensated by positively charged counterions.

Highly preferred compounds according to the invention are compounds wherein the pentasaccharide residue has the structure (IV)

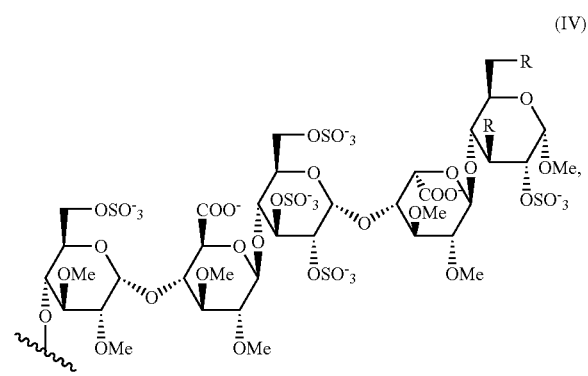

wherein R is independently $OCH_3$ or $OSO_3^-$, and in particular both R groups in (II) are $OSO_3^-$.

According to this invention, synthetic sulfated oligosaccharide residues, in particular pentasaccharide residues, with affinity to ATIII can be conjugated to any polypeptide. For example, the polypeptide can be a bioactive peptide (e.g., 3 to 50 amino acids in length) or can be a longer polypeptide that may or may not have catalytic activity. Non-limiting examples of bioactive peptides include neurotransmitters such as conantokin G, dynorphin, endorphin, enkephalin, or neurotensin; gastric activators such as bombesin, motilin, or gastrin; calcium regulators such as calcitonin or parathyroid hormone (PTH); bone resorption modulators such as osteoprotegerin (OPG); stimulators of osteoblastic activity such as adrenomedullin or truncated derivatives thereof such as ADM(27-52); hormones such as vasoactive intestinal polypeptide, corticotropin, secretin; hormone inhibitors such as somatostatin; hormone stimulators such as melanocyte stimulating hormone, luteinizing hormone releasing factor, or sermorelin; anti-diabetic agents such as glucagons, amylin, glucagon-like peptide-1 (GLP-1) or truncated derivatives thereof such as GLP-1(7-36), GLP-2, glucose-dependent insulinotropic polypeptide (GIP) or insulin ("Humulin," Eli Lilly); anti-infectives such as lysostaphin; appetite suppressing hormones such as obestatin; vasoconstrictors such as angiotensin II; vasodilators such as bradykinin, substance P or kallidin; natriuretic agents such as atrial natriuretic polypeptide (ANP); antidiuretic hormones such as vasopressin or desmopressin; and oxytocic agents such as oxytocin. Additional examples of polypeptides that can be used include human growth hormone ("Humantrope," Genentech); rLH; rG-CSF ("Neupogen," Amgen); erythropoietin ("Epogen," Amgen); interferon α-2a, interferon α-2b, interferon β, or interferon γ; factor VIII or other blood clotting factors such as protein C or factor VIIa; follicle stimulating hormone (FSH); a cytokine such as an interleukin (IL) (e.g., IL-1, -2, -3, -4, -5, -6, -7, -8, -9, -10, -11, -12, or -18); hemoglobin; superoxide dismutase; soluble CD4 or CD4 receptor; platelet GpIIb/IIIa analogs and their receptors ("ReoPro," Johnson & Johnson); glucocerebrosidase ("Ceredase" or "Cerezyme," Genzyme); ACTH; somatotropin; parathyroid hormone, antidiuretic hormone; prolactin; rHGH, such as pegvisomant ("Somavert", Pfizer); GnRH agonists, such as leuprolide ("Lupron", "Leprorelin", Takeda) or nafareline ("Synarel", Roche) and GnRH antagonists, such as ganirelix ("Antagon", Organon); GHRH agonists, such as sermorelin ("Geref", Serono); octreotide ("Sandostatin", Novartis); or thrombolytics such as streptokinase, staphylokinase, urokinase, or tissue plasminogen activator ("Activase," Genentech); metastin (KISS1 or kisspeptin-54) or truncated derivatives thereof such as kisspeptin-10.

Preferred polypeptides have a molecular weight of ~0.3-50 kDa. Other preferred polypeptides have a molecular weight of ~0.3-20 kDa. Also preferred are polypeptides which have a molecular weight of ~0.3-7.5 kDa.

Further preferred polypeptides are insulin (t ½=12 min; Mw=5.8 kDa), calcitonin (t ½=20 min; Mw=3.4 kDa), GLP-1(7-36) (t ½=6 min; Mw=3.4 kDa), adrenomedullin (t ½=20 min; Mw=6.0 kDa), ADM(27-52) (Mw 3.0 kDa), octreotide (t ½=1.7 h, Mw=1.0 kDa), interleukin-2 (t ½=20 min; Mw=15 kDa) and ganirelix (t ½=12 h; Mw=1.6 kDa). In particular preferred are insulin and [D-Ala$^8$]-GLP-1(7-36). A further embodiment of this invention is a polypeptide conjugate monosubstituted with a pentasaccharide-spacer residue.

The spacer is a bond or an essentially pharmacologically inactive, flexible, linking residue. Preferably, the spacer is an essentially pharmacologically inactive flexible linking residue, in particular having 10-50 atoms counted along the "backbone" of the spacer, the oxygen of the oligosaccharide residue not included. The term "essentially pharmacologically inactive" as used herein means that the spacer does not contain atoms or groups which show pharmacologically activity per se at the doses at which the compounds of the invention are therapeutically effective. Thus, at doses at which the compounds of the present invention are used as therapeutic drugs, the nature of the spacer does not lead to demonstrable pharmacological side-effects.

The spacer may comprise (somewhat) rigid elements, such as ring structures and unsaturated bonds. The spacer of the compounds of the invention is preferably flexible. Suitable spacers may easily be designed by a person skilled in the art. For synthetic reasons longer spacers are considered less suitable, however, longer spacers may still successfully be applied in the compounds of the present invention. Preferred spacers comprise at least one —($CH_2CH_2O$)— element.

Representative examples of the conjugates of the present invention are conjugates of the following structures:
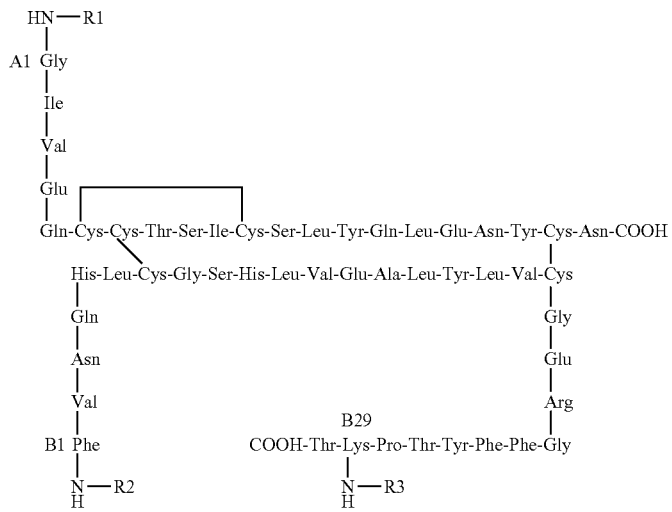
wherein R1=R2=H,
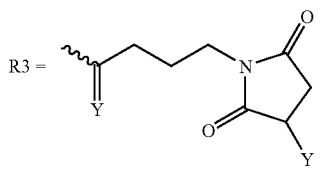
or wherein R1=R3=H,
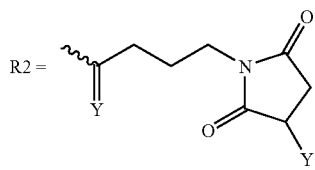
and wherein Y is selected from structures A, B, C and D
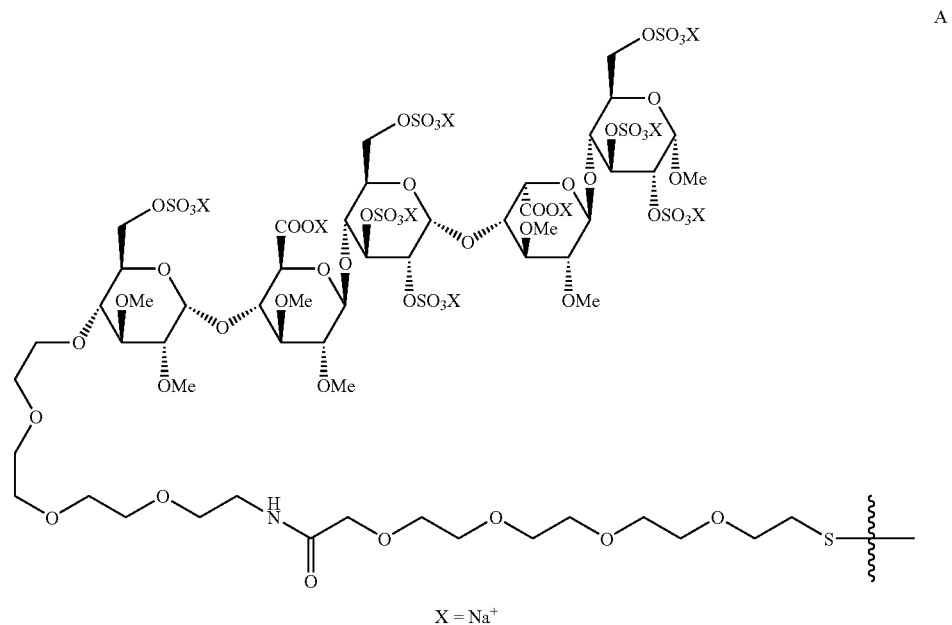
A
X = Na⁺

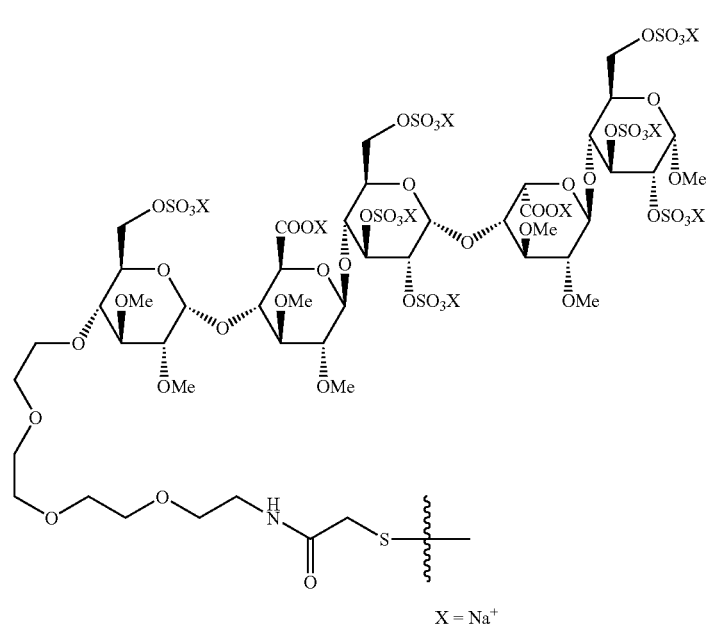
B
X = Na⁺
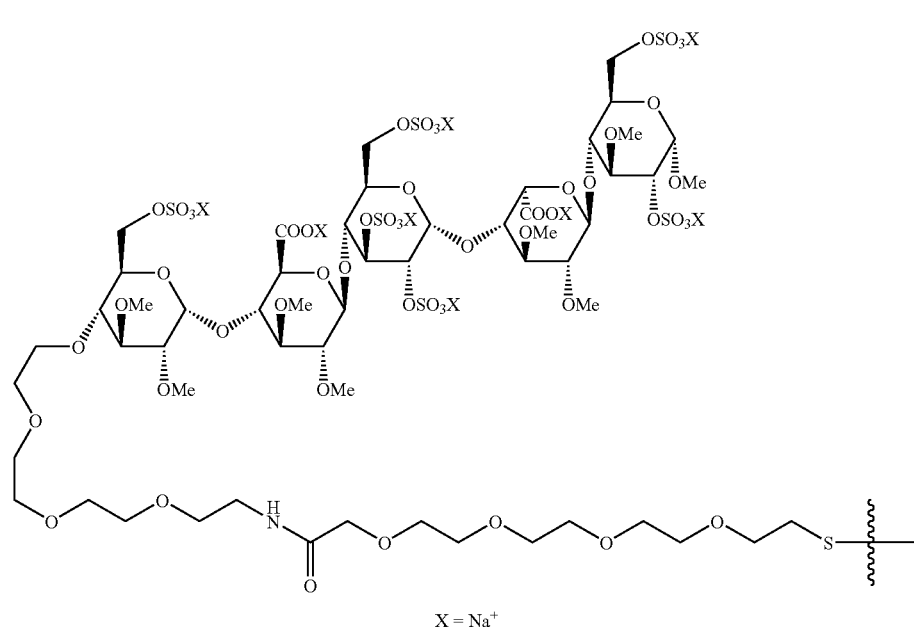
C
X = Na⁺

-continued

D

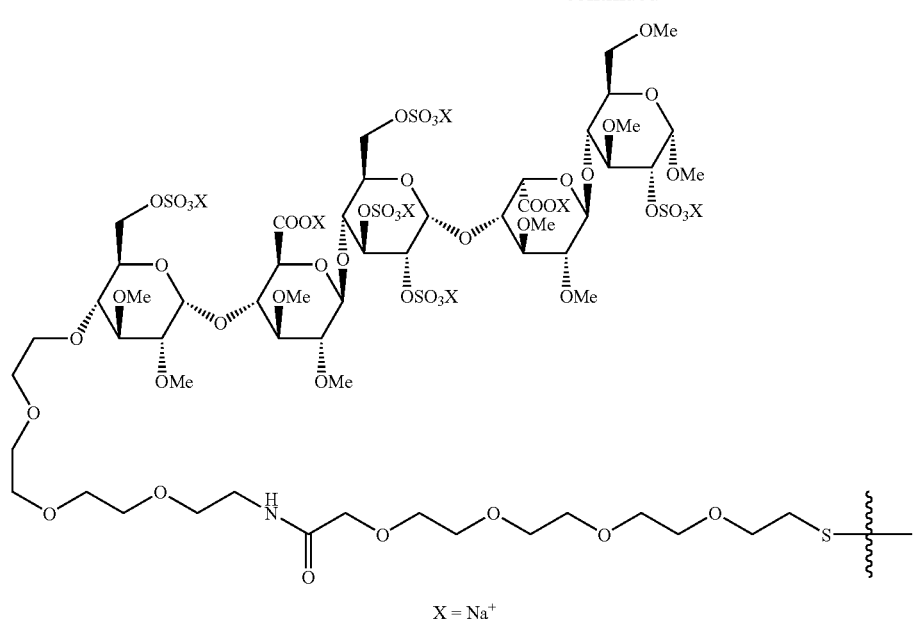

X = Na⁺ or other salts thereof, but also conjugates wherein the spacer is a different one or is attached to the pentasaccharide at another position. Preferred is the sodium salt. And preferably, Y is selected from structures A and B.

Commonly used chemical abbreviations that are not explicitly defined in this disclosure may be found in The American Chemical Society Style Guide, Second Edition, American Chemical Society, Washington, D.C. (1997), "2001 Guidelines for Authors" *J. Org. Chem.* 66(1), 24A (2001), "A Short Guide to Abbreviations and Their Use in Polypeptide Science" *J. Polypeptide. Sci.* 5, 465-471 (1999).

The term polypeptide refers to a chain of at least three amino acids, regardless of post-translational modifications. Polypeptides can be naturally occurring, chemically synthesized, or recombinantly produced polymers of amino acids. Polypeptides that have three to 50 amino acids typically are classified as peptides.

The phrase "polypeptide with catalytic activity" means an enzyme.

The term insulin as used herein refers to the naturally occurring hypoglycemic polypeptide found in mammals, including humans, rat, guinea pig, and rabbits, as well as to recombinant insulin and similar hypoglycemic polypeptides disclosed in U.S. Pat. Nos. 4,652,525, 4,431,740, 5,268,453, 5,506,202, 5,514,646, and 5,700,662.

In the description of the conjugates of the invention further the following definitions are used.

The terms (1-4C)alkyl and (1-8C)alkyl mean a branched or unbranched alkyl group having 1-4 and 1-8 carbon atoms, respectively, for example methyl, ethyl, propyl, isopropyl, butyl, sec-butyl, tert-butyl, hexyl and octyl. Methyl and ethyl are preferred alkyl groups.

The term (1-8C)alkoxy means an alkoxy group having 1-8 carbon atoms, the alkyl moiety having the meaning as previously defined. Methoxy is a preferred alkoxy group.

The spacer length is the number of atoms of the spacer, counted along the shortest chain between the oligosaccharide residue and the polypeptide, not counting the oxygen atom of the oligosaccharide residue which is connected to the spacer.

An embodiment of this invention is further a process for the preparation of a therapeutically active conjugate comprising a polypeptide, the conjugate having negligible anti-thrombotic activity, wherein the conjugate has a longer plasma half-life than the original polypeptide while the biological activity is essentially retained, comprising a step wherein a synthetic sulfated oligosaccharide, in particular wherein the oligosaccharide consists of 4-6 monosaccharide units, and most particularly being a sulfated pentasaccharide, per se having affinity to antithrombin III is attached to the polypeptide, optionally through an essentially pharmacologically inactive flexible linking residue.

General Synthetic and Analytic Aspects

Synthesis of Pentasaccharides

The ATIII-binding oligosaccharide, in particular pentasaccharide, of the compounds of the present invention can be prepared as described for instance in *Angew. Chem. Intl. Ed. Engl.* 1994, 32, 1671-1690. Different oligo- and pentasaccharides with altered affinity for ATIII may be obtained by varying the intermediate mono-, di- or tetrasaccharide building blocks, for instance, by introduction of (permanent) alkyl groups or application of different (temporary) protecting groups giving access to differently sulfated oligo- and pentasaccharides in a controlled fashion (e.g. Westerdu in et. al. *Bioorg. Med. Chem.* 1994, 1267). The spacer may be introduced as described for instance in WO 2001/42262. The oligo- and pentasaccharide-spacer molecule may further be derivatised with linking residues such as the gamma-maleimido butyryl (GMB) group, the N-hydroxysuccinimide (NHS) group or optionally protected thiol group (e.g. *Angew. Chem. Intl. Ed. Engl.* 1996, 35, 331-333) to allow direct coupling with an optionally modified polypeptide.

Conjugation

In general, the conjugates of the invention are produced according to a process comprising (a) an optional step wherein the polypeptide is adapted for conjugation, and (b) a coupling step wherein the optionally adapted polypeptide is reacted with an oligo- or pentasaccharide-spacer molecule.

General synthetic methods for the production of bioconjugates are described in "Bioconjugate Techniques" by Greg T.

Hermanson, 1996, Academic Press. In addition, for conjugation may be considered a Staudinger ligation (such as described by K. L. Kiick et al. *Proc. Nat. Acad. Sci.* 2002; 99:19-24) or a Huisgen's 1,3-dipolar cycloaddition using a pentasaccharide derivative and polypeptide independently modified with an alkyne or azide functional group. Alternatively, enzymatic reactions such as the regioselective IgA protease mediated elongation of polypeptides at the N-terminus (as described by M. Lewinska et al. in *Bioconjugate Chem.* 2004, 15, 231-234) or the transglutaminase catalyzed introduction of amino spacer containing oligosaccharides (as described by M. Sato et al. in *J. Am. Chem. Soc.* 2004, 126, 14013-14022) can be adapted for conjugation of a pentasaccharide spacer residue to an optionally modified polypeptide.

Further, PEGylation of for instance insulin, GLP-1 and octreotide is well documented. In these proteins, a ~5-30 kDa PEG-moiety can be introduced without abolishing their biological activities; such strategies may be followed for the (site-specific) introduction of a pentasaccharide(spacer)-moiety. Furthermore, it is a prerequisite that binding of the pentasaccharide-conjugate to ATIII (~50 kDa) has no substantial deleterious effect on the biological activity of the polypeptide.

Insulin: The N-terminal B-1 and near C-terminal B-29 Lysine amino functions are not essential for the bioactivity of insulin. B1-PEGylated insulin has been prepared (S. W. Kim et al., *Adv. Drug Del. Rev.* 2002, 54, 505-530) in 20% overall yield via reaction of a N-hydroxysuccinimide (NHS) activated PEG derivative with di-N-Boc-protected insulin. Similar reaction of a bifunctional coupling reagent such as N-maleimidobutyryloxy succinimide ester (GMBS) gives access to B1-modified insulin pentasaccharide conjugates. Alternatively, the B29 Lys residue of unprotected $Zn^{2+}$-insulin can be selectively modified with an excess of NHS ester at pH ~10-11 in ~60% yield. Other well established methods for the regioselective conjugation to insulin may be adapted from WO 98/02460, WO 2004/091494, WO 2005/012346, US2005/0152848, Jensen et al. *J. Pept. Sci.* 2005, 11, 339-346, Lee et al. *Bioconj. Chem.* 2005, 16, 615-620, Jain et al. *Biochim. Biophys. Act.* 2003, 1622, 42-49, Tessmar et al. *Tissue Engin.* 2004, 10, 3, 441-453).

Ganirelix: NHS ester derivatives of a pentasaccharide can be conjugated to the free N-terminal amino group of de-N-Ac ganirelix or an amino spacer containing pentasaccharide derivative can be conjugated, optionally via an additional spacer, to the free terminal carboxylic acid group of desamido ganirelix which can in turn be obtained by advanced (solid phase) peptide synthesis as described for instance in *J. Med. Chem.* 1992, 35, 3942-3948.

Octreotide: The N-terminal D-Phe amino acid residue of octreotide, a commercially available peptide, can be modified with up to 5 kDa PEG without abolishing the bioactivity (D. Hee et al. *Pharm. Res.* 2005, 22, 743-749). Regiospecific functionalization of the N-terminal amino group can be achieved with an excess of bifunctional NHS ester linking reagent at pH ~6, upon which further conjugation to a carrier pentasaccharide can be effected according to general synthetic methods for the production of bioconjugates as described above (e.g. by conjugation of a pentasaccharide spacer residue containing a thiol group to a maleimide derivative of octreotide). ADM(27-52): The N-terminal half of full length adrenomedullin (ADM) is not essential for its osteogenic activity and inhibitory effect on vascular calcification. Regiospecific conjugation of a pentasaccharide-spacer residue to the N-terminal Ala residue of ADM(27-52) can be achieved by synthesizing optionally N-terminally modified ADM(27-52) using well established methods employing solid phase peptide synthesis and general synthetic methods for the production of bioconjugates as described above.

[D-Ala$^8$]-GLP-1(7-36): The C-terminal portion of GLP-1 (7-36) and it's derivatives such as Exendin-4(1-39) form an α-helical structure in which amino acid residues are exposed that are important for receptor binding. Extension of this amino acid sequence with an additional lysine residue that is modified at the $N^\epsilon$-position with a maleimide function, using an adapted solid phase peptide synthesis as described for instance in WO 2005/058954, still exhibits receptor binding and in vivo functional activity after covalent binding to the $Cys^{34}$ amino acid of human serum albumin, while the proteolytic stability may (further) be improved by incorporating a D-Ala residue at position 2 (*Bioorg. Med. Chem. Lett.* 2004, 14, 4395-4398). In a similar manner GLP-1(7-36) or analogues thereof can be conjugated to a suitably functionalized pentasaccharide-spacer moiety (e.g. containing a thiol group). Alternatively, a Cys amino acid can be incorporated in the peptide sequence, preferably at position(s) 11, 12, 16, 22, 23, 24, 25, 26, 27, 30, 34, 35 or 36 or added at position 37, and which may be coupled to a suitably functionalized pentasaccharide-spacer moiety (e.g. containing a maleimide group), using methods similar as described for the PEGylation of GLP1 derivatives (WO 2004/093823). Furthermore, conjugates of GLP-1 may be obtained by direct coupling to a bifunctional NHS ester linking reagent to GLP-1, followed by separation of the positional isomers (as described for instance for the direct PEGylation of GLP-1 by Lee et al. *Bioconjugate Chem.* 2005, 16, 377-382) and coupling to a suitably functionalized pentasaccharide-spacer moiety.

Interleukin-2 (IL-2): the free $Cys^{125}$ amino acid of commercially available native recH-IL2, or free (additional) Cys amino acids of IL2 muteins that are still biologically active, can be reacted with a pentasaccharide-spacer moiety containing a maleimide group according to a similar protocol as described for the PEGylation of IL2 (U.S. Pat. No. 5,206,344) with PEG-maleimide.

The peptide coupling, a possible procedural step in the above described method to prepare the compounds of the invention, can be carried out by methods commonly known in the art for the coupling—or condensation—of peptide fragments such as by the azide method, mixed anhydride method, activated ester method, the carbodiimide method, or, preferably, under the influence of ammonium/uronium salts like TBTU, especially with the addition of catalytic and racemisation suppressing compounds like N-hydroxysuccinimide, N-hydroxybenzotriazole and 7-aza-N-hydroxybenzotriazole. Overviews are given in *The Peptides, Analysis Synthesis, Biology*, Vol. 3, E. Gross and J. Meienhofer, eds. (Academic Press, New York, 1981) and *Peptides: Chemistry and Biology*, N. Sewald and H.-D. Jakubke (Wiley-VCH, Weinheim, 2002).

Amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, the 9-fluorenylmethyloxycarbonyl (Fmoc) group or the phthaloyl (Phth) group, or may be introduced by demasking of an azide moiety. Overviews of amino protecting groups and methods for their removal is given in the above mentioned *The Peptides, Analysis, Synthesis, Biology*, Vol. 3 and *Peptides: Chemistry and Biology*.

The compounds of the invention, which may occur in the form of a free base, may be isolated from the reaction mixture in the form of a pharmaceutically acceptable salt. The pharmaceutically acceptable salts may also be obtained by treating the free base of formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention or intermediates thereof may possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

Physico- and Biochemical Analysis

Several techniques to monitor the effect of the reaction with bifunctional linkers and/or reactive pentasaccharide-moieties on the bioactivity of the protein are available. In this respect, biomolecular interaction analysis (BIA), using soluble receptor molecules as complementary binding agents (insulin) and determination of enzyme activity are valuable tools. Binding studies of the pentasaccharide-conjugate to ATIII can be included in these assays as well.

Ion exchange, size exclusion chromatography and ATIII affinity chromatography are available methods for subfractionation of the pentasaccharide conjugates, while electrophoresis techniques are suitable for orthogonal, qualitative and quantitative characterization (e.g. SDS-PAGE, CZE). Conjugation sites can be identified by MALDI-TOF MS analysis and N-terminal sequencing of the conjugates.

Pharmacokinetic (PK) Studies

PK studies to determine the in vivo half-life of the unmodified polypeptide and the corresponding pentasaccharide conjugates can be carried out in rats. Several options are available, e.g. radiolabeling with $^{125}$I employing Iodogen or lactoperoxidase ionisation to induce electrophilic substitution or using Bolton-Hunter reagent as labeling moiety and determining gamma-radiation in plasma samples. Other methods known in the art are based on injection of unlabeled conjugates followed by immunochemical analysis through ELISA or Luminex technology.

Pharmacological Evaluation

The pharmacological effects of conjugation of polypeptides of the invention to an ATIII binding pentasaccharide can be studied in in vitro assays and in vivo animal models as described below.

Insulin is a 5.8 kDa protein consisting of two peptide chains which are held together by two disulfide bridges. Site-specific chemical modification at one of the Lys ε-amino or N-terminal α-amino groups is well documented. The effect of conjugation of a pentasaccharide to insulin can be studied by analyzing serum samples for glucose, insulin and C-peptide content (a biomarker to correct for endogenous insulin secretion). A glucometer and human insulin and C-peptide radioimmunoassays are commercially available. In vivo effects of insulin on the blood glucose levels can be measured in rats or Beagle dogs.

The pharmacological in vitro and in vivo effects of pentasaccharide conjugation of the decapeptide mimetic GnRH antagonist ganirelix can be studied in established assays and animal models. Advanced polypeptide synthesis will deliver a well-defined molecule of which the effects can be compared to ganirelix blocking oocyte maturation and ovulation in mouse and rat. Comparison of biological half-life of ganirelix and its pentasaccharide-conjugated counterpart may for instance be studied by determining at which time after administration the natural process of maturation and ovulation has restored.

GLP-1(7-36) is a well known and well studied insulinotropic endocrine hormone inducing numerous biological effects such as stimulating insulin secretion, inhibiting glucagon secretion, gastric or intestinal motility, enhancing glucose utilization and inducing weight loss. It is rapidly degraded by dipeptidyl peptidase IV (DPPIV). The latter premature degradation may for instance be circumvented by replacement of the amino acid residue at position 8 (e.g. by D-alanine). Other approaches such as modification with large fatty acid chains or PEG have resulted in biologically active GLP-1 or analogs thereof (as defined in e.g. WO 2004/093823). The (additional) stabilizing effect of conjugating an optionally modified GLP-1(7-36) derivative to a carrier pentasaccharide can be studied by measuring the stability of the conjugate in vitro in the presence of DPPIV and in vivo by measuring the plasma half life using immunochemical analysis. The functional activity of the GLP-1 pentasaccharide conjugate can be determined in vitro by measuring the ability to bind to and activate the GLP-1 receptor and in vivo pharmacodynamic effects can be studied by analyzing serum samples for glucose and insulin.

Adrenomedullin is a 52-amino acid polypeptide with numerous biological functions such as vasodilation, bronchodilation, neurotransmission, growth regulation and regulation of bone formation. The truncated fragment ADM(27-52) lacks the structural requirements for vasodilator activity but is still able to stimulate the growth of cultured rat osteoblasts in a dose-dependent manner (*Regulatory Peptides* 2003, 112, 79-86). In addition, it was recently established that ADM(27-52) inhibits vascular calcification in rats (*Regulatory Peptides* 2005, 129, 125-132) and may thus have potential therapeutic application in the prevention of artery calcification. The effect of conjugating ADM(27-52) to a carrier pentasaccharide may be assessed by well established assays, measuring the in vitro osteogenic activity in cultures of actively growing fetal rat osteoblasts or the in vivo increase in index of bone formation (without affecting bone resorption).

Octreotide is a synthetic octapeptide analogue of somatostatin and is clinically used for the treatment of acromegaly and certain endocrine tumors. It has been shown that long acting depot formulations (e.g. Sanostatin LAR depot, Novartis Pharma, Basel, Switzerland) are at least as effective in the lowering of plasma growth hormone and insulin-like growth factor (IGF-I) levels compared with three-daily subcutaneous injections. The effect of conjugation of octreotide to a pentasaccharide on its pharmacokinetic and pharmacodynamic properties can be studied in male rats by using established radio immunoassays to determine levels of conjugated octreotide and altered levels of IGF-I.

Interleukin-2 (IL-2) is a protein produced naturally in the body by white blood cells (T-lymphocytes) and is an important protein of the immune system. It is commercially available (Aldesleukin, Proleukin®, Chiron, U.S.) as a drug and is used in the treatment for some types of cancer (hairy cell leukemia) and is used in conjunction with anti-HIV therapy to induce increases in CD4 cell counts. The specific bioactivity of pentasaccharide-IL-2 conjugates can be determined in vitro using the IL-2 cell proliferation bioassay described by Gillis et al. (*J. Immunol.* 1978, 120, 2027-2032).

Pharmaceutical Formulations

The conjugates of the invention may be administered enterally or parenterally. The exact dose and regimen of these compounds and compositions thereof will necessarily be dependent upon the biological activity of the polypeptide per se, the needs of the individual subject to whom the medicament is being administered, the degree of affliction or need and the judgment of the medical practitioner. In general, parenteral administration requires lower dosages than other methods of administration which are more dependent upon absorption. However, the daily dosages are for humans preferably 0.0001-1 mg per kg body weight, more preferably 0.001-0.1 mg per kg body weight.

The medicament manufactured with the compounds of this invention may also be used as adjuvant in therapy. In such a case, the medicament is administered with other compounds useful in treating such disease states.

Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts. When administration is intravenous, pharmaceutical compositions may be given as a bolus, as two or more doses separated in time, or as a constant or non-linear flow infusion. Thus, compositions of the invention can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions of this invention comprise the compounds of the present invention and pharmaceutically acceptable salts thereof, with any pharmaceutically acceptable ingredient, excipient, carrier, adjuvant or vehicle.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is further illustrated by, but not limited to, the following examples. It will be understood that various modifications may be made with different pentasaccharides, spacers and polypeptides without departing from the spirit and scope of this invention.

LEGENDS TO THE FIGURES

FIG. 1.
Recognition of pentasaccharide-insulin conjugate 6 (Insulin-penta) by insulin-specific ELISA.

Figure 2A:
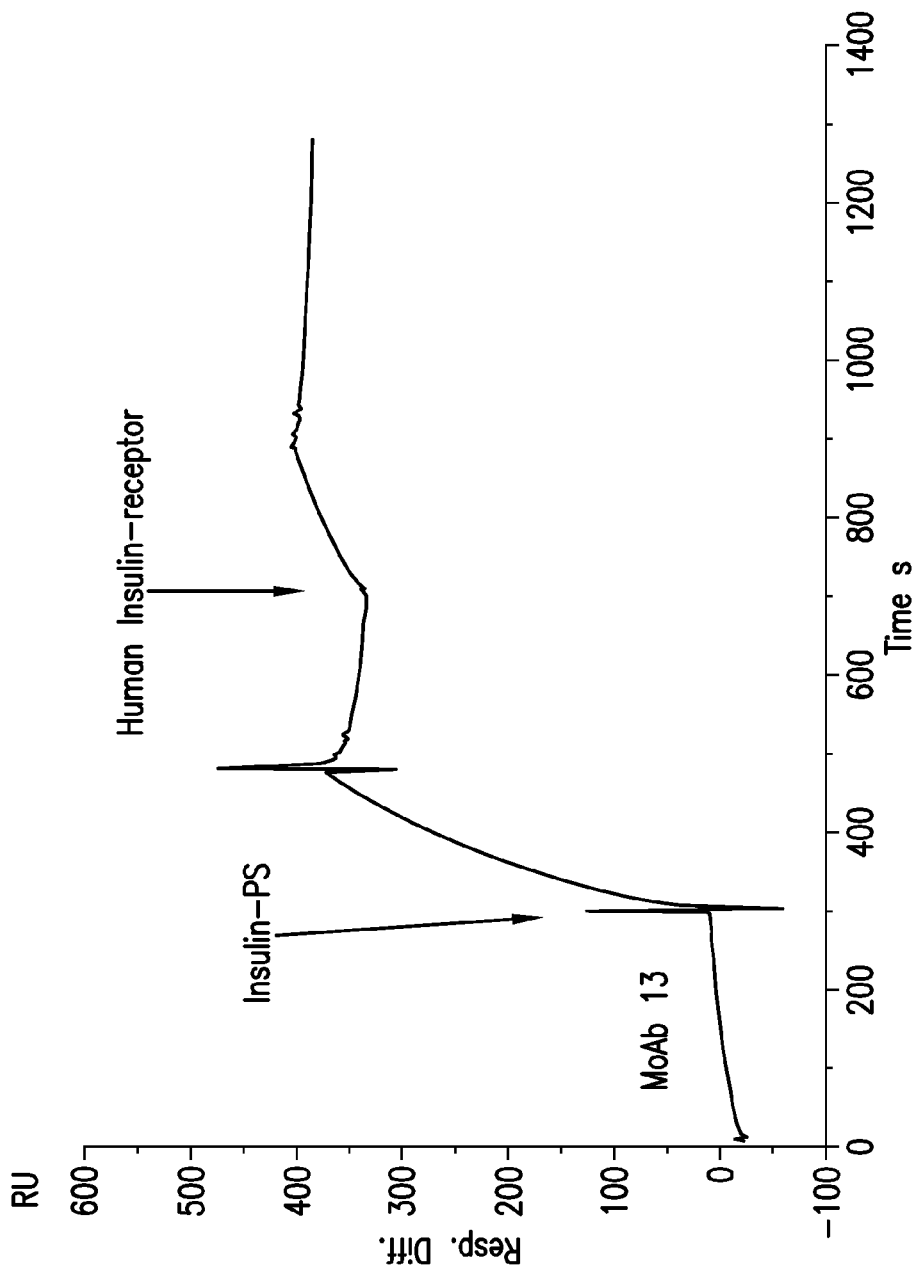

FIG. 2A.
Biomolecular interaction analysis of pentasaccharide(PS)-insulin conjugate 6.
Reaction of immobilized anti-insulin antibody with insulin conjugate with subsequent binding to human insulin receptor.

Figure 2B:
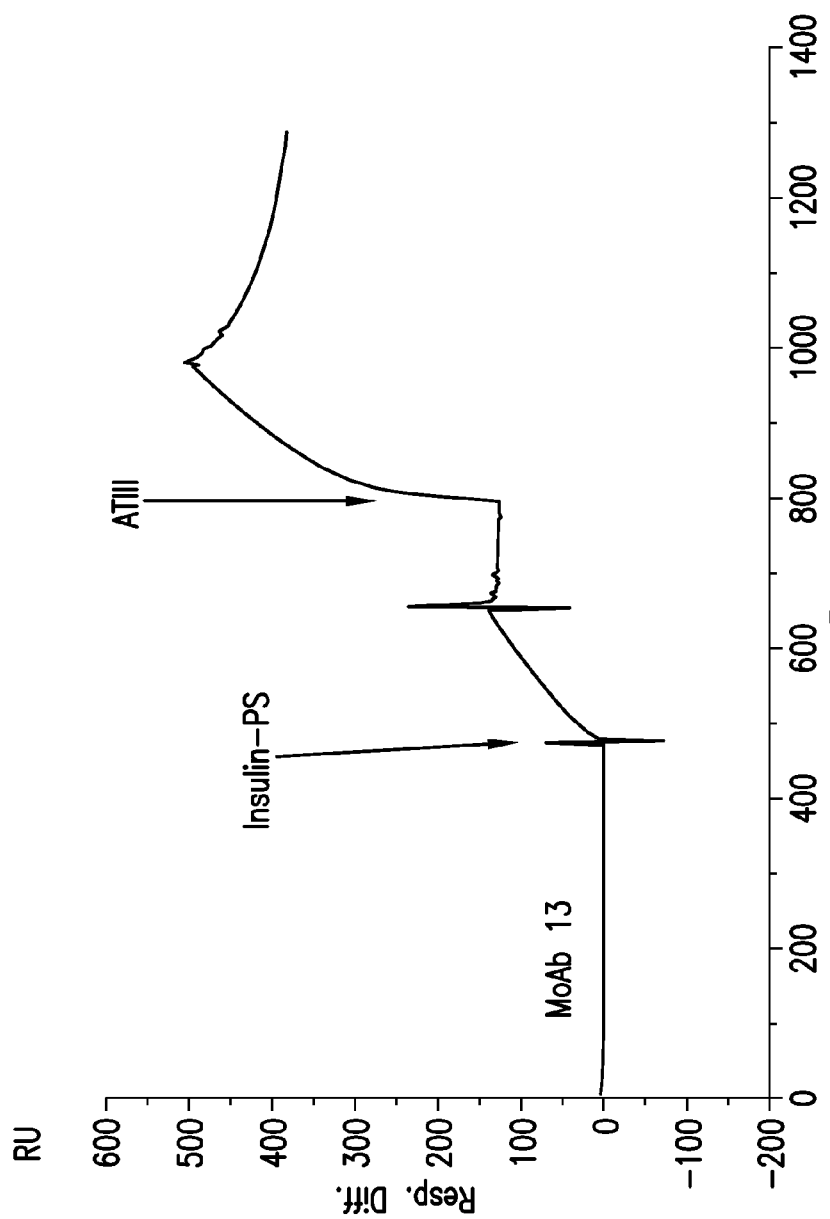

FIG. 2B.
Biacore analysis of pentasaccharide(PS)-insulin conjugate 6.
Reaction of immobilized anti-insulin antibody with insulin conjugate with subsequent binding of human ATIII.

Figure 3:
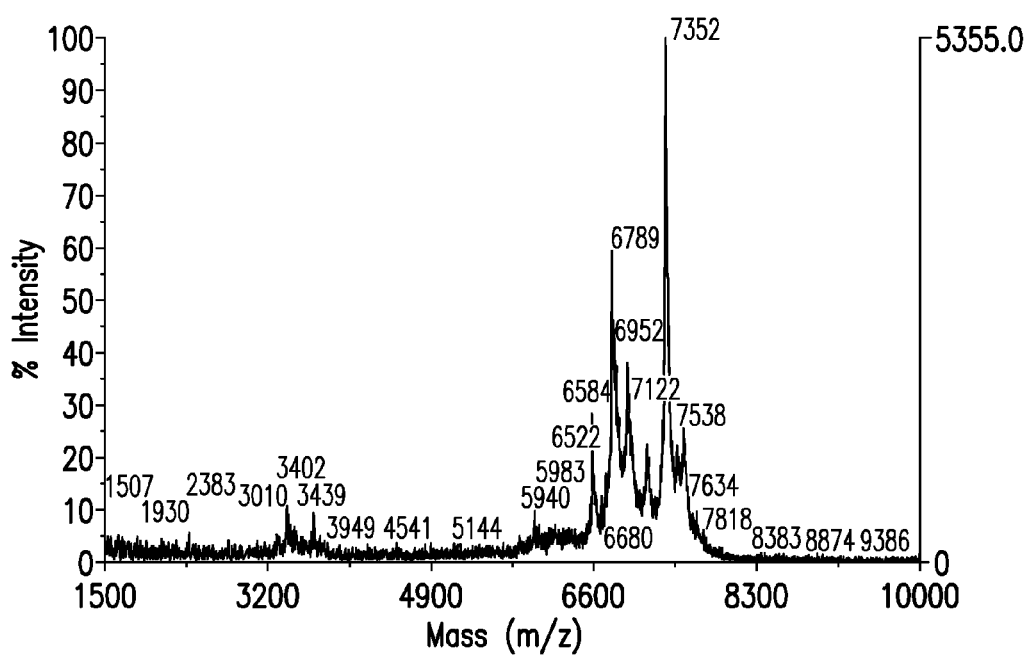

FIG. 3.
MALDI-TOF analysis of monosubstituted pentasaccharide-insulin conjugate 6.

Figure 4:
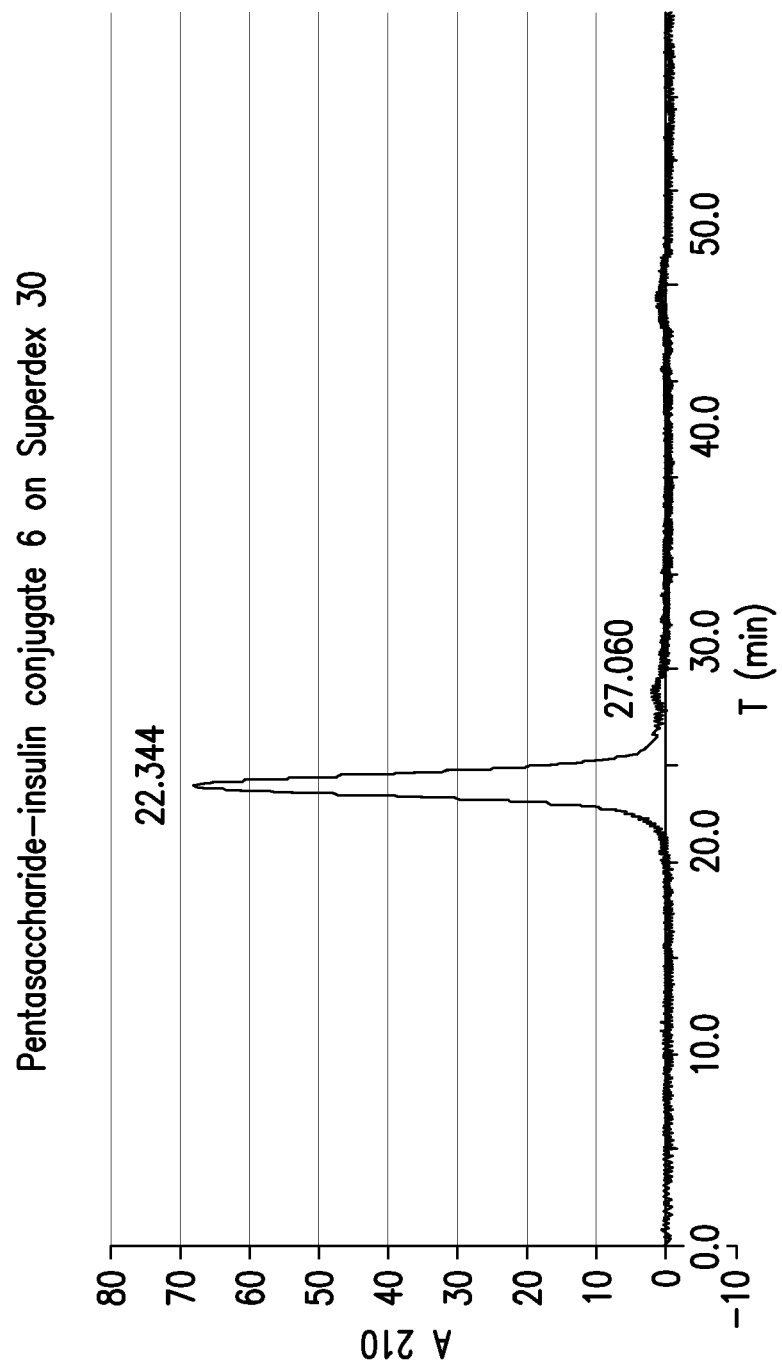

FIG. 4.
HP-SEC analysis of monosubstituted pentasaccharide-insulin conjugate 6 on Superdex 30.

Figure 5:
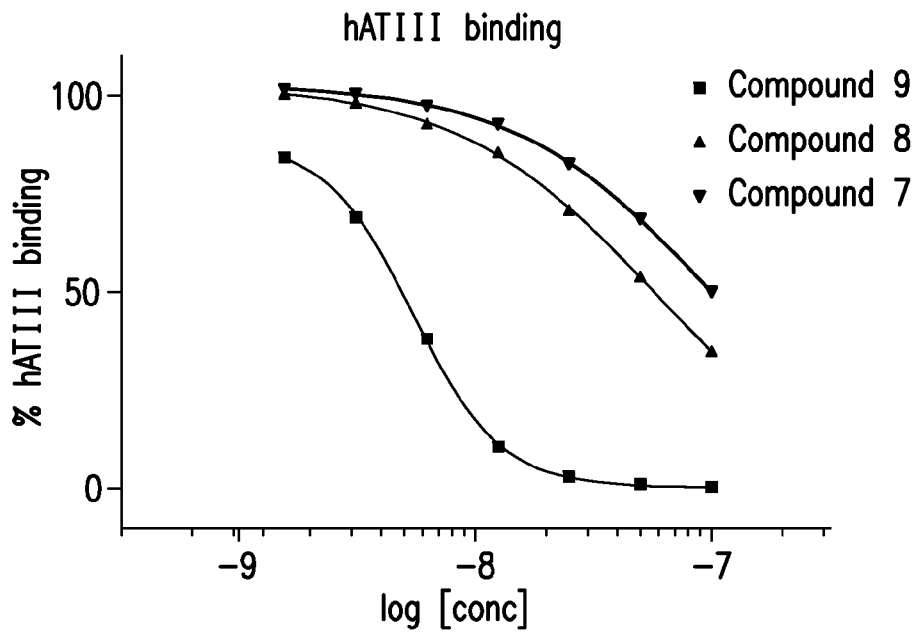

FIG. 5.
hATIII binding of reference pentasaccharide-spacer residues 7, 8 and 9 (BIA study).

Figure 6:
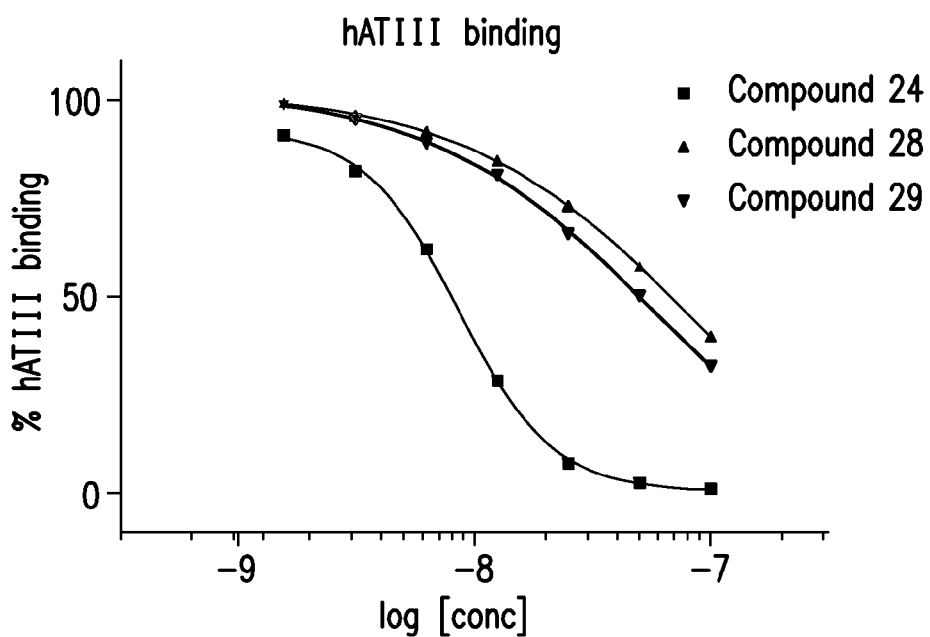

FIG. 6.
hATIII binding of insulin-pentasaccharide conjugates 24, 28 and 29 (BIA study).

Figure 7:
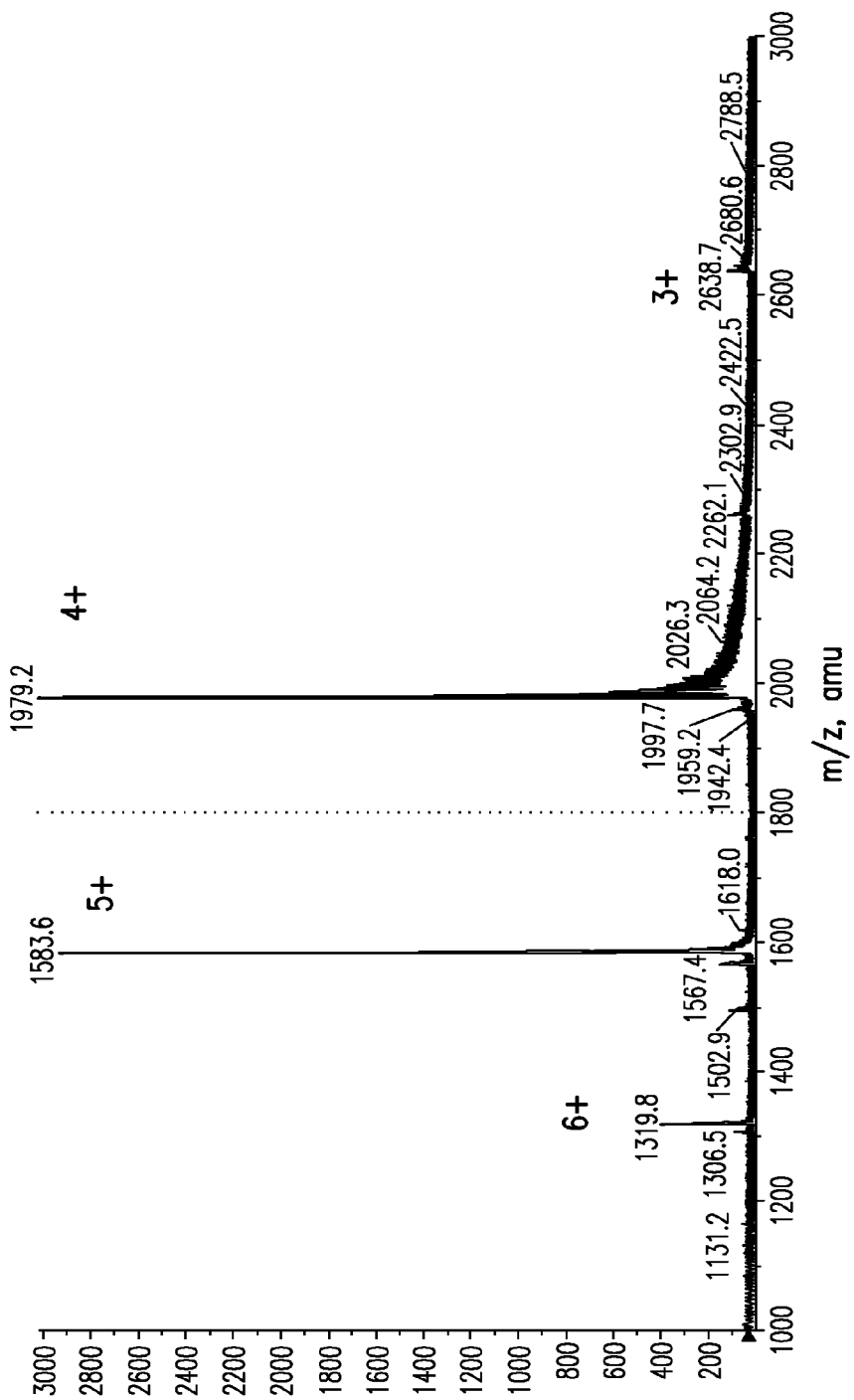

FIG. 7.
Mass spectrometric analysis (ESI-QTOF) of insulin-pentasaccharide conjugate 24

Figure 7A:
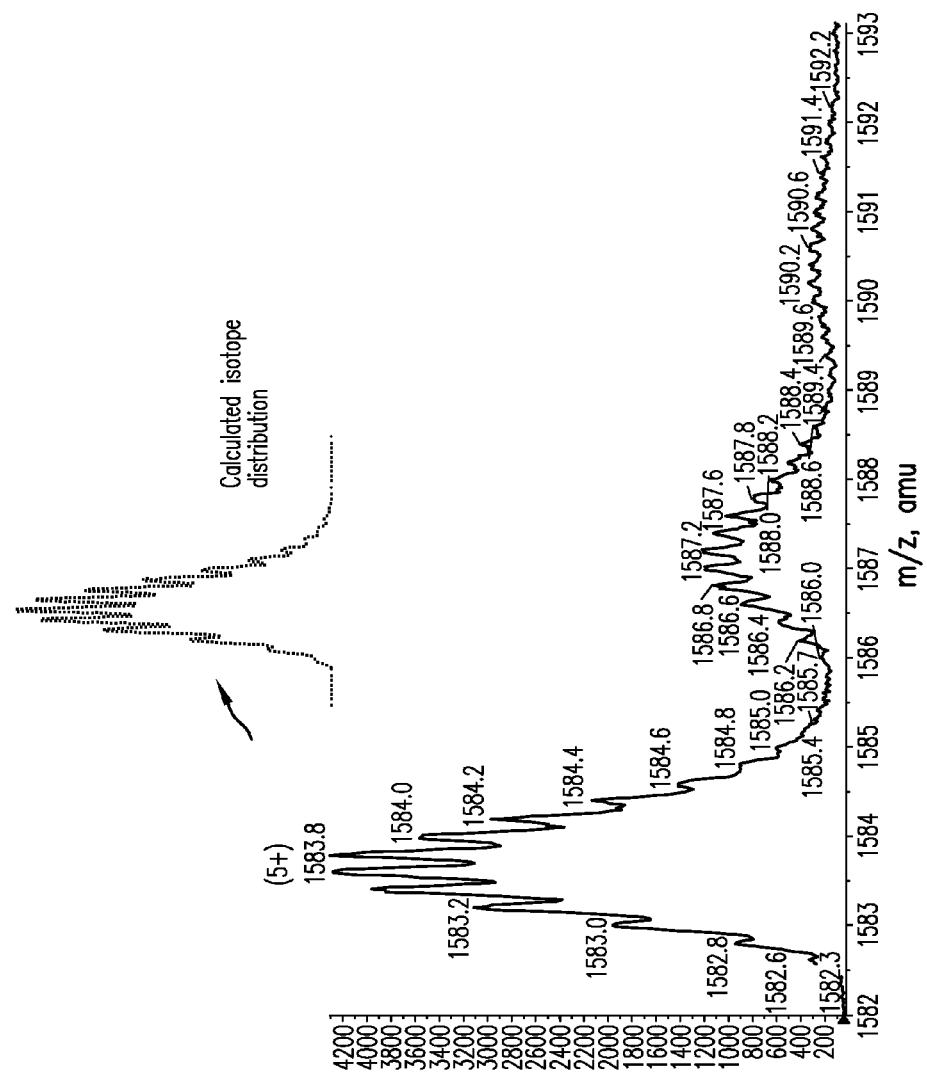

FIG. 7A.
Comparison of an experimentally determined and calculated typical isotope distribution of an insulin-pentasaccharide conjugate (ESI-QTOF, $M^{5+}$, compound 24)

Figure 8:
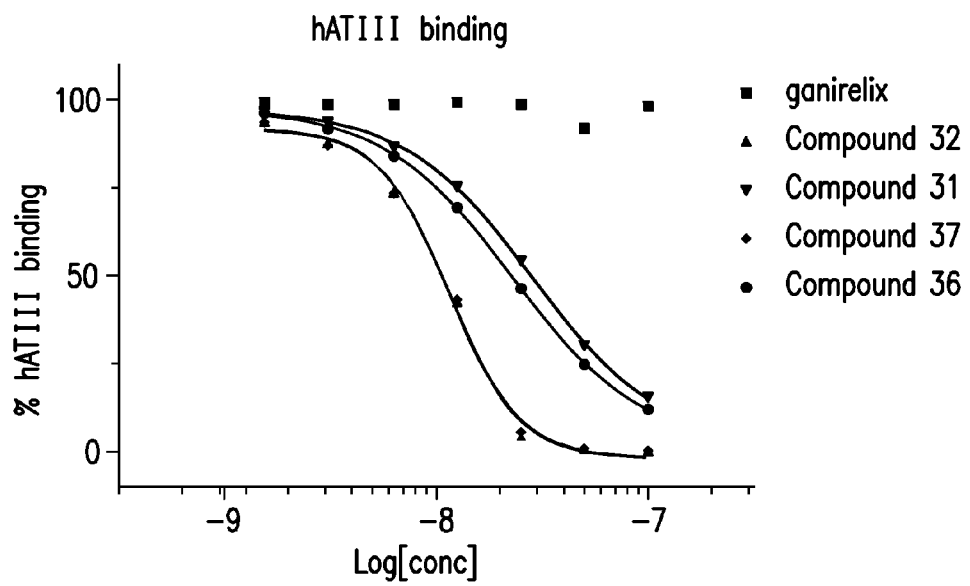

FIG. 8.
hATIII binding of compounds 31, 32, 36, 37 (Biacore study).

Figure 9:
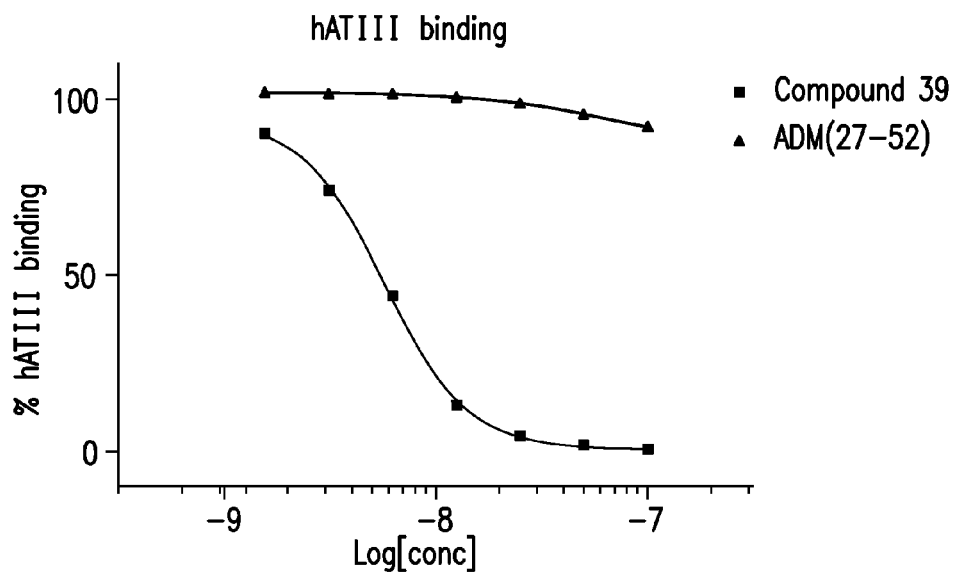

FIG. 9.
hATIII binding of compound 39 (as determined by BIA).

Figure 10:
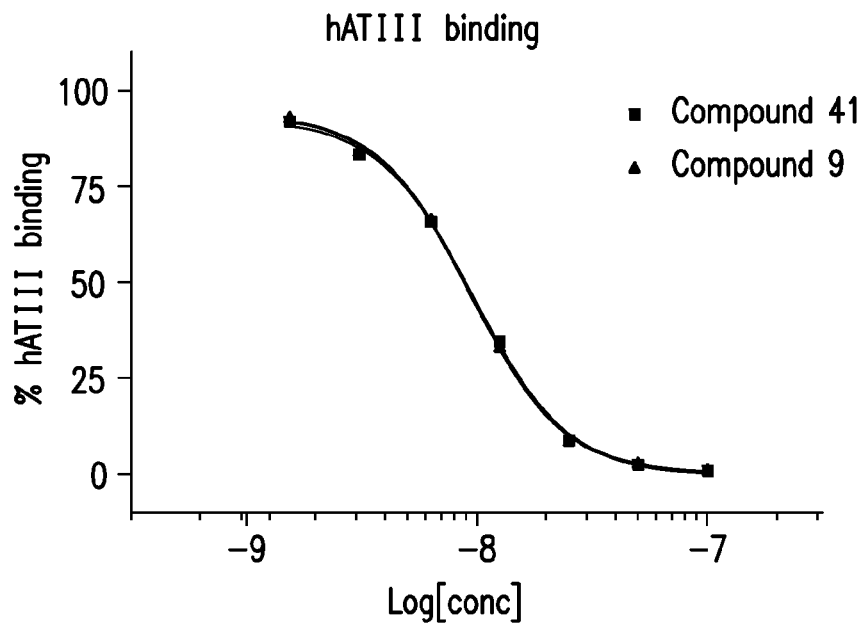

FIG. 10.
hATIII binding profile of compound 41 (as determined by BIA).

Figure 11:
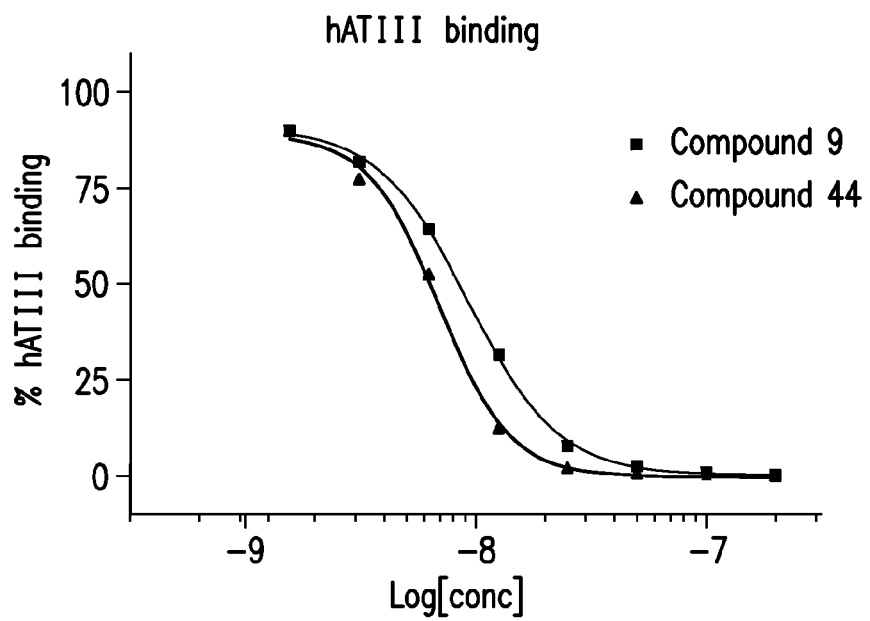

FIG. 11.
hATIII binding profile of compound 44 (as determined by BIA).

Figure 12:
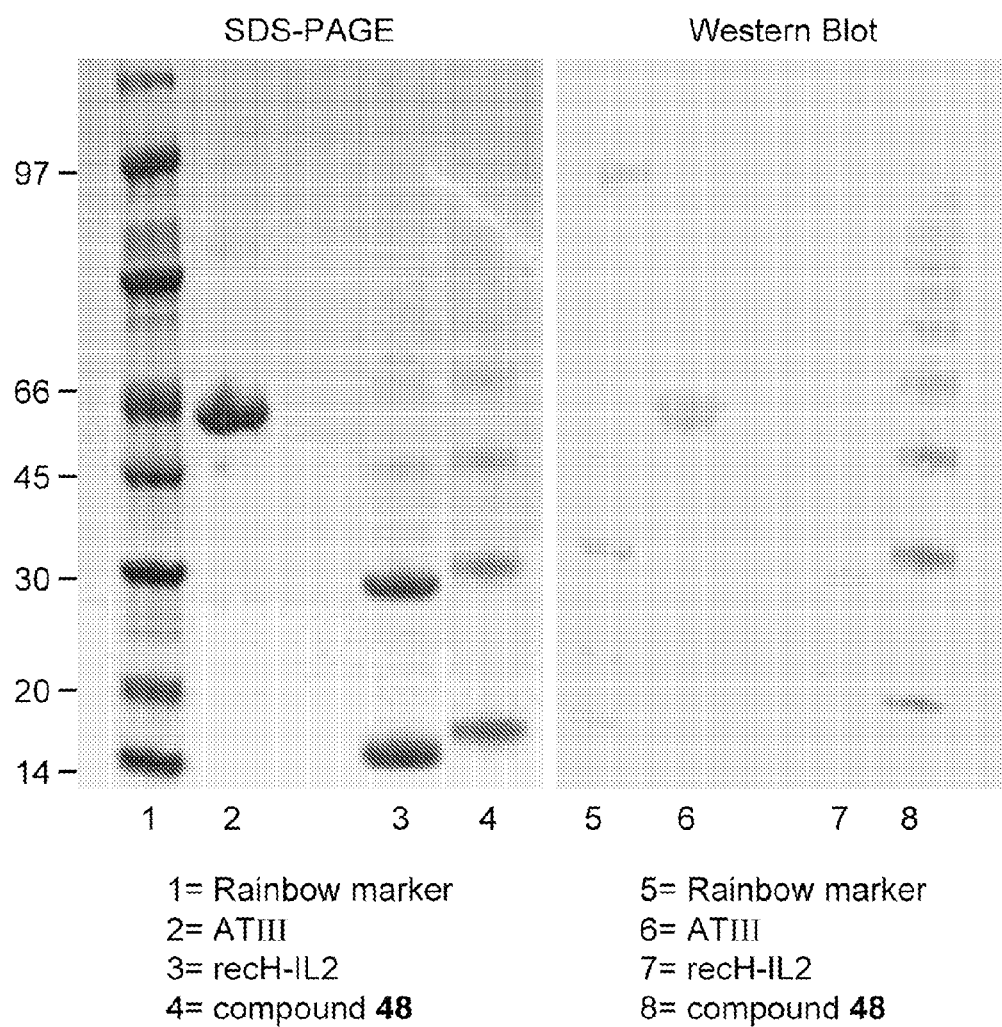

FIG. 12.
SDS-PAGE and Western blot analyses of compound 47

FIG. 13.

Mean plasma levels (mean±s.e.m.) determined by measurement of the insulin concentration after i.v. administration of 3.5 nmol/kg recH insulin (open circles) or pentasaccharide-insulin conjugate 6 (triangles).

FIG. 14.

Mean plasma levels (mean±s.e.m.) expressed as % of the concentration measured at T=1 minute after i.v. administration of $^{125}$I-labeled conjugate 29 (open squares), 24 (open circles) and 28 (open triangles) and of recH insulin itself (closed bullets).

FIG. 15.

Mean plasma levels (mean±s.e.m.) expressed as % of the concentration measured at T=1 minute after i.v. administration of $^{125}$I labeled conjugate 31 (open squares) and 32 (closed triangles). (Data not corrected for dehalogenation).

FIG. 16.

Mean plasma levels (mean±s.e.m.) expressed as % of the concentration measured at T=1 minute after i.v. administration of $^{125}$I labeled conjugate 39 (open squares) and of $^{125}$I labeled ADM(27-52) (closed triangles). (data not corrected for dehalogenation).

FIG. 17.

Mean plasma levels (mean±s.e.m.) expressed as % of the concentration measured at T=1 minute after i.v. administration of $^{125}$I labeled conjugate 41 (closed triangles) and of $^{125}$I labeled GLP-1 (open squares).

FIG. 18.

Detection of the pentasaccharide-insulin conjugate 6-ATIII complex with anti-human and anti-rabbit ATIII antibodies.

FIG. 19.

Mean glucose levels (mean±s.e.m.) after i.v. administration of 7 nmol/kg pentasaccharide-insulin conjugate 6 (open triangles) or 3.5 nmol/kg recH-insulin (open circles).

FIG. 20.

Mean glucose levels (mean±s.e.m.) after i.v. administration of 12 nmol/kg pentasaccharide-insulin conjugate 26 (closed triangles) and 24 (closed circles) compared to the glucose levels after treatment with 9 nmol/kg recH-insulin (open circles).

FIG. 21.

Mean glucose levels (mean±s.e.m.) after i.v. administration of 24 nmol/kg pentasaccharide-insulin conjugate 27 (closed squares) or 25 (closed diamonds) compared to the glucose levels after treatment with 9 nmol/kg recH-insulin (open circles) or 48 nmol/kg of Insulin Detemir (open triangles).

FIG. 22.

Mean glucose levels (mean±s.e.m.) after i.v. administration of 24 nmol/kg pentasaccharide-insulin conjugate 24 (closed triangles), 28 (closed circles) or 29 (closed squares) compared to the glucose levels after treatment with 9 nmol/kg recH-insulin (open circles) or 24 nmol/kg of Insulin Detemir (open diamonds).

EXAMPLES

Abbreviations Used

ACN acetonitrile
AcOH acetic acid
ADM adrenomedullin
(h)ATIII (human) anti-thrombin III
AUC area under the curve
BIA biomolecular interaction analysis
$Boc_2O$ di-tert-butyl dicarbonate
Cl clearance
DCCI N,N'-dicyclohexylcarbodiimide
DIPEA diisopropylethylamine
DMF N,N'-dimethylformamide
DMSO dimethyl sulfoxide
EDTA ethylenediamine tetra-acetate
ELISA enzyme-linked immunosorbent assay
Equiv. equivalents
ESI electron spray ionization
GLP-1 glucagon-like peptide 1
GMB gamma-maleimidobutyryl
GMBS gamma-maleimidobutyric acid N-hydroxy succinimic ester
HBS-EP hepes buffered saline containing EDTA and polyethylene glycol
HPLC high performance liquid chromatography
HP-SEC high performance size exclusion chromatography
HRP horse-radish peroxidase
i.v. intravenous
IL-2 interleukin-2
MALDI-TOF matrix assisted laser disportion ionisation time of flight
MoAb monoclonal antibody
MRT mean residence time
MS mass spectrometry
NMM N-methyl morpholin
NMR nuclear magnetic resonance
PAGE polyacrylamide gel electrophoresis
PBS phosphate-buffered saline
PS pentasaccharide
Q-TOF quadropole time of flight
recH recombinant human
RT room temperature
Rt retention time
SDS sodium dodecyl sulfate
TBTU 2-(1H-benzotriazol-1-yl)-1,1,3,3-tetramethyluroniumtetrafluoroborate
TCA trichloroacetic acid
TEA triethylamine
TFA trifluoroacetic acid
THF tetrahydrofuran
Vss volume of distribution at steady state Materials and Methods $^1$H-NMR spectra were recorded at 400 MHz on a Bruker DRX-400 (ultra shield). Chemical shifts in organic solvents are reported in ppm (δ) relative to tetramethylsilane.

DMF, 1,4-dioxane, NMM, ammonium acetate, $Boc_2O$, TFA, DMSO, DCCI (Acros), hydroxylamine (50 wt. % in $H_2O$), iodoacetic anhydride, GMBS (Sigma Aldrich), recH insulin (Diosynth), TEA, 6-aminocaproic acid, N-hydroxysuccinimide (Janssen), THF (Biosolve), 2-mercapto-[S-acetyl]acetic acid N-hydroxysuccinimide ester (13), TBTU (Fluka), ACN (Merck), AcOH and $Na_2HPO_4$ (J.T. Baker) were used as received from the commercial suppliers mentioned.

Column chromatography was performed on MP Biomedicals Germany GmbH kieselgel 60 (MP silica 32-63, 60 Å) and on Merck LiChroprep RP-18 (40-63 µm). TLC analysis was performed on Merck TLC plates kieselgel 60 $F_{254}$. Compounds were visualized by UV absorption (254 nm) and/or charring with USUI reagent (phosphor molybdenic acid/AcOH/$H_2SO_4$ in EtOH).

MALDI spectra were obtained with a Voyager DE PRO (Applied Biosystems, Framingham, Mass., USA) in linear, delayed extraction mode in positive and negative ion mode. Re-crystallized alpha-cyano hydroxy cinnamic acid (CHCA, 3 g/L in 500 mL/L ACN/1 mL/L TFA) was used as matrix. Molecular weights were measured using a two point calibration (e.g. by assigning recH insulin and one of its fragment chains, or myoglobin at m/z 16953 and m/z 8477).

Q-TOF spectra were obtained with a PE Sciex API Q-star Pulsar in positive ion mode with an ESI-source. Samples were dissolved in $H_2O$ and desalted by use of reversed phase Zip Tip®.

Default analytical HPLC was conducted on a Gilson 234 autosampler with three Gilson pumps (305) gradient system using a Luna™ C18(2) column (reversed phase, 150×4.6 mm, 5 µm). A Gilson UV detector (118) was used for detection at 210 nm. Gradient elution was performed at a column temperature of 40° C. and a flow rate of 1 mL/min by starting with 95% of eluent A (0.1% TFA in $H_2O$/ACN, 9:1) and 5% eluent B (0.1% TFA in ACN) for 5 min., then applying a linear gradient from 15 to 50% ACN in 25 min.

Analytical (HPLC) analysis of compound 4 was conducted on a Shimadzu SCL-10A vp (system controller) two way pump gradient system using a Luna™ C18(2) column (reversed phase, 150×2.0 mm, 5 µm). A Shimadzu diode array UV detector (SPD-M10A vp) was used for detection at 214 nm. Gradient elution was performed at a column temperature of 40° C. and a flow rate of 0.4 mL/min.

Preparative HPLC was conducted on a Waters 2769 sample manager with a single pump (Waters 600) gradient system using a Luna™ C18(2) column (reversed phase, 250×50 mm, 10 µm). A Gilson UV detector (2996, photodiode array) was used for detection at 210 nm. Gradient elution was performed at a flow rate of 50 mL/min by starting with 90% eluent A (0.1% TFA in $H_2O$/ACN, 9:1) and 10% eluent B (0.1% TFA in ACN) for 10 min., then applying a linear gradient from 15 to 50% eluent B in 50 min.

Analytical anion exchange chromatography was conducted on a Pharmacia Akta Explorer with a Pharmacia pump (P-900) gradient system using a Pharmacia Biotech MonoQ HR 5/5 column. A Pharmacia UV detector (UV 900) was used for detection at 210 nm in combination with a Pharmacia pH and conductivity detector (pH/C 900). An AD detector (AD900) was used in combination with a Chiralyser (IBZ). Furthermore a Pharmacia fraction collector (Frac 950) and a Pharmacia autosampler (A 900) were used. Default elution was performed with a flow rate of 1 mL/min starting with 74% eluent A (ACN/$H_2O$ 2:8) and 26% eluent B (ACN/2M NaCl 2:8) for 5 min. and then applying a gradient to 20% eluent A and 80% eluent B in 15 min.

Preparative anion exchange chromatography was conducted on a Pharmacia system with a Pharmacia pump (P-50) and a Pharmacia gradient mixer (LKB GP-10) gradient system using a Pharmacia Biotech XK16 Q-sepharose Fast-Flow column. A Pharmacia UV detector (LKB-UV-MII) was used for detection at 214 nm in combination with a Biotechnics conductivity detector. Default gradient elution was performed at a flow rate of 4.6 mL/min by starting with 80% eluent A ($H_2O$) and 20% eluent B (2M NaCl in $H_2O$) for 20 min., then applying a gradient to 20% eluent A and 80% eluent B in 210 min.

Preparative gel filtration on Sephadex G25 (desalting) was conducted on a Pharmacia system with a Watson-Marlow pump (101V) using a Pharmacia Biotech XK26 Sephadex-G25 fine column. A Pharmacia UV detector (LKB-UV-MII) was used for detection at 214 nm in combination with a Biotechnics conductivity detector. Isocratic elution was performed with $H_2O$ at a flow rate of 1 mL/min $H_2O$ for 10 h.

Analytical HP-SEC with compound 6 was carried out on a Pharmacia Superdex™ 30 HR 10/30 column mounted in a HP1100 chromatography system. Elution was performed with 0.2 mol/L sodium phosphate buffer pH 7.0 at a flow rate of 0.4 mL/L.

Analytical HP-SEC with the other conjugates was conducted on the Akta Explorer system as described for the analytical Q-sepharose chromatography, with a Pharmacia Superdex™ 75 HR 10/30 column. An isocratic elution was performed with 50 mM ammonium acetate at a flow rate of 1 mL/min.

Preparative HPSEC was conducted on the same Akta Explorer system as described for the analytical Q-sepharose chromatography, with a Pharmacia Superdex™ 75 XK26 Hiload 26/60 prep-grade column. An isocratic elution was performed with 50 mM ammonium acetate at a flow rate of 1.32 mL/min.

Binding studies of pentasaccharide conjugates to ATIII, anti-insulin antibody and insulin receptor were performed using BIAtechnology. The sensorgrams and report points were analysed with blanc flow cell subtraction using BIAevaluation 3.2. $IC_{50}$ values were calculated using graphpad Prism 3.0.

$A_{280}$ measurements were performed on a Nano Drop® ND-1000 UV-VIS spectrophotometer.

Scheme 1. Synthesis of compound 4

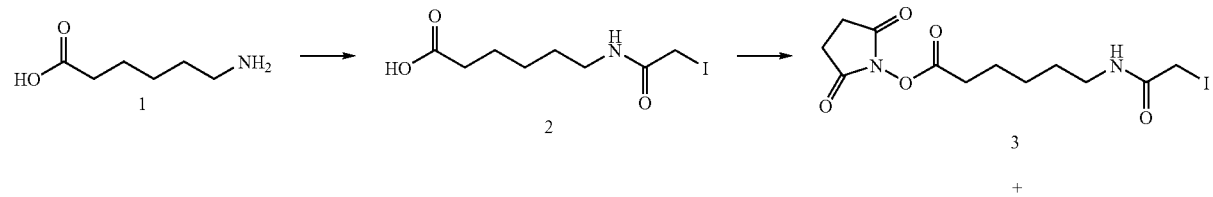

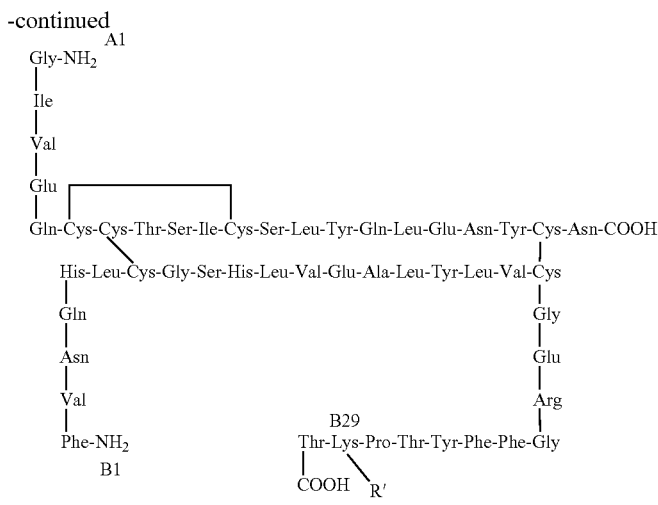

Example 1

6-(2-Iodo-acetylamino)-hexanoic acid (2)

To a suspension of 6-amino-hexanoic acid (1) (0.37 g, 2.8 mmol) in 1,4-dioxane (60 mL) was added iodoacetic anhydride (0.50 g, 1.4 mmol). The reaction mixture was stirred at 50° C. for 3 h and for 16 h at ambient temperature after which TLC analysis ($CH_2Cl_2$/MeOH/AcOH, 98/10/1, v/v/v) revealed complete conversion of compound 1 into a less lyophilic product. EtOAc (100 mL) was added and the reaction mixture was washed with 0.10 M aqueous HCl solution (50 mL). The organic layer was then washed twice with brine (50 mL) and the combined water layers were extracted twice with EtOAc (75 mL). The combined organic layers were dried ($MgSO_4$) and concentrated in vacuo. The residue was chromatographed on silica gel ($CH_2Cl_2$/MeOH/AcOH, 98/10/1, v/v/v) to give 6-(2-iodo-acetylamino)-hexanoic acid (2) (0.45 g, >100%). $^1$H NMR (MeOD): δ3.67 (s, 2H), 3.17 (t, 2H), 2.29 (t, 2H), 1.66-1.33 (m, 6H).

Example 2

6-(2-Iodo-acetylamino)-hexanoic acid 2,5-dioxo-pyrrolidin-1-yl ester (3)

To a solution of 6-(2-iodo-acetylamino)-hexanoic acid (2) (0.20 g, 0.67 mmol) in THF (10 mL) was added N-hydroxysuccinimide (85 mg, 0.74 mmol) and N,N'-dicyclohexylcarbodiimide (0.21 g, 1.0 mmol). The reaction mixture was stirred in the dark for 16 h. When TLC analysis (EtOAc/Hep/AcOH, 80/20/1, v/v/v) revealed complete conversion into the activated ester 3, seven drops of acetic acid were added. The mixture was then stored in the freezer overnight (−20° C.). The crude mixture was filtered and the filtrate was concentrated in vacuo. The crude product was purified by column chromatography (EtOAc/Hep/AcOH, 40/60/5→20/80/5, v/v/v) and concentration of the appropriate fractions gave N-hydroxysuccinimide ester derivative 3 (0.18 g, 67%). $^1$H NMR (MeOD): δ3.67 (s, 2H), 3.18 (t, 2H), 2.82 (s, 4H), 2.63 (t, 2H), 2.0-1.0 (m, 6H).

Example 3

Compound 4

To a suspension of recH insulin (50 mg, 8.6 μmol) in DMF (15 mL) was added $H_2O$ (9.0 mL) until the solution became clear. The solution was stirred for 15 min. to adjust to room temperature. The pH of the solution was adjusted to 10 by adding dropwise 0.1 M NaOH in $H_2O$. After this, the reaction flask was wrapped in tin foil. A solution of 3 (5.0 mg, 8.6 μmol) in DMF (1.0 mL) was added dropwise to the reaction mixture in 1 min. The reaction mixture was stirred by using a magnetic stirring bar and the pH was kept at 10. After 30 min an excess of 0.1% TFA in $H_2O$ (5.0 mL) was added to quench the reaction. $H_2O$ (200 mL) was added and the reaction mixture was lyophilised to give 4 (60 mg, >100%, max. 8.6 μmol). HPLC (Shimadzu, reversed phase) analysis by starting with 80% eluent A (0.1% TFA in $H_2O$) and 20% eluent B (ACN) for 5 min., then applying a gradient to 20% eluent A and 80% eluent B in 30 min. revealed the presence of 45% of the monosubstituted product (recH insulin Rt: 12.84 min; compound 4 Rt: 13.54 min; B29/A1 disubstituted product: Rt 14.16 min). The crude product was used without purification in the next reaction.

Example 4

Compound 6

Crude compound 4 (60 mg) was dissolved in a degassed (by passing through $N_2$) 0.05 M solution of $NH_2OH$ in 0.1 M $Na_2HPO_4$ buffer (25 mL, pH 7.0). The reaction mixture was stirred by using a magnetic stirring bar and degassed for 30 min (by passing through $N_2$). Then the pentasaccharide-spacer compound 5 (95 mg, 43 μmol), which was prepared as described in *Angew. Chem. Intl. Ed.* (1996), 35, 331-333, was added as a solid and the reaction mixture was stirred under a nitrogen atmosphere for 16 h.

Scheme 2. Synthesis of compound 6.
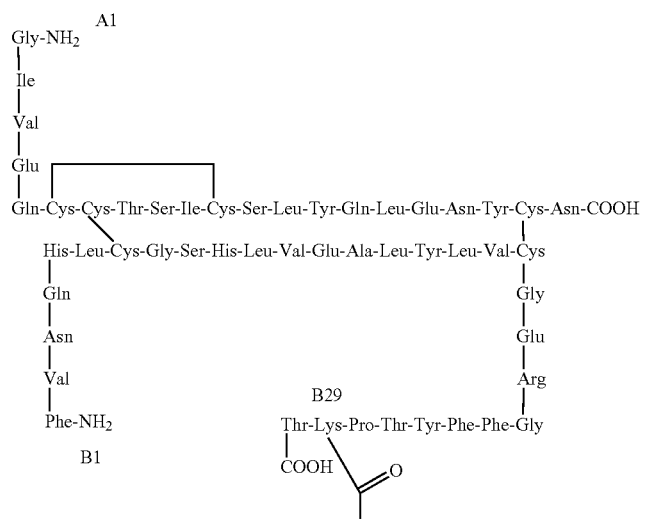
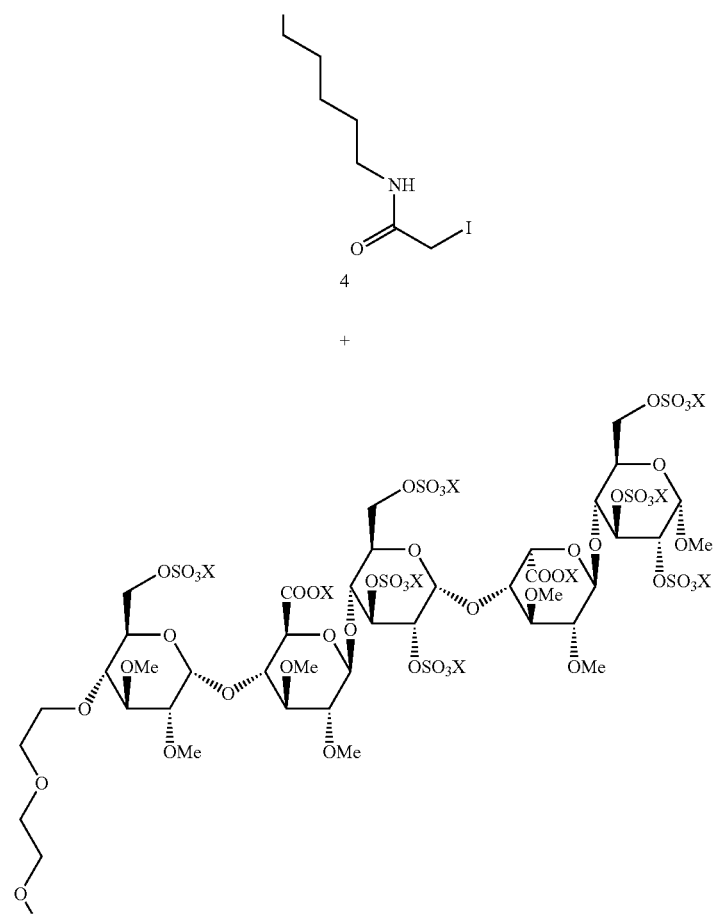

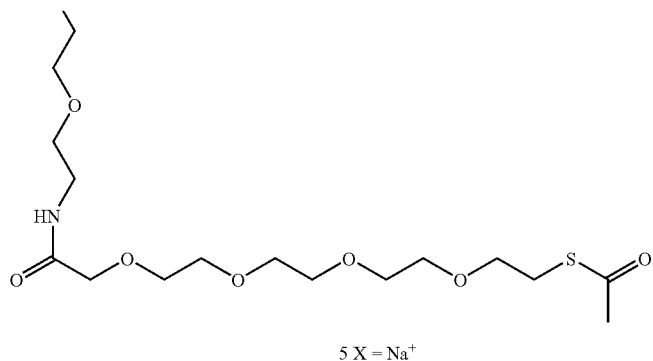
5 X = Na⁺
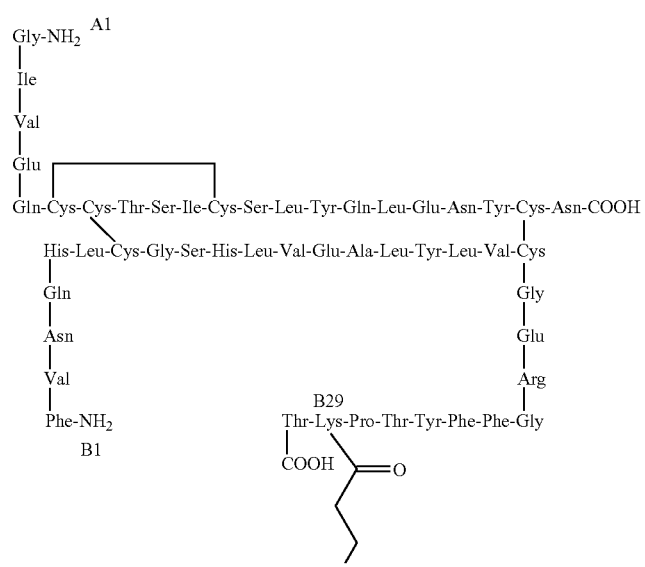
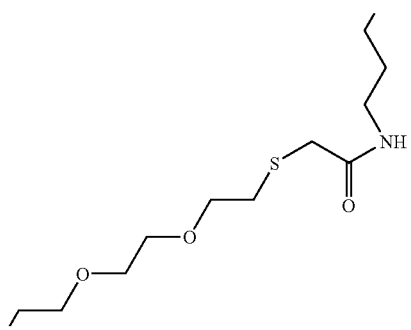

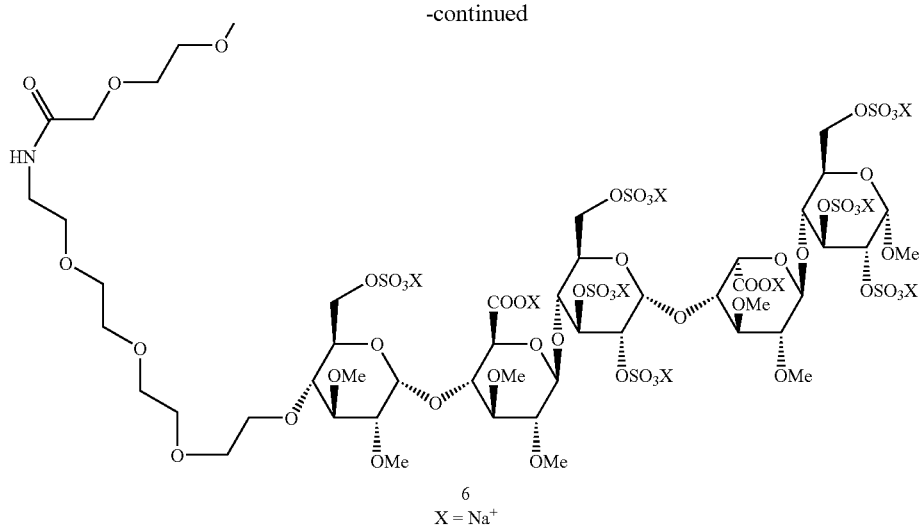

6
X = Na+

Purification of the Pentasaccharide-Insulin Conjugate 6.

From the reaction mixture of the previous paragraph, monosubstituted pentasaccharide-insulin conjugate 6 was purified to near homogeneity by anion exchange chromatography (capture step) and size exclusion chromatography (polishing step).

The conjugate-containing solution was applied on a Q-Sepharose FF column, equilibrated in 20 mmol/L sodium phosphate buffer PH 8.0. After the unretained protein fraction had passed the column, an extensive wash with equilibration buffer was carried out until the $A_{280}$ had returned to baseline level. Bound, unreacted insulin was eluted at around 0.4 mol/L NaCl and the monosubstituted pentasaccharide-insulin conjugate at 0.7 mol/L NaCl as determined by analytical HP-SEC on Superdex 30 and MALDI-TOF-MS. The conjugate fraction was concentrated either by ultrafiltration or anion exchange chromatography using a 2 mol/L NaCl bump as elution step and was applied on a preparative Superdex 30 column equilibrated in phosphate-buffered saline. Fractions containing pure monoconjugate as determined by HP-SEC and MALDI-MS were pooled. The final product was stored at −70° C. after snapfreezing in an ethanol/dry ice mixture. The conjugate concentration was estimated by $A_{280}$ measurement using an absorbance coefficient of 0.8 for 1 mg/mL.

Characterization of Compound 6

The identity of the purified pentasaccharide-insulin conjugate 6 was determined by an ELISA for insulin and by Biomolecular Interaction Analysis (BIA) using the human insulin receptor and human ATIII as analytes. Purity and monomericity were assessed by HP-SEC on Superdex 30 and MALDI-MS.

As is shown in FIG. 1, two batches of pentasaccharide-insulin conjugate 6 are recognized by the insulin-specific ELISA, which demonstrates the presence of an immunoreactive insulin moiety. From BIA experiments in the Biacore it can be concluded that pentasaccharide-conjugated insulin is still able to bind to the human insulin receptor (FIG. 2A). In these experiments a MoAb to human insulin (clone M3222213, 10-130, batch 223, Fitzgerald Industries International, designated MoAb 13) was immobilized on a CM5 sensor chip using standard amino coupling. HBS-EP (Biacore, cat. No. 22-0512-44) was used as running buffer at a flow rate of 5 μL/min. Injection of the insulin conjugate resulted in binding of the conjugate to the immobilised antibody. The immunobound insulin conjugate was able to react with the human insulin receptor as well as with ATIII, the latter being indicative for a covalently attached pentasaccharide (FIG. 2B).

MALDI-TOF spectra of the pentasaccharide-insulin conjugate 6 were obtained as described under Materials and Methods. Prior to analysis, the samples were desalted and concentrated on μC18-ZipTips (Millipore Corporation, Billerica Mass., USA). Elution was directly onto a stainless steel MALDI target in 1 μL of a solution containing 10 g/L alpha-cyano in 500 mL/L ACN/1 mL/L TFA. FIG. 3 represents a typical MALDI-TOF MS profile of a monosubstituted pentasaccharide-insulin conjugate with peaks around m/z 6700 and 7400. The apparent heterogeneity is caused by laser-induced desulfatation of the pentasaccharide moiety resulting in a serial loss of 80 Da. No disubstituted pentasaccharide-insulin conjugate was found in the MALDI-TOF MS analysis since no peaks in the range of m/z 9400 characteristic of disubstituted insulin were found. It should be noticed that also peaks for unreacted insulin are absent (m/z 5808).

HP-SEC analysis (FIG. 4) shows a major peak with a retention time of 22 min. The purity was estimated at 97%. (Unreacted insulin and disubstituted conjugate appear to be absent).

Example 5

Compound 11

Pentasaccharide 7 (46 mg) [which may be obtained by coupling of the derivatised monosaccharide 5, described in WO 2001/42262, with the tetrasaccharide that was obtained by conducting the synthetic route towards tetrasaccharide 30 described in Bioorg. Med. Chem. (1994), 2, 1267-1280 in which the reducing end monosaccharide building block 12 was replaced with methyl 2,3-di-O-benzyl-6-O-methyl-α-D-glucose, using methods similar to those described in these publications, including deprotection and sulfation] and glycol derivative 10 (18 mg, 1.6 equiv.) were dissolved in DMF (5 mL) under a nitrogen atmosphere. NMM (61 μL, 5 equiv.) was added and the reaction mixture was stirred overnight at ambient temperature. The solvent was evaporated in vacuo and the remaining residue was purified by preparative anion exchange chromatography. The appropriate fractions were combined and desalted on a preparative G25-column. The combined fractions were lyophilized to give 11 (29 mg, 57%) as a white powder. Purity >98% (analytical anion exchange, $UV_{210nm}$). $^1$H-NMR (D$_2$O, 400 MHz, HH-COSY): δ5.31 (d, 1H), 5.23 (m, 1H), 4.91 (m, 1H), 4.45-4.35 (m, 1H), 4.48-3.93 (m, 11H), 3.87-3.62 (m, 9H), 3.60-3.45 (m, 39H), 3.41-3.34 (m, 15H), 3.33-3.23 (m, 7H), 3.18-3.08 (m, 2H), 2.97 (t, 2H), 2.23 (s, 3H).

Example 6

Compound 12

Pentasaccharide 8 (0.2 g), which was prepared as described in WO 2001/42262, and glycol derivative 10 (53 mg, 1.3 equiv.), which was prepared as described in *Angew. Chem. Intl. Ed.* (1996), 35, 331-333, were dissolved in DMF (5.0 mL). NMM (61 µL, 5 equiv.) was added and the reaction mixture was stirred overnight at ambient temperature. The solvent was evaporated in vacuo and the residue was purified by preparative anion exchange chromatography. The appropriate fractions were combined and desalted on a preparative G25-column. The combined fractions were lyophilized to give 12 (0.13 g, 55%) as a white powder. Purity >95% (analytical anion exchange, $UV_{210nm}$). $^1$H-NMR ($D_2O$, 400 MHz, HH-COSY): δ5.12 (d, 1H), 5.03 (d, 1H), 4.70 (d, 1H), 4.34-4.18 (m, 2H), 4.09-4.03 (m, 1H), 3.98-3.90 (m, 5H), 3.85-3.74 (m, 6H), 3.66-3.48 (m, 7H), 3.43-3.24 (m, 41H), 3.23-3.15 (m, 13H), 3.12 (m, 2H), 3.10-3.01 (m, 7H), 2.99-2.88 (m, 3H), 2.78 (t, 2H), 2.04 (s, 3H).

Example 7

Compound 14

Pentasaccharide 9 (100 mg) [which may be obtained by coupling of the derivatised monosaccharide 5 described in WO 01/42262 with the tetrasaccharide 48 described in US 2004/0024197 using methods similar to those described in these patent applications, including deprotection and sulfation] and compound 13 (18 mg, 1.5 equiv.) were dissolved in DMF. NMM (15 µL, 2.5 equiv.) was added and the reaction mixture was stirred overnight at ambient temperature. The solvent was evaporated in vacuo and the remaining residue was purified on a preparative G25-column. The appropriate fractions were combined and lyophilized to give 14 (84 mg, 79%) as a white powder. Purity: >95% (analytical anion exchange, $UV_{210nm}$). $^1$H-NMR ($D_2O$, 400 MHz, HH-COSY): δ5.12 (d, 1H), 5.09 (d, 1H), 4.82 (d, 1H), 4.40-4.26 (m, 1H), 4.10-3.87 (m, 8H), 3.82-3.73 (m, 4H), 3.67-3.43 (m, 11H), 3.41-3.35 (m, 14H), 3.31-3.26 (m, 13H), 3.24-3.15 (m, 8H), 3.14-3.02 (m, 5H), 3.01-2.87 (m, 3H), 2.08 (s, 3H).

Scheme 3. Synthesis of pentasaccharide spacer derivatives 11, 12, and 14.

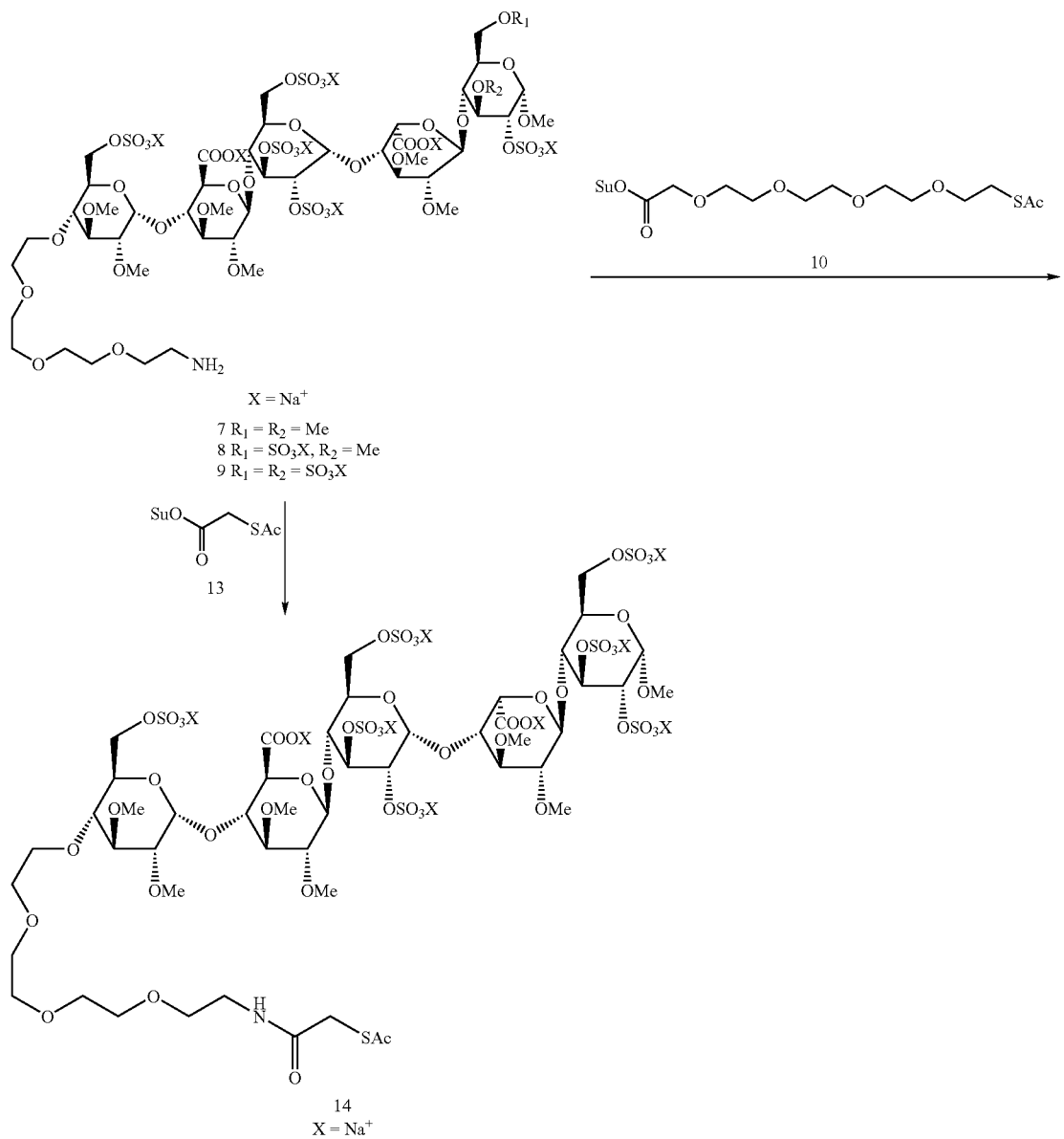

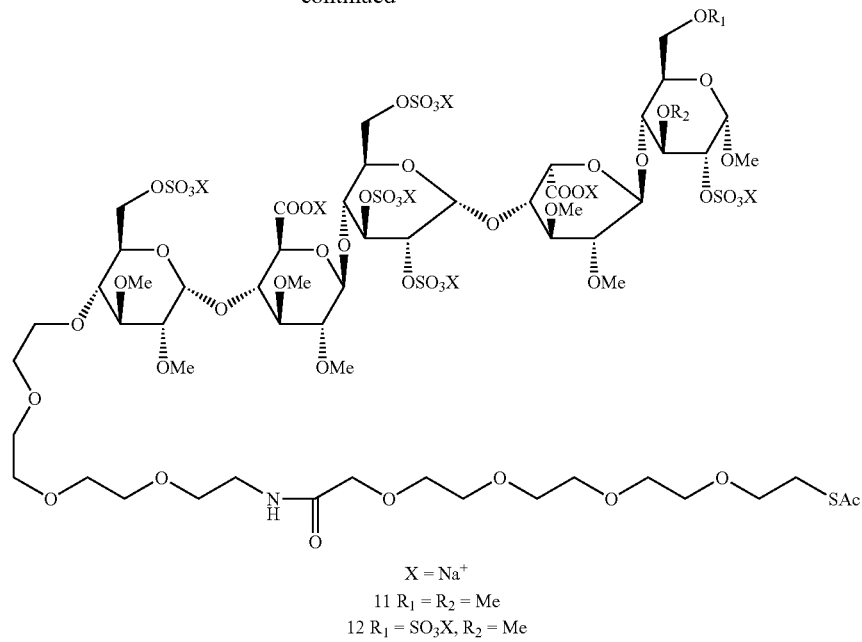

X = Na⁺
11 R$_1$ = R$_2$ = Me
12 R$_1$ = SO$_3$X, R$_2$ = Me

Example 8

Compound 15

RecH insulin (779 mg) was dissolved in anhydrous DMSO (25 mL) and AcOH (465 µL). Boc$_2$O (73 mg, 2.5 equiv) was added to the solution and the resulting mixture was stirred for 5 h at ambient temperature. The reaction was quenched by the addition of 0.1% TFA in H$_2$O/ACN (9/1, v/v, 150 mL) and the solution was lyophilized four times. The residue was dissolved in 0.1% TFA in H$_2$O/ACN (9/1)/ACN (3:1) and the main product was isolated by preparative HPLC. The appropriate fractions were combined and lyophilized to give A1,B1-diBoc insulin 15 (200 mg, 26%) as a white powder. Purity: 98% (analytical HPLC). MS calcd. for $C_{267}H_{399}N_{65}O_{81}S_6$=6008, found on MALDI-TOF 6008 (using recH insulin as internal reference standard).

Example 9

Compound 16

RecH insulin (752 mg) was dissolved in anhydrous DMSO (20 mL) and TEA (0.75 mL). Boc$_2$O (66 mg, 2.5 equiv.) in DMSO (5 mL) was added to the solution, and the reaction was stirred at ambient temperature for 1.5 h. The reaction was quenched by addition of 0.1% TFA in H$_2$O/ACN (9/1, v/v, 150 mL) and the mixture was lyophilized three times. The resulting residue was dissolved in 0.1% TFA in H$_2$O/ACN (9/1) and was subjected to preparative HPLC. The appropriate fractions were combined and lyophilized to give A1, B29-diBoc insulin 16 as a white powder (332 mg, 43%). Purity: >98% (analytical HPLC). MS calcd. for $C_{267}H_{399}N_{65}O_{81}S_6$=6008, found on MALDI-TOF 6008 (using recH insulin as internal reference standard).

Example 10

Compound 17

A1,B1-diBoc insulin 15 (200 mg) was dissolved in anhydrous dimethyl sulfoxide (5 mL) and triethylamine (145 µL). GMBS (45 mg, 5 equiv.) was added and the reaction mixture was stirred for 30 min at ambient temperature. The reaction mixture was quenched by the addition of 0.1% TFA in H$_2$O/ACN (9/1, v/v, 150 mL) and the resulting mixture was lyophilized to give A1,B1-diBoc-B29-GMB insulin 17 (0.5 g, crude), which was used in the next step without further purification.

Example 11

Compound 18

A1,B29-diBoc insulin 16 (330 mg) was dissolved in anhydrous DMSO (5 mL) and TEA (332 µL). GMBS (230 mg, 15 equiv.) was added and the reaction mixture was stirred for 30 min at ambient temperature. The reaction mixture was quenched by the addition of 0.1% TFA in H$_2$O/ACN (9/1, v/v, 150 mL) and the resulting solution was lyophilized to give A1,B29-diBoc-B1-GMB insulin 18 (0.6 g, crude), which was used in the next step without further purification.

Example 12

Compound 19

A1,B1-diBoc-B29-GMB insulin 17 (0.5 g, crude) was dissolved in TFA (5 mL) and stirred for 10 min at ambient temperature. The TFA was removed under reduced pressure, the residue was dissolved in 0.1% TFA in $H_2O$/ACN (2/1, v/v) and the solution immediately subjected to preparative HPLC. The appropriate fractions were combined and lyophilized to give B29-GMB insulin 19 as a white powder (93 mg, 47%). Purity >99% (analytical HPLC).

Example 13

Compound 20

A1,B29-diBoc-B1-GMB insulin 18 (0.6 g, crude) was dissolved in TFA (5 mL) and the mixture was stirred for 10 min at ambient temperature. The TFA was evaporated in vacuo, the crude product was dissolved in 0.1% TFA in $H_2O$/ACN (9/2, v/v) and the resulting solution was immediately subjected to preparative HPLC. The appropriate fractions were combined and lyophilized to give B1-GMB insulin 20 as a white powder (127 mg, 40%). Purity >99% analytical HPLC). MS calcd. for $C_{267}H_{399}N_{65}O_{81}S_6$=5973, found on MALDI-TOF 5973 (using recH insulin as internal reference standard).

Examples 14-19

General Procedure for the Conjugation of GMB-Insulin with Pentasaccharide

GMB-insulin 19 or 20 (25 mg) was dissolved in a 0.1 M $Na_2HPO_4$ buffer (12 mL, pH 7.0, degassed by passing $N_2$ through the solution). The solution was stirred by using a magnetic stirring bar and was degassed for another 30 min. Then pentasaccharide 5, 11, 12 or 14 (23 mg, 2.5 equiv.) was added as a solid, followed by the addition of $NH_2OH$ (50 μL, 0.05M). The reaction mixture was stirred under a nitrogen atmosphere at ambient temperature. After 16 hours the reaction mixture was subjected to preparative HPSEC (S75). The appropriate fractions were combined and lyophilized to give insulin-penta conjugates 24, 25, 26, 27, 28, 29 as a white powder in a typical yield of 30%-50%. Yields were determined by $A_{280}$ measurements using the same molar extinction coefficient as for recH insulin.

Example 14

Compound 24

B29-GMB insulin 19 (25 mg) was conjugated to pentasaccharide 5 (23 mg) according to the general procedure to give B29-pentasaccharide insulin derivative 24 (15 mg, 45%). ESI-MS calcd. for $C_{320}H_{487}N_{67}O_{137}S_{14}$=7913, found on Q-TOF 2638.7 $M^{3+}$; 1979.2 $M^{4+}$; 1583.6 $M^{5+}$; 1319.8 $M^{6+}$. Purity: >98% (analytical HPSEC, analytical anion exchange).

Example 15

Compound 25

B1-GMB insulin 20 (25 mg) was conjugated to pentasaccharide 5 (23 mg) according to the general procedure to give B1-pentasaccharide insulin derivative 25 (16 mg, 47%). ESI-MS calcd. for $C_{320}H_{487}N_{67}O_{137}S_{14}$=7913, found on Q-TOF 2637 $M^{3+}$; 1978 $M^{4+}$; 1583 $M^{5+}$. Purity: >95% (analytical HPSEC), >98% (analytical anion exchange).

Example 16

Compound 26

B29-GMB insulin 19 (13 mg) was conjugated to pentasaccharide 14 (12 mg) according to the general procedure to give B29-pentasaccharide insulin derivative 26 (5 mg, 31%). ESI-MS calcd. for $C_{312}H_{471}N_{67}O_{133}S_{14}$=7737, found on Q-TOF 2578 $M^{3+}$; 1934 $M^{4+}$. Purity: >98% (analytical HPSEC).

Example 17

Compound 27

B1-GMB insulin 20 (15 mg) was conjugated to pentasaccharide 14 (13 mg) according to the general procedure to give B1-pentasaccharide insulin derivative 27 (8 mg, 40%). ESI-MS calcd. for $C_{312}H_{471}N_{67}O_{133}S_{14}$=7737, found on Q-TOF 2578 $M^{3+}$; 1934 $M^{4+}$. Purity: >98% (analytical HPSEC).

Example 18

Compound 28

B29-GMB insulin 19 (15 mg) was conjugated to pentasaccharide 12 (13 mg) according to the general procedure to give B29-pentasaccharide insulin derivative 28 (6 mg, 30%). ESI-MS calcd. for $C_{321}H_{489}N_{67}O_{134}S_{13}$=7847, found on Q-TOF 1962 $M^{4+}$; 1570 $M^{5+}$; 1308 $M^{6+}$. HPSEC purity: >98%.

Example 19

Compound 29

B29-GMB insulin 19 (15 mg) was conjugated to pentasaccharide 11 (13 mg) according to the general procedure to give B29-pentasaccharide insulin derivative 29 (7 mg, 33%). ESI-MS calcd. for $C_{322}H_{491}N_{67}O_{131}S_{12}$=7782, found on Q-TOF 2593 $M^{3+}$; 1945 $M^{4+}$; 1556 $M^{5+}$. Purity: >98% (analytical HPSEC).

Scheme 4. Synthesis of insulin-pentasaccharide conjugates 24-29
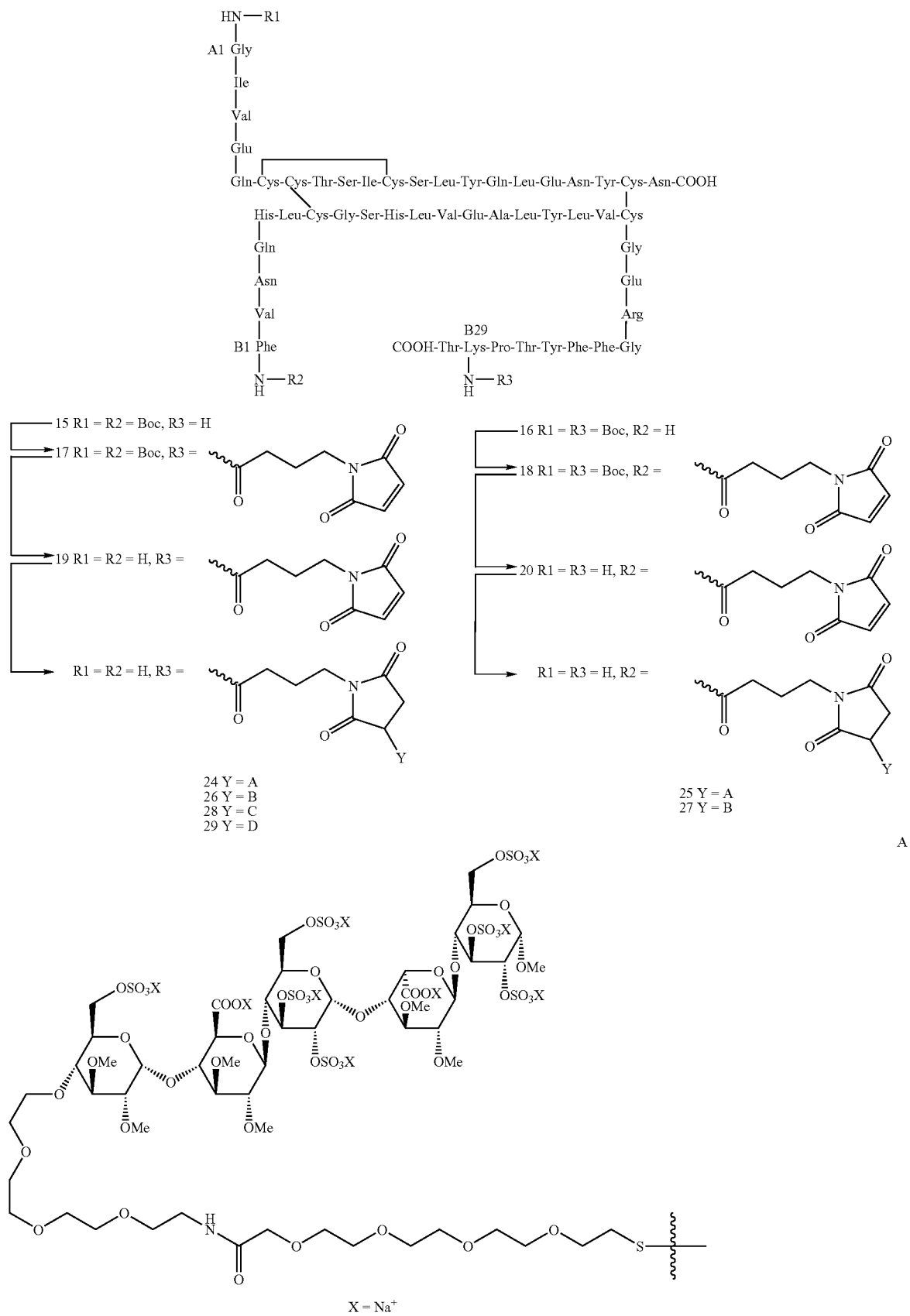

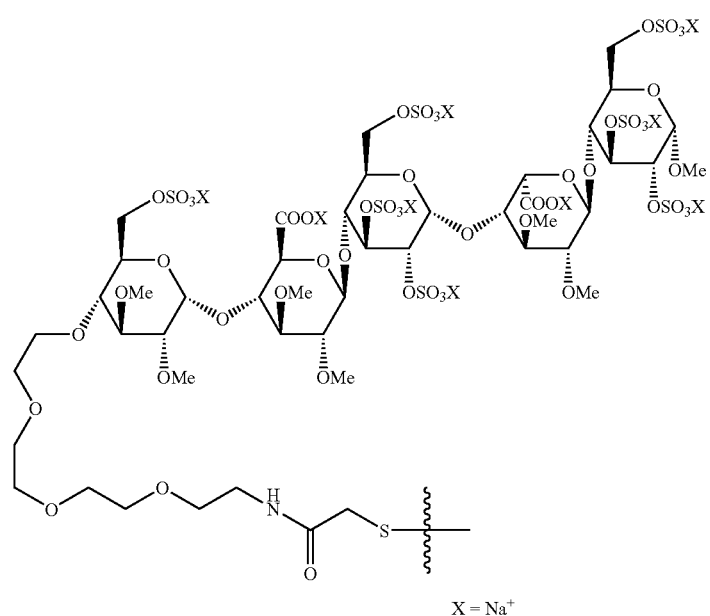
B
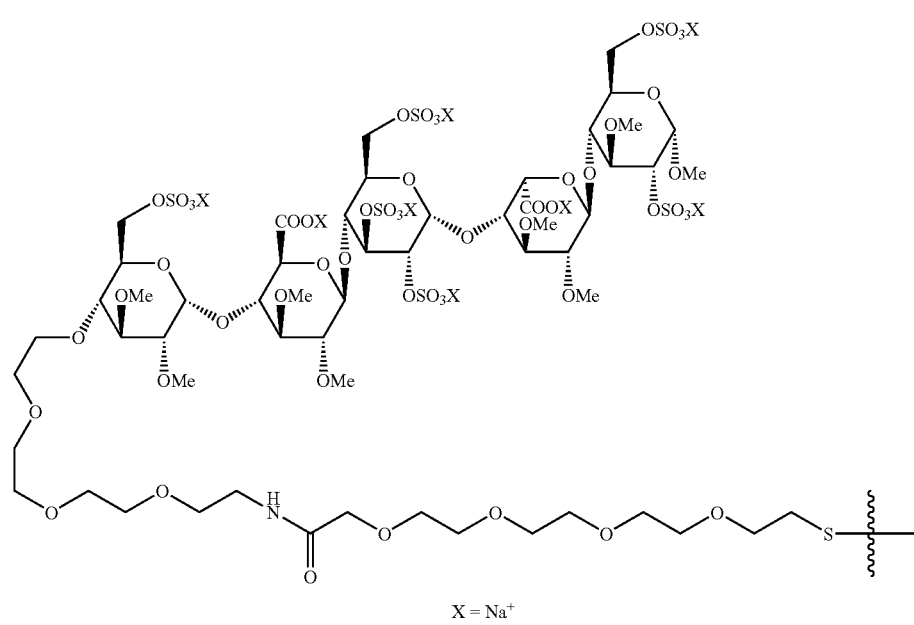
C

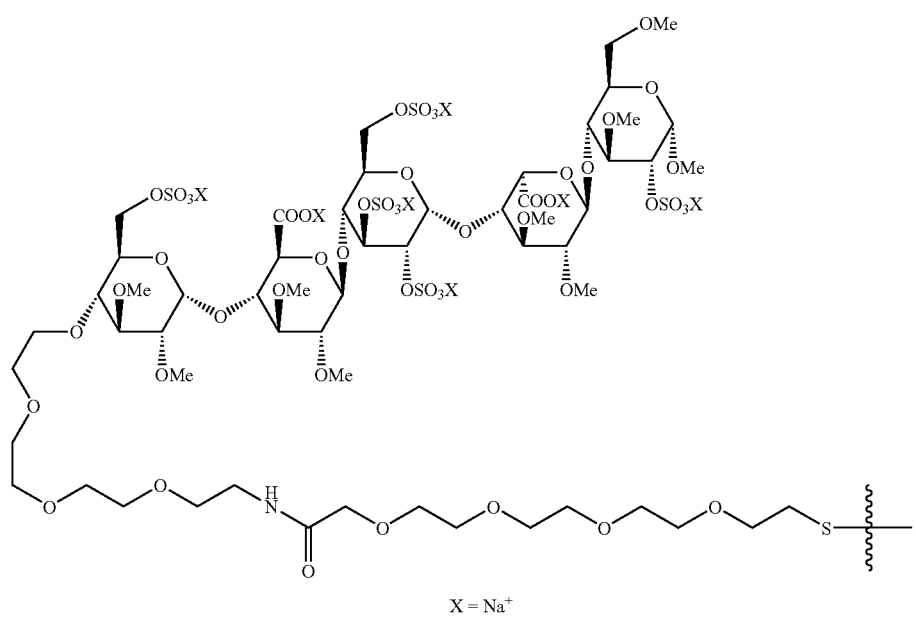

D

X = Na⁺

Characterisation

Analytical Size Exclusion Chromatography

Compounds 24-29 were subjected to analytical HP-SEC analysis on a Superdex 75 26/10 column. Elution was performed with 50 mM ammonium acetate at a flow rate of 1.0 mL/min.

TABLE 1

HPSEC analyses of insulin conjugates 24-29

| Compound | HPSEC (Superdex 75) Rt | Purity |
|---|---|---|
| 24 | 12.7 min | >98% |
| 25 | 12.5 min | >95% |
| 26 | 12.7 min | >98% |
| 27 | 12.5 min | >98% |
| 28 | 12.7 min | >98% |
| 29 | 12.8 min | >98% |
| recH insulin | 15.0 min | >98% |

All conjugates were observed as single peaks (at least >95% purity) illustrating the absence of aggregated forms of insulin-pentasaccharide.

N-Terminal Sequence Analysis

The insulin-pentasaccharide conjugates 24-29, as well as the corresponding precursors 15, 16, 19 and 20 were subjected to N-terminal sequence analysis (Edman degradation). In each of the cycles carried out, the B29 substituted insulin derivatives 15, 19, 24, 26, 28 and 29 yielded equimolar amounts of both A- and B-chain amino acids to a level comparable with that of the initial amounts of the conjugates. This indicates full accessibility of both N-termini and thus absence of conjugate moieties which are therefore confined to the B29 position. In contrast, only A chain amino acids were found during N-terminal sequencing of the B1-substituted insulin derivatives 16, 20, 25 and 27, demonstrating conjugation at the B1 position with as a consequence inhibition of Edman degradation at the N-terminus of the B-chain.

Competitive hATIII Binding Assay Using Biomolecular Interaction Analysis

Principle and aim of the test: Biomolecular Interaction Analysis (BIA) studies the interaction between (bio)molecules by covalent immobilisation of one of the interactants to a sensor chip surface, and injection of the other interactant in the continuous buffer flow over this surface. Binding is registered as a change in refractive index on this surface and is proportional to the molecular weight (Mw) of the interactants.

To study the interaction between hATIII and pentasaccharide conjugates, compound 9 is covalently coupled to the sensor chip surface. Binding of hATIII to the pentasaccharide generates a strong signal as a resultant of the difference in Mw between the bound (small) pentasaccharide ligand and the (large) hATIII analyte. Preincubated samples containing a constant concentration of hATIII and variable concentrations of free pentasaccharide or conjugate were injected over the surface. Binding of pentasaccharide or conjugate to ATIII during preincubation will result in a reduction of ATIII binding to the immobilised pentasaccharide. This competitive binding assay allows determination of $IC_{50}$ values for each pentasaccharide conjugate.

Experimental procedure: Compound 9 is covalently coupled to a CM5 sensor chip by amine coupling at pH 8.5. The sensor chip is activated by EDC/NHS for 15 min. and subsequently compound 9 is injected at a concentration of 100 µg/mL. The unreacted hydroxysuccinimide groups are reacted with ethanolamine for 7 min. The surface is regenerated by three short injections of 5 µL 5 mol/L NaCl, at a flow rate of 25 µL/min. Immobilisation of the pentasaccharide can not be detected, however, binding of hATIII to a surface treated as described was found specific, demonstrating the presence of pentasaccharide on the surface.

A concentration series of hATIII was tested to estimate a sensitive concentration for inhibition (at 80% of maximum binding). At a flow rate of 20 µL/min three minute injections were carried out at both blanc and immobilised surface in series at 25° C. A report point is generated at 170 s. The surface is regenerated by a 12 s injection of 5 mol/L NaCl.

The samples were tested against a constant concentration of hATIII (i.e. 15 nmol/L) and concentrations of pentasaccharide conjugate ranging between 0.78-100 nM. The hATIII injection or report point without pentasaccharide conjugate is set at 100% binding. The relative % binding of the pentasaccharides and the conjugates compared to maximum binding was used to generate a sigmoidal curve (with variable slope) by plotting Log [concentration] vs. % binding from which the $IC_{50}$ values were derived.

TABLE 2

$IC_{50}$ values expressing ATIII binding potential in a competitive binding assay (BIA study)

| Compound | BIA (competitive ATIII binding) | |
|---|---|---|
| | $IC_{50}$ | 95% confidence interval |
| 7 (reference) | 96 nM | 53.1-173 nM |
| 8 (reference) | 58 nM | 33.7-99.1 nM |
| 9 (reference) | 5.5 nM | 5.1-5.8 nM |
| 24 | 8.5 nM | 7.9-9.3 nM |
| 25 | 9.1 nM | 8.2-10.0 nM |
| 26 | 4.5 nM | 4.2-4.7 nM |
| 27 | 15 nM | 13.3-17.0 nM |
| 28 | 96 nM | 50.6-183 nM |
| 29 | 68 nM | 33.9-137 nM |

Conclusion—The difference in $IC_{50}$'s between the reference carrier pentasaccharides 7-9 (FIG. 5, Table 2) confirms that their competitive binding potential to ATIII, a measure for the binding affinity for ATIII, can be tuned by changing the number of sulfate groups contained in these molecules. The (competitive) binding potential ($IC_{50}$) of all corresponding insulin-pentasaccharide conjugates (24-29) to hATIII fall in the same range when compared to the parent reference pentasaccharides 7-9 (FIG. 6, Table 2). These data indicate that the pharmacokinetic properties of the conjugates may be tuned by using alternative carrier pentasaccharides with different binding affinity for ATIII.

Mass Spectrometry

A typical mass spectrometric analysis of a pentasaccharide conjugate is depicted in FIG. 7. For instance, compound 24 with the bruto formula $C_{320}H_{487}N_{67}O_{137}S_{14}$ and a calculated mono isotopic mass of 7913, has been analysed with an ESI-QTOF system. In the ESI-MS spectrum multiple charged ions at m/z ratios 1319.8 (6+), 1583.6 (5+), 1979.2 (4+), 2638.7 (3+) in line with the charge distribution of recH insulin have been encountered. In addition, the isotope distribution of a randomly selected multiple charged peak (e.g. 5+) for $C_{320}H_{487}N_{67}O_{137}S_{14}$ (compound 24) is in agreement with the theoretically calculated isotope distribution with the programme Isopro (see dotted lines in FIG. 7A).

General Procedure for the Conjugation of GnRH Antagonistic Decapeptides with Pentasaccharide Examples 20, 21, 24, 25

Ganirelix-derivative 30 or 35 (70 mg) was dissolved in DMF (20 mL) under a nitrogen atmosphere. TBTU (14 mg, 1.05 equiv.) and NMM (25 µL, 5 equiv.) were added and the mixture was stirred for 1 hour at ambient temperature. Pentasaccharide 8 or 9 (88 mg, 1.1 equiv.) was dissolved in DMF (10 mL) to give a suspension. This suspension was added to the reaction mixture and the remaining mixture was stirred for 16 hours at ambient temperature. The reaction mixture was diluted with water (200 mL) and was lyophilized. The resulting residue was purified on reversed phase silica (C18) with 0.01 M ammonium acetate (pH 7) and a gradient of 10 to 50% ACN in block-elutions. The appropriate fractions were combined and lyophilized to give the ganirelix pentasaccharide conjugate 31, 32, 36 or 37 as a white powder. Analytical HPLC was performed with a gradient elution by starting with 90% eluent A (0.01M ammonium acetate) and 10% eluent B (ACN) for 5 min., then applying a gradient to 100% eluent B in 30 min.

Example 20

Compound 31

Ganirelix-derivative 30 (70 mg), which was prepared by solid phase peptide synthesis as described in *J. Med. Chem.* 1992, 35, 3942-3948, was conjugated to pentasaccharide 8

(88 mg) according to the general procedure to give 31 (16 mg, 40%). Purity 96% (analytical HPLC), 97% (analytical anion exchange). ESI-MS calcd. for $C_{126}H_{191}ClN_{18}O_{62}S_6=$ 3175.0359, found 792.7390 $[M-4H]^{4-}$, 1057.3258 $[M-3H]^{3-}$, 1062.9883 $[M+NH_3-3H]^{3-}$. $^1$H-NMR ($D_2O$, 400 MHz, HH-COSY): δ8.56 (m, 1H), 8.53 (m, 1H), 8.10 (m, 1H), 7.76 (m, 2H), 7.68 (m, 2H), 7.47 (m, 1H), 7.39 (m, 2H), 7.16 (m, 3H), 7.04 (m, 2H), 6.95 (m, 2H), 6.63 (m, 2H), 5.35-5.25 (m, 2H), 4.95 (m, 1H), 4.68-4.61 (m, 1H), 4.61-4.51 (m, 2H), 4.50-4.38 (m, 2H), 4.38-4.25 (m, 3H), 4.24-3.96 (m, 15H), 3.90-3.84 (m, 1H), 3.84-3.67 (m, 8H), 3.67-3.20 (m, 53H), 3.19-3.09 (m, 4H), 3.09-2.98 (m, 12H), 2.98-2.84 (m, 8H), 2.77 (m, 2H), 2.13 (m, 1H), 1.96-1.72 (m, 5H), 1.68-1.42 (m, 5H), 1.42-1.20 (m, 7H), 1.18-0.89 (m, 13H), 0.85-0.71 (m, 5H).

Example 21

Compound 32

Ganirelix-derivative 30 (70 mg) was conjugated to pentasaccharide 9 (88 mg) according to the general procedure to give 32 (52 mg, 35%). Mass calcd. for $C_{125}H_{189}ClN_{18}O_{65}S_7=$ 3240.9770; found on ESI-QTOF 809.2219 $[M-4H]^{4-}$, 1079.2994 $[M-3H]^{3-}$, 1084.9739 $[M+NH_3]^{3-}$, 1090.6340, $[M+2NH_3-3H]^{3-}$. $^1$H-NMR ($D_2O$, 400 MHz, HH-COSY): δ8.45 (m, 1H), 8.38 (m, 1H), 7.90 (m, 1H), 7.78 (d, 1H), 7.73 (m, 2H), 7.59 (m, 1H), 7.50 (m, 1H), 7.43 (m, 2H), 7.20 (m, 3H), 7.05 (d, 2H), 6.97 (m, 2H), 6.66 (m, 2H), 5.40-5.30 (m, 2H), 5.09 (d, 1H), 4.67-4.48 (m, 2H), 4.40-3.92 (m, 18H), 3.92-3.75 (m, 7H), 3.77-3.17 (m, 56H), 3.12-3.02 (m, 11H), 3.02-2.98 (m, 8H), 2.97-2.83 (m, 4H), 2.81-2.75 (m, 2H), 2.14 (m, 1H), 1.99-1.86 (m, 5H), 1.82-1.23 (m, 12H), 1.22-0.90 (m, 13H), 0.87-0.72 (m, 5H). Purity: 95% (analytical HPLC), 97% (analytical anion exchange purity).

Example 22

Compound 34

Compound 30 (100 mg) was dissolved in DMF. TBTU (36 mg, 2 equiv.) and NMM (60 μL, 10 equiv.) were added and the reaction mixture was stirred for 1 hour at ambient temperature. Then compound 33 (34 mg, 2 equiv.), which was prepared as described in WO 2005090382, was added and the reaction mixture was stirred for 16 hours at ambient temperature. The solvent was removed in vacuo and the remaining residue was dissolved in water/CAN, the resulting solution which was subjected to preparative HPLC (gradient: 80% eluent A (0.1% TFA in $H_2O$) and 20% eluent B (ACN) to 20% eluent A and 80% eluent B in 45 min.). The appropriate fractions were combined to give, after lyophilization, compound 34 (60 mg, 60%) as a white powder. Analytical HPLC was performed by applying a gradient starting with 75% eluent A (0.1% TFA in $H_2O$) and 25% eluent B ($CH_3CN$) to 20% eluent A and 80% eluent B in 15 min. Mass calcd. for $C_{94}H_{139}ClN_{18}O_{19}=1859$, found on MALDI-TOF 1860 $[M+H]^+$ and 1882 $[M+Na]^+$. Purity: >90% (analytical HPLC).

Example 23

Compound 35

Compound 34 (60 mg) was dissolved in $H_2O$/TFA/ACN (7 mL, 5:1:1) and was stirred for 2 hours at ambient temperature. An extra amount of TFA (2.5 mL) was added and the reaction mixture was stirred for another 22 hours. The TFA was evaporated in vacuo and the remaining solution was lyophilized to give 35 (45 mg, 77%) as a white powder. Mass calcd. for $C_{90}H_{131}ClN_{18}O_{19}=1803$, found on MALDI-TOF 1804 $[M+H]^+$ and 1826 $[M+Na]^+$. Purity: >95% (analytical HPLC).

Example 24

Compound 36

Ganirelix-derivative 35 (17 mg) was conjugated to pentasaccharide 8 (19 mg) according to the general procedure. Additional purification was performed by preparative HPLC (gradient: 90% eluent A (0.01 M ammonium acetate) and 10% eluent B ($CH_3CN$) for 5 min., then to 100% B in 50 min.). The appropriate fractions were combined and lyophilized to give 36 (2 mg, 6%). Purity: 94% (analytical HPLC), >98% (analytical anion exchange).

Example 25

Compound 37

Ganirelix-derivative 35 (17 mg) was conjugated to pentasaccharide 9 (19 mg) according to the general procedure. Additional purification was performed by preparative HPLC as described for compound 36. The appropriate fractions were combined and lyophilized to give 37 (1.16 mg, 3%). Purity: 88% (analytical HPLC). Analytical anion exchange purity: >95%.

Scheme 5. Synthesis of compounds 31, 32, 36 and 37.
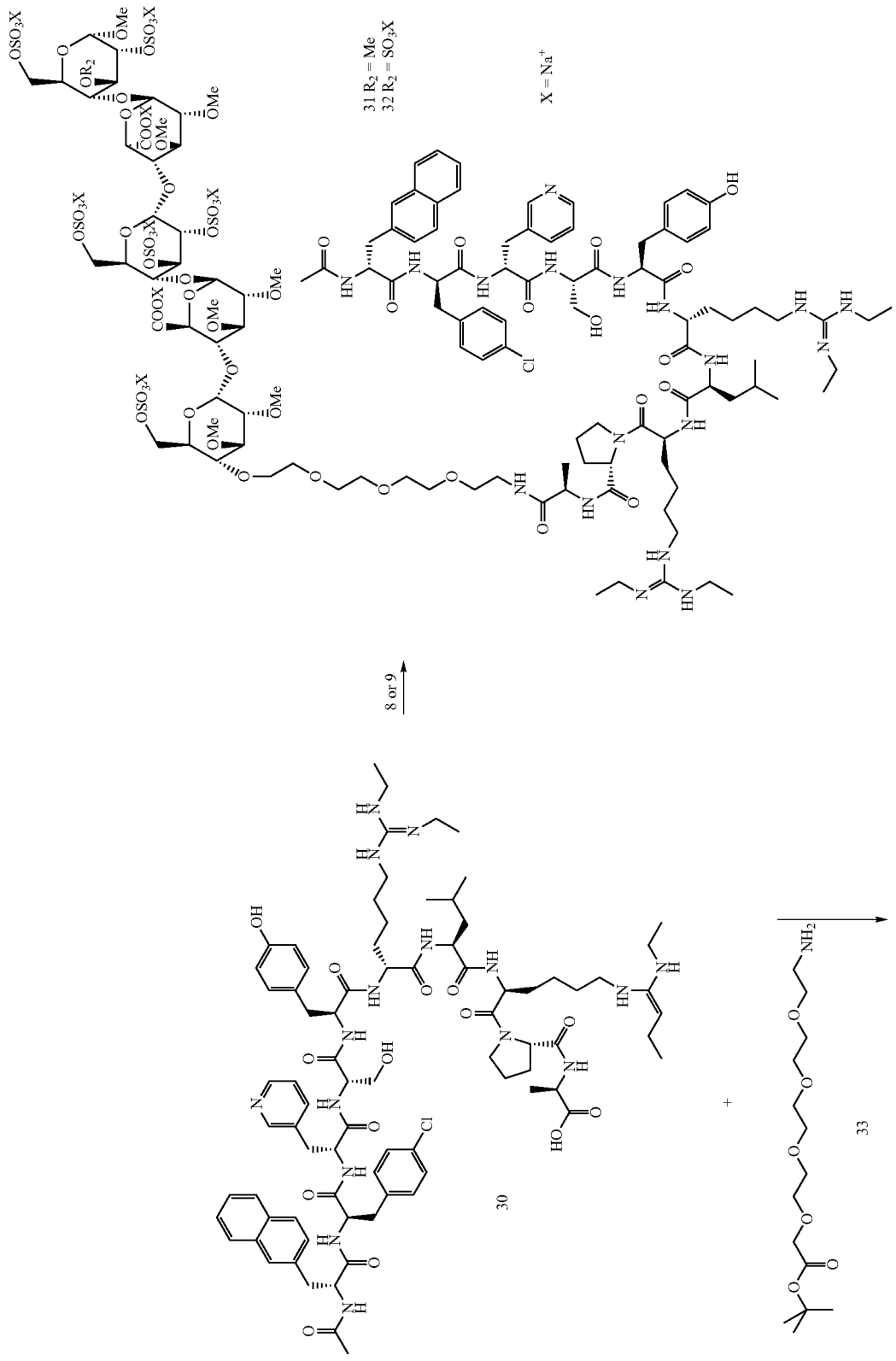

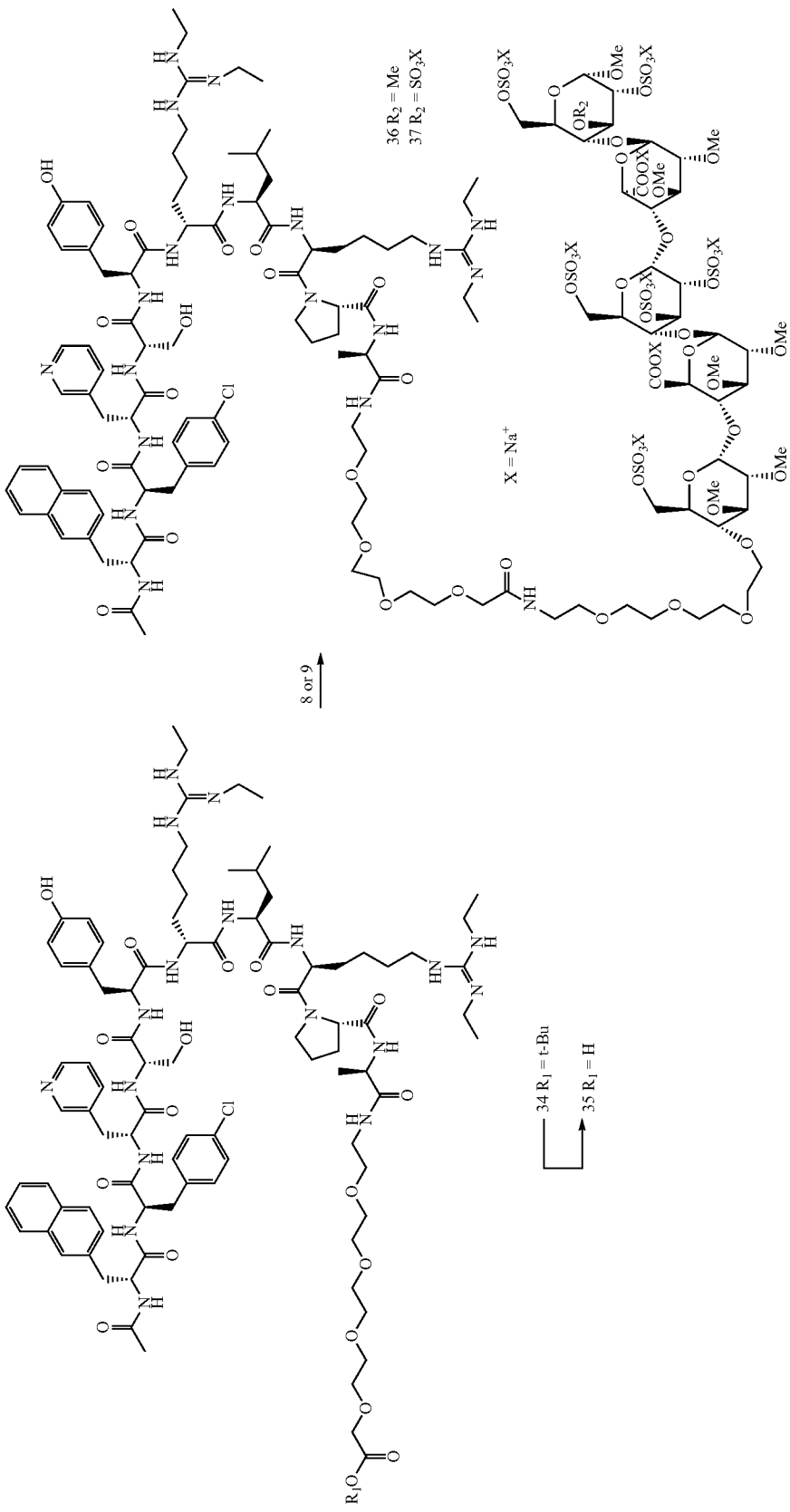

Conclusion: The differences in competitive binding potential to ATIII between on the one hand conjugates 31 and 32, and on the other hand conjugates 36 and 37 (as depicted in FIG. 8) reveal that, irrespective of the length of the linking residue, the affinity for ATIII can be tuned by changing the number of sulfate groups contained in these molecules. These data further indicate that the in-vivo pharmacokinetic properties of these conjugates may be tunable by the choice of the pentasaccharide (see pharmacokinetic study below). Furthermore, the binding of the conjugates to ATIII is specific, since the non-conjugated parent peptide ganirelix shows no competitive binding to ATIII.

Example 24

Compound 39

Compound 38 (26.5 mg, 8.4 μmol), supplied by NeoMPS (Strasbourg, France), was dissolved in degassed 0.1 M Na$_2$HPO$_4$/NaH$_2$PO$_4$ buffer (16 mL, pH 7.0). Pentasaccharide 5 (45.5 mg, 21 μmol, 2.5 equiv.) was added under a nitrogen atmosphere and the resulting mixture was stirred for approximately 10 min. Then an aqueous solution of NH$_2$OH (50 wt %, 69 μL) was added and the reaction mixture was stirred for 16 h. The product was purified on a Q-Sepharose column (2M NaCl$_{(aq)}$/H$_2$O/ACN, 10/40/1→40/10/1, v/v/v). Desalting of the appropriate fractions was carried out using G25 sephadex chromatography as described above to yield compound 39 (15.7 mg, 35%). The yield was determined by A$_{280}$ measurement using a theoretical absorbance of 0.48 for a 1 mg/mL solution. Calcd. mass for C$_{196}$H$_{309}$N$_{41}$O$_{101}$S$_8$= 5108.8; found on ESI-Q-TOF=1740.6 [M+5Na]$^{3+}$, 1311.2 [M−1H+6Na]$^{4+}$, 1053.5 [M−2H+7Na]$^{5+}$ Scheme 6. Synthesis of compound 39

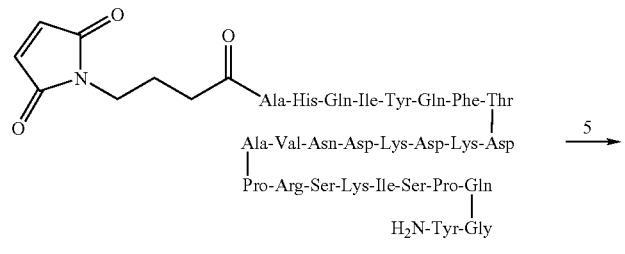

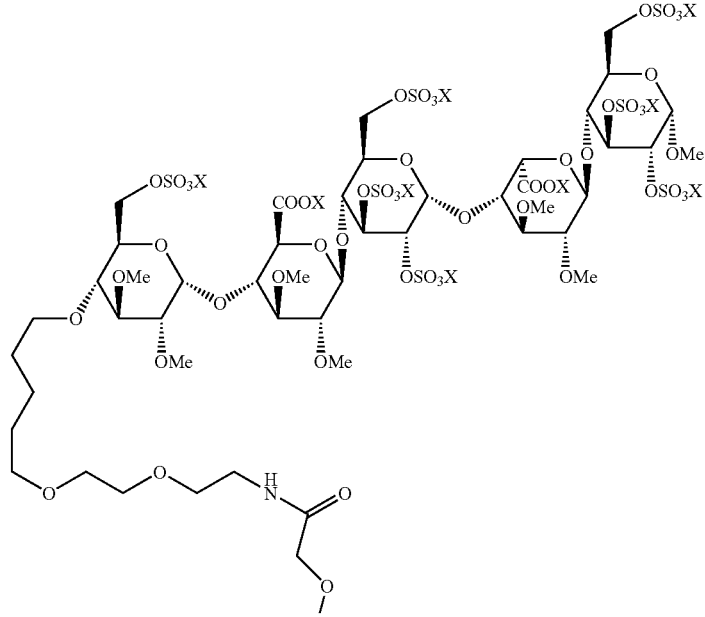

-continued

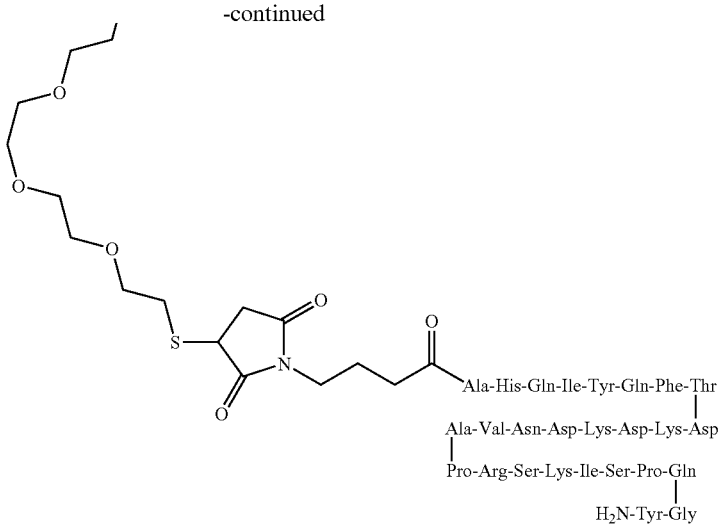

39

Conclusion: As depicted in FIG. 9 the competitive binding potential to ATIII of conjugate 39 is conserved when compared to the parent pentasaccharide-spacer residue (see FIG. 5, compound 9). These data suggest that a significant extension of the in-vivo half-life of the peptide can be achieved by conjugation to an ATIII binding carrier pentasaccharide (see pharmacokinetic study below). Furthermore, the binding of the conjugate to ATIII is specific, since the non-conjugated parent peptide ADM(27-52) shows no significant competitive binding to ATIII.

Example 25

Compound 41

Compound 40 (15 mg, 4.2 µmol), prepared by NeoMPS (Strasbourg, France), was dissolved in degassed 0.1 M $Na_2HPO_4/NaH_2PO_4$ buffer (8 mL, pH 7.0). Pentasaccharide 5 (22.7 mg, 10.4 µmol, 2.5 equiv.) was added under a nitrogen atmosphere and the mixture was stirred for approximately 10 min. Then an aqueous solution of $NH_2OH$ (50 wt %, 0.14 mL) was added and the reaction mixture was stirred for 16 h. The product was purified as described for compound 39 to yield compound 41 (1.38 mg, 6%). The yield was determined by $A_{280}$ measurement using a theoretical absorbance of 1.22 for a 1 mg/mL solution. Mass calcd. for $C_{218}H_{342}N_{44}O_{106}S_8=$ 5528; found on ESI Q-TOF=1843.7 $[M+3H]^{3+}$, 1383.0 $[M+4H]^{4+}$, 1107 $M+5H]^{5+}$.

Conclusion: The competitive binding potential to ATIII of conjugate 41 is conserved when compared to the parent pentasaccharide-spacer residue compound 9 (see FIG. 10). These data suggest that a significant extension of in-vivo half-life of the peptide may be attained by conjugation to an ATIII binding carrier pentasaccharide (see pharmacokinetic study below).

Scheme 7. Synthesis of compound 41

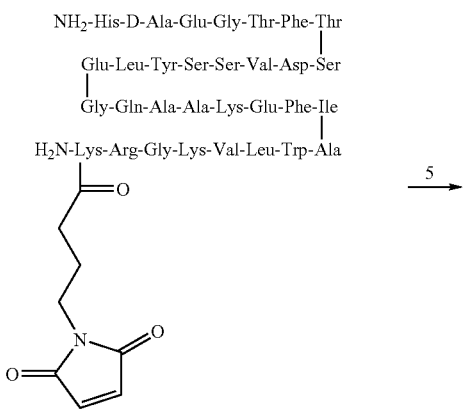

40

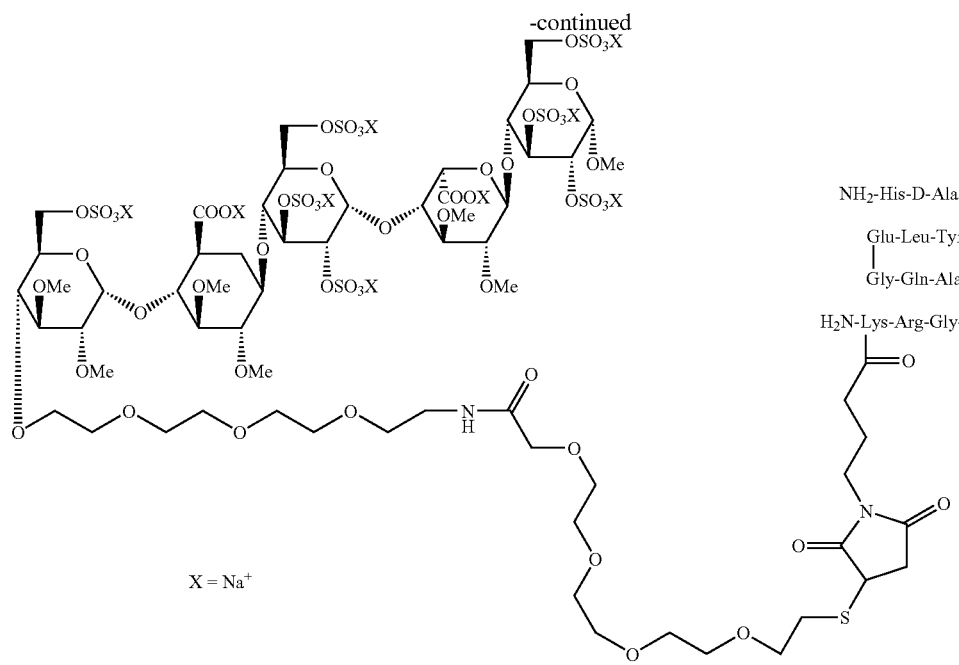

41

Example 26

Compound 44

Octreotide (compound 42, 50 mg, 0.04 mmol), which can be by obtained at commercial suppliers such as Bachem (Weil am Rhein, Germany), was dissolved in DMSO (5 mL). AcOH (7 μL) was added to generate a slightly acidic solution. Subsequently GMBS (11.2 mg, 0.04 mmol, 1.0 equiv.) was added and the resulting solution was stirred under nitrogen for 1 h. LC-MS analysis showed a near complete conversion to GMB octreotide 43 in which the GMB moiety is introduced to the N-terminal Phe residue in a highly regioselective manner. The reaction was cooled to ~5° C. after which a solution of $NaH_2PO_4/Na_2HPO_4$ (20 mL, pH 7.0) was added. After 10 min. the mixture was allowed to reach to RT and $N_2$ was lead through the solution for 10 min. Then pentasaccharide 5 (21.8 mg, 0.01 mmol, 0.25 equiv.) was added as a solid under a nitrogen atmosphere, followed by an aqueous solution of $NH_2OH$ (0.11 mL, 50 wt %) and the reaction mixture was stirred for 16 h. The product was purified by ion exchange chromatography as described above, to yield compound 44 (6.3 mg, 19%). Mass calcd. for $C_{112}H_{170}N_{12}O_{70}S_{10}$=3122.7; found on ESI-Q-TOF=1562.3 $[M+2H]^{2+}$, 1041.9 $[M+3H]^{3+}$. 1H-NMR ($D_2O$, 400 MHz, HH-COSY): δ7.52-7.29 (m, 10H), 7.26-7.14 (m, 4H), 7.03 (s, 1H), 5.44 (m, 1H), 5.37 (m, 1H), 5.14 (m, 1H), 5.12-4.89 (m, 2H), 4.77-4.60 (m, 3H), 4.45-3.97 (m, 18H), 3.95-3.76 (m, 13H) 3.75-3.35 (m, 57H), 3.33-2.59 (m, 18H), 2.22-1.16 (m, 2H), 1.85-1.76 (m, 3H), 1.71-1.38 (m, 3H), 1.32-1.15 (m, 7H), 0.81-0.61 (M, 2H).

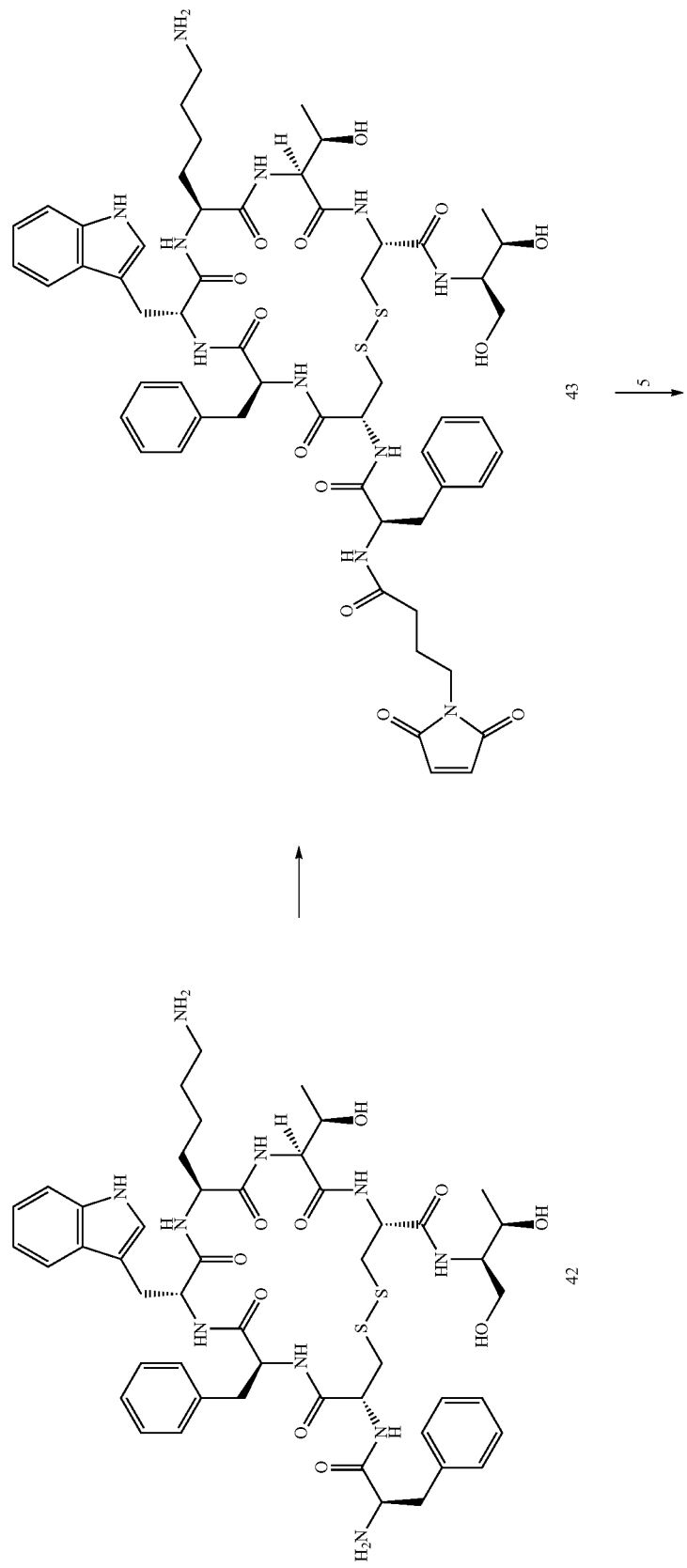
Scheme 8. Synthesis of compound 44

-continued
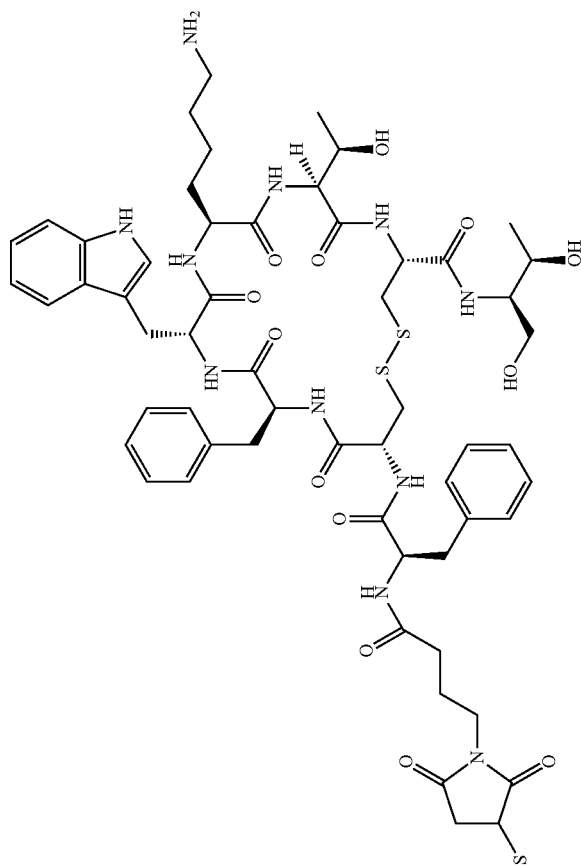
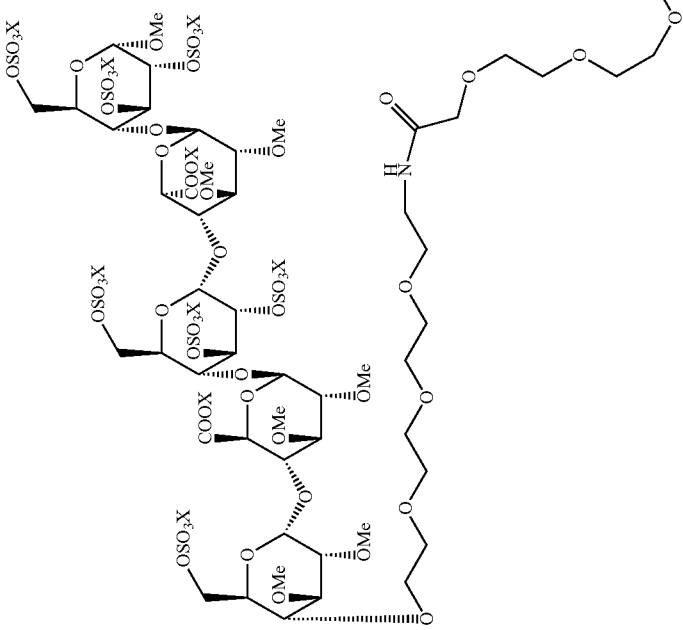

Conclusion: The competitive binding potential to ATIII of conjugate 44 is conserved when compared to the parent pentasaccharide-spacer residue compound 9 (see FIG. 11). These data are indicative for a significant extension of in-vivo half-life of the peptide by conjugation to an ATIII binding carrier pentasaccharide.

Example 27

Compound 46

Pentasaccharide 9 (100 mg) and GMBS (22 mg, 1.5 equiv.) were dissolved in DMF (10 mL). DiPEA (18 µL, 2 equiv.) was added and the reaction mixture was stirred overnight at ambient temperature. The solvent was evaporated in vacuo and the residue was purified on a preparative G25-column. The combined fractions were lyophilized to give 46 (50 mg, 46%) as a white powder. ESI-MS calcd. for $C_{53}H_{77}N_2O_{55}S_7Na_9$=2052; found on ESI-Q-TOF=1027 $M^{2+}$.

Example 28

Compound 47

Pentasaccharide maleimide derivative 46 was conjugated to the free $Cys^{125}$ of native recH-IL2 (R&D systems, 202-IL/CF). Prior to conjugation recH-IL-2 was analysed by HPSEC, SDS-PAGE and MALDI-TOF MS indicating a predominant monomeric composition. RecH-IL2 (1 mg, 800 µL, 1.26 mg/mL in PBS containing 0.5% SDS) was treated overnight at RT on a roller bank with an excess of compound 46 (59 µL of a 10 mg/mL aq. solution, 5 equiv.) to achieve complete conversion of starting material. Next, unreacted maleimide 46 was blocked with a 5 times molar excess of cysteamine (16 µL, 10 mg/mL) for 3 h. The reaction mixture was dialysed (cut off 6-8 kDa) against 0.5% SDS in PBS to remove excess cysteamine and 46 and the final amount of product as determined by $A_{280}$ was 0.69 mg.

The final conjugate 47 was characterized by SDS-PAGE (4-12%) and Western blot (see FIG. 12). From lanes 3 and 4 it is concluded that compound 47 has a higher Mw relative to recH-IL2 (corresponding to the presence of a pentasaccharide moiety). Western blot analysis with subsequent incubations of a) 10 µg/mL hATIII (HAT 950A2L—Kordia); b) a-hATIII (MoAb HATIII 200—Kordia); c) GAM-HRP (W402B 20373201—Promega) and final detection with DAB reagent clearly revealed specific ATIII binding to pentasaccharide-containing IL2 (lane 7 vs. 8).

Scheme 9. Synthesis of conjugate 47

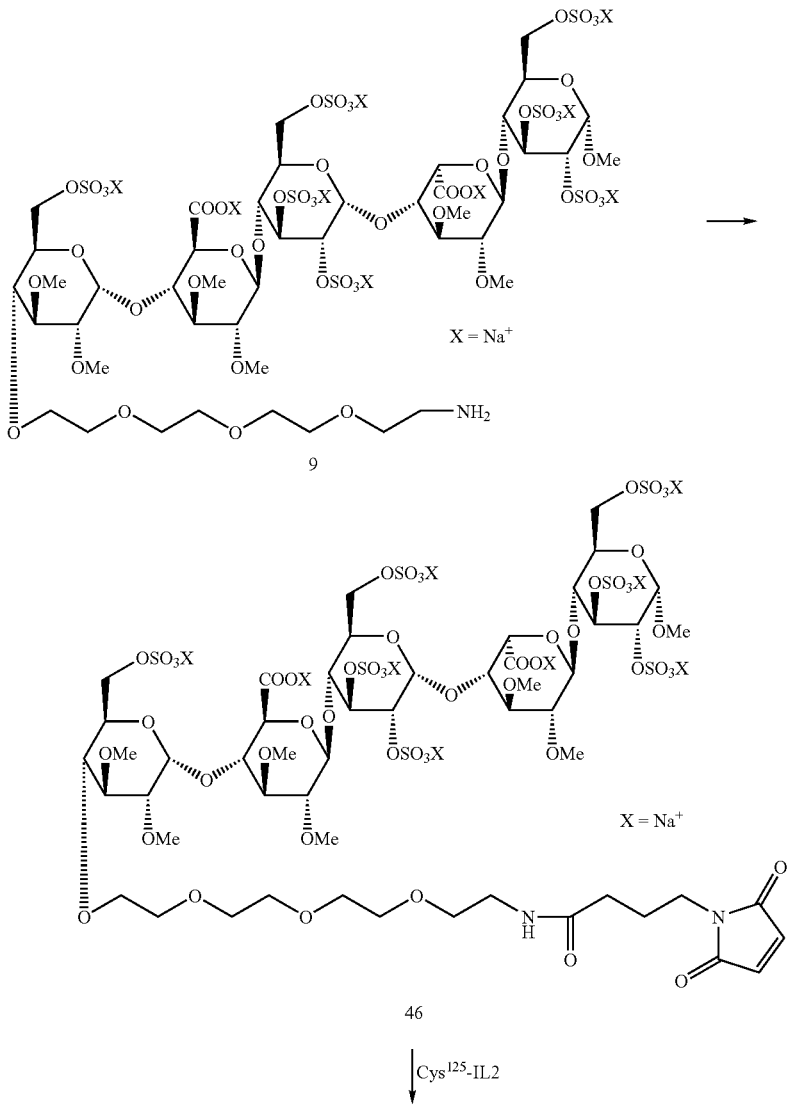

-continued

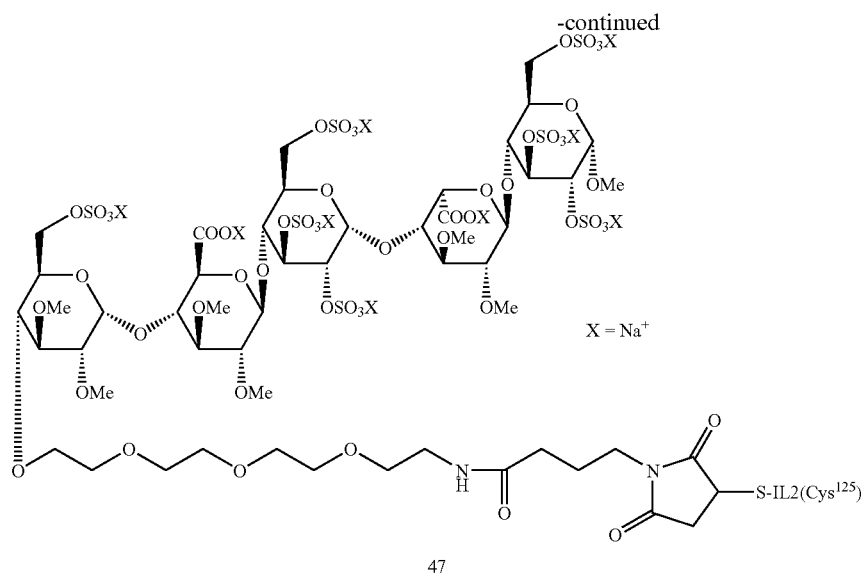

47

Pharmacology
Determination of Pharmacokinetics of Conjugated (Poly) Peptides

The pharmacokinetic properties of representative examples of compounds of the invention were determined as described in the following paragraphs.

Human Insulin ELISA for Determination of Insulin in Rat Plasma

The human Enzyme-Linked Immuno-Sorbent Assay (ELISA) has been developed to measure human insulin in human and rat plasma or buffer system. In this way the ELISA could be used to determine the insulin concentration in plasma samples derived from pharmacokinetic experiments.

The assay is based on the immunochemical "sandwich" principle using two monoclonal antibodies, i.e. a solid phase bound, capture antibody and a detection antibody which is labeled with horseradish peroxidase (HRP).

For the determination of the pharmacokinetic properties of pentasaccharide-insulin conjugate 6 and recombinant human insulin (recH insulin, batch SIHR017, from Diosynth, The Netherlands), rat plasma samples were incubated for 1 h at room temperature, while shaking at 10 Hz. During this incubation, pentasaccharide-insulin conjugate 6 or recH insulin binds to the immobilized anti-insulin antibody. After a second washing procedure, detection antibody anti-insulin conjugated with HRP was added to bind to the immobilized insulin-complex. The plate was washed to remove unbound enzyme-labeled antibody and subsequently the 3,3',5,5'-tetramethylbenzidine/$H_2O_2$ substrate solution was added. The reaction was stopped with 0.5 M sulphuric acid and the microtiter plate was read spectrophotometrically at 450 nm. The intensity of colour is directly proportional to the concentration of insulin. Then for each plasma sample the mean concentration (mol/L) of insulin was determined.

Determination of Pharmacokinetic Properties of Compound 6

The pharmacokinetic behavior of insulin conjugate 6 and recH insulin were studied in male Wistar rats of 300-400 gr. The rats were anaesthetized by inhalation of a mixture of $O_2/N_2O$/isoflurane, after which the right jugular vein was cannulated. The next day rats were treated i.v. with doses of 3.5 nmol/kg of compound 6 or recH insulin, after which blood was sampled at several time intervals. Blood was centrifuged after which the plasma was siphoned off and stored at −20° C. until use. The concentration of the tested compounds in the plasma samples were determined using the human ELISA against a calibration curve which was made of the stock solution of the tested compound itself. The concentration in the samples was expressed in nmol/L and the kinetic parameters were calculated with the noncompartment model of WinNonlin.

Figure 13:
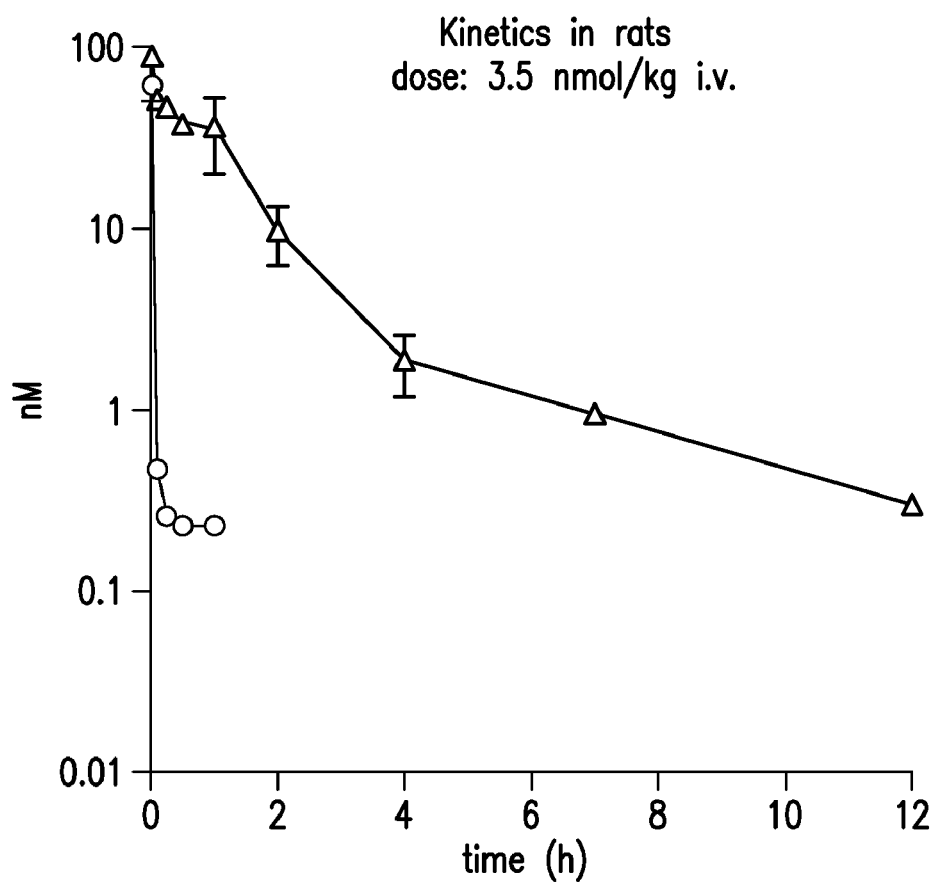

Conclusion: As can be seen in FIG. 13 and Table 3 the pharmacokinetic properties of pentasaccharide-insulin conjugate 6 were strongly improved compared to those of the parent recH insulin.

TABLE 3

Pharmacokinetic parameters after i.v. administration of compound 6 or recH insulin (3.5 nmol/kg) in rat. Experiment performed in n = 3/treatment.

| | Pentasaccharide-insulin conjugate 6 Mean ± s.e.m. | recH insulin Mean ± s.e.m. |
|---|---|---|
| T½ eli (h) | 2.8 ± 0.1 | 0.033 ± 0.001 |
| AUCinf (h · nmol/L) | 72.5 ± 6.4 | 4.6 ± 0.8 |
| Vss (L/kg) | 0.11 ± 0.01 | 0.012 ± 0.002 |
| Cl (L/h/kg) | 0.049 ± 0.004 | 0.80 ± 0.12 |
| MRT (h) | 2.1 ± 0.1 | 0.014 ± 0.1 |

Determination of Pharmacokinetics after Labeling with [125]I

Pentasaccharide conjugates 24, 28, 29, 31, 32, 39 and 41 were labeled with $^{125}$I using the lactoperoxidase method, according to Machalonis et al. (*Biochem J.* 1969, 113: 299-305). After labeling, the conjugate was purified by gel filtration on Sephadex G25 and anion exchanger HiTrap Q10. Kinetic experiments were repeated as described for compound 6 but using $^{125}$I-labeled conjugates instead. In order to prevent accumulation of [125]I− in the thyroid, rats were orally treated with 10 mg/kg potassium iodide prior to administration of compound.

The correct determination of the fate of $^{125}$I-labeled conjugates might be affected aversely by metabolic intracellular endogenous dehalogenation to give free $^{125}$I$^-$ in circulation. Since the free $^{125}$I$^-$ itself showed an elimination half-life of 3.2 h in rats (control, data not shown), the measured overall half-life of $^{125}$I labeled compounds with a relatively short half-life might be prolonged and the experimentally determined half-life of compounds with a relatively long half life may be shorter. Indeed, the observed elimination half-lives of conjugates 31, 32 and 39 demonstrate in a qualitative manner that conjugation of the peptides to a carrier pentasaccharide leads to prolonged residence times.

Adaptation of the above described method by measuring the radioactivity in pellet (0.1 mL) after precipitation with a 40 times higher volume of TCA (10% final concentration) yielded pharmacokinetic parameters of compounds 24, 28, 29 and 41 which were corrected for competing endogenous $^{125}$I-dehalogenation.

Pharmacokinetics of Insulin-Pentasaccharide Conjugates 24, 28 and 29 Compared to recH Insulin

TABLE 4

Pharmacokinetic parameters after i.v. administration of insulin conjugates 24, 28 and 29. Experiment performed in n = 3/treatment. For comparison recH insulin was tested in n = 1 (doses expressed in cpm were normalized).

|  | Compound 24 Mean ± s.e.m. | Compound 28 Mean ± s.e.m. | Compound 29 Mean ± s.e.m. | recH insulin value (n = 1) |
|---|---|---|---|---|
| Correlation | −1.00 | −1.00 | −1.00 | −1.00 |
| T½ eli | 3.0 ± 0.2 | 3.9 ± 0.1 | 5.5 ± 0.3 | 0.74 |
| AUCinf (h · cpm/0.1 mL) | 30447 ± 4034 | 13756 ± 590 | 14397 ± 517 | 481 |
| Vss (L/kg) | 0.192 ± 0.022 | 0.428 ± 0.028 | 0.570 ± 0.018 | 2.225 |
| Cl (L/h/kg) | 0.068 ± 0.009 | 0.146 ± 0.007 | 0.139 ± 0.05 | 4.16 |
| MRT (h) | 2.8 ± 0.1 | 2.9 ± 0.1 | 4.1 ± 0.2 | 0.5 |

Figure 14:
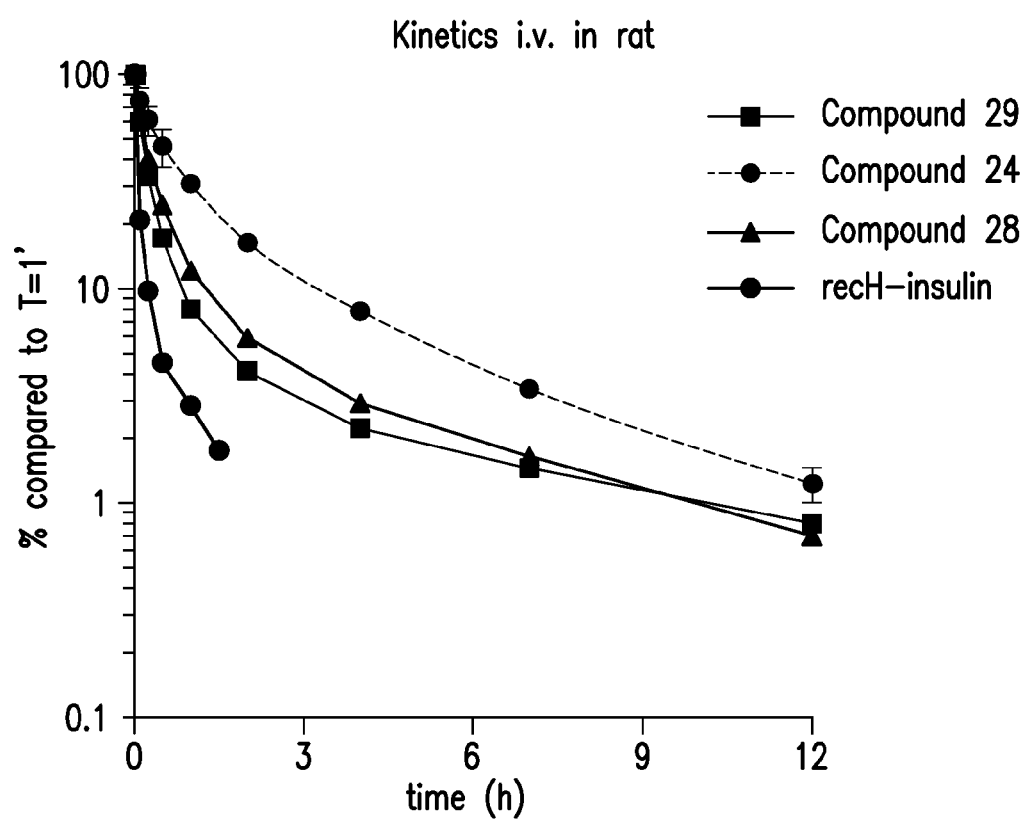

Conclusion: The pharmacokinetic properties of insulin-pentasaccharide conjugate 24 as determined by the $^{125}$I-labeling method (FIG. 14, Table 4) were in agreement with those obtained with a similar insulin-pentasaccharide conjugate (compound 6) determined by the ELISA method (FIG. 13, Table 3). The differences in kinetic parameters for recH insulin as determined by two analytical methods can be explained by differences in curve extrapolation (to calculate Vss and Cl) due to the fast disappearance of label from the circulation during the first 15 min.

Furthermore, the observed differences in AUC, Cl and Vss of the insulin pentasaccharide conjugates 24, 28, 29 (FIG. 14, Table 4) clearly demonstrate that the pharmacokinetic properties of the conjugates can be tuned by using alternative carrier pentasaccharides with different binding affinity for ATIII (which is in agreement with the findings of the BIA study, see FIG. 6 and Table 2).

Pharmacokinetics of Pentasaccharide Conjugates 31 and 32

TABLE 5

Pharmacokinetic parameters after i.v. administration of the two conjugates 31 and 32. Experiment performed in n = 3/treatment. (Data not corrected for dehalogenation).

|  | Compound 31 Mean ± s.e.m. | Compound 32 Mean ± s.e.m. |
|---|---|---|
| Correlation | −1.00 | −1.00 |
| T½ eli (h) | 7.1 ± 0.3 | 9.4 ± 0.6 |
| Vss (ml/rat) | 66.7 ± 2.3 | 52.5 ± 2.6 |
| Cl (ml/h/rat) | 7.9 ± 0.1 | 4.2 ± 0.3 |
| MRT (h) | 8.4 ± 0.2 | 12.6 ± 0.7 |

Figure 15:
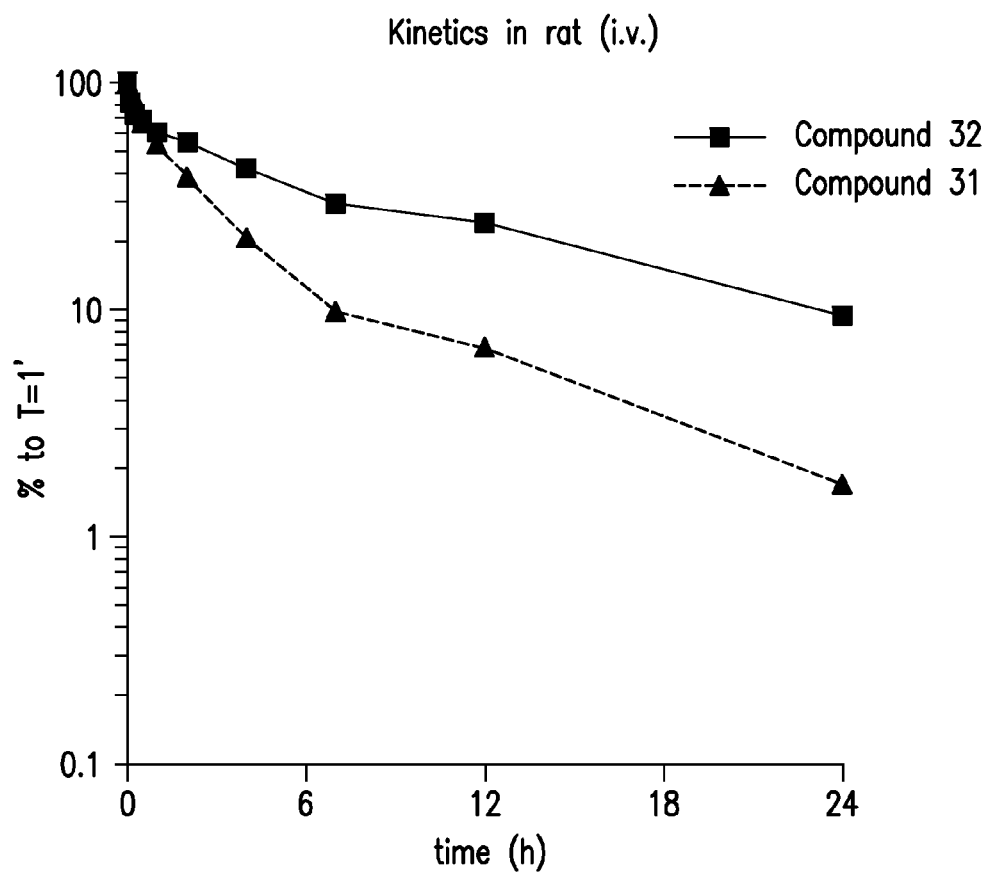

Conclusion: The half-life of free ganirelix (T½ 1.4 h in rat, i.v., Chan et al. *Drug. Metab. Dispos* 1991, 19, 858) is significantly extended when conjugated to a carrier pentasaccharide (FIG. 15, Table 5). Comparison of the pharmacokinetics of compound 31 to that of 32 shows that an improvement in Vss, Cl and T½ elimination is obtained by using a pentasaccharide with a higher affinity for ATIII. These data in combination with the findings of the BIA study (see FIG. 8) indicate that the pharmacokinetic properties of the conjugates can be tuned by using alternative carrier pentasaccharides with different binding affinity for ATIII.

Pharmacokinetics of Pentasaccharide Conjugate 39 and ADM(27-52)

TABLE 6

Pharmacokinetic parameters after i.v. administration of ADM(27-52) and compound 39. Experiment performed in n = 3/treatment. (data not corrected for dehalogenation).

|  | ADM(27-52) Mean ± s.e.m. | Compound 39 Mean ± s.e.m. |
|---|---|---|
| Correlation | −1.00 | −1.00 |
| T½ eli (h) | 4.9 ± 0.1 | 11.1 ± 0.2 |
| Vss (ml/rat) | 556 ± 48 | 80 ± 3.3 |
| Cl (ml/h/) | 112 ± 9 | 5.0 ± 0.1 |
| MRT (h) | 5.0 ± 0.1 | 14.5 ± 0.3 |

Figure 16:
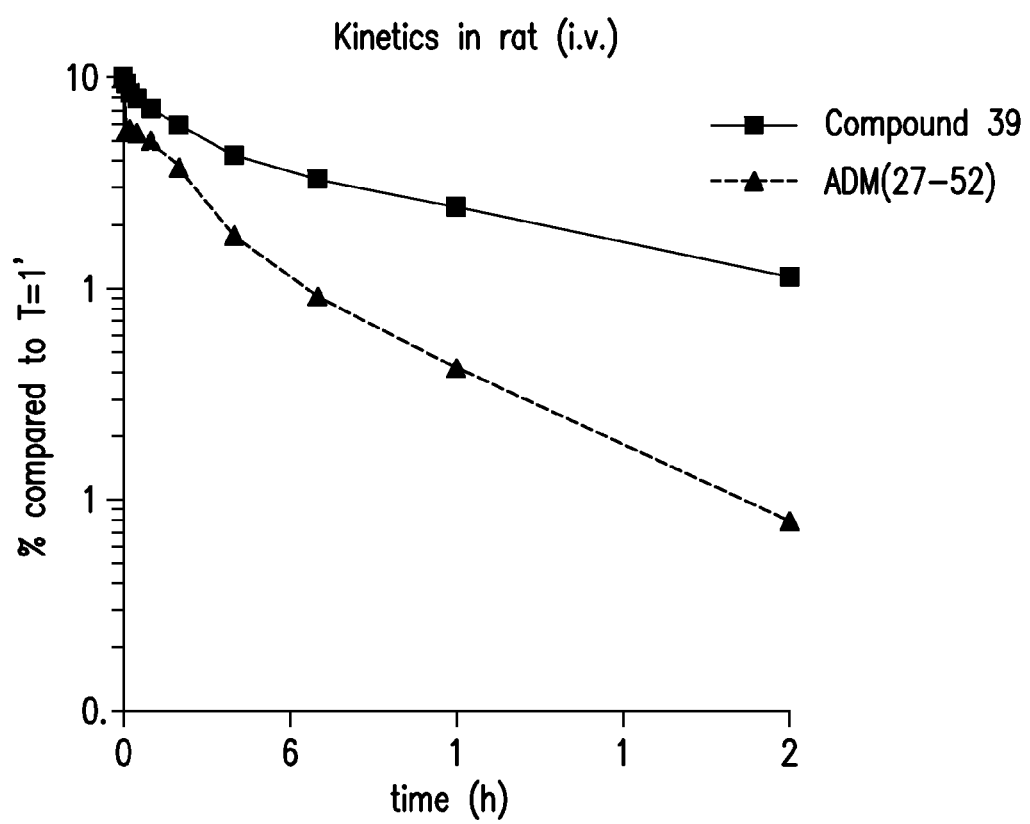

Conclusion: The pharmacokinetic properties of ADM(27-52) were improved by conjugation to an ATIII binding carrier pentasaccharide (compound 39, FIG. 16, Table 6). The T½ of ADM(27-52) per se may have been overestimated since data have not been corrected for dehalogenation. Moreover, the half-life of free adrenomedullin is only 22 min in human (Meeran et al. *J. Clin. Endocrin. Met.* 1997, 82, 95-100). These and earlier observations in the BIA study (FIG. 9) support the conclusion that an improvement of pharmacokinetic properties of a (poly)peptide can be achieved by conversion into a (carrier) conjugate with specific binding affinity to circulating ATIII.

Pharmacokinetics of Pentasaccharide Conjugate 41 Compared with [D-Ala$^8$]-GLP-1(7-36)

TABLE 7

Pharmacokinetic parameters after i.v. administration of GLP-1 and compound 41 Experiment performed in n = 3/treatment (data expressed in cpm were normalized)

|  | [D-Ala$^8$]-GLP-1(7-36) Mean ± s.e.m. | Compound 41 Mean ± s.e.m. |
|---|---|---|
| Correlation | −0.98 | −0.99 |
| T½ eli (h) | 2.0 ± 0.4 | 9.8 ± 0.4 |
| AUCinf (h · cpm/0.1 mL) | 1154 ± 59 | 108658 ± 4858 |
| Vss (ml/kg rat) | 2696 ± 456 | 205 ± 13 |
| Cl (ml/h/kg) | 1732 ± 86 | 18 ± 0.8 |
| MRT (h) | 1.6 ± 0.1 | 11.2 ± 0.3 |

Figure 17:
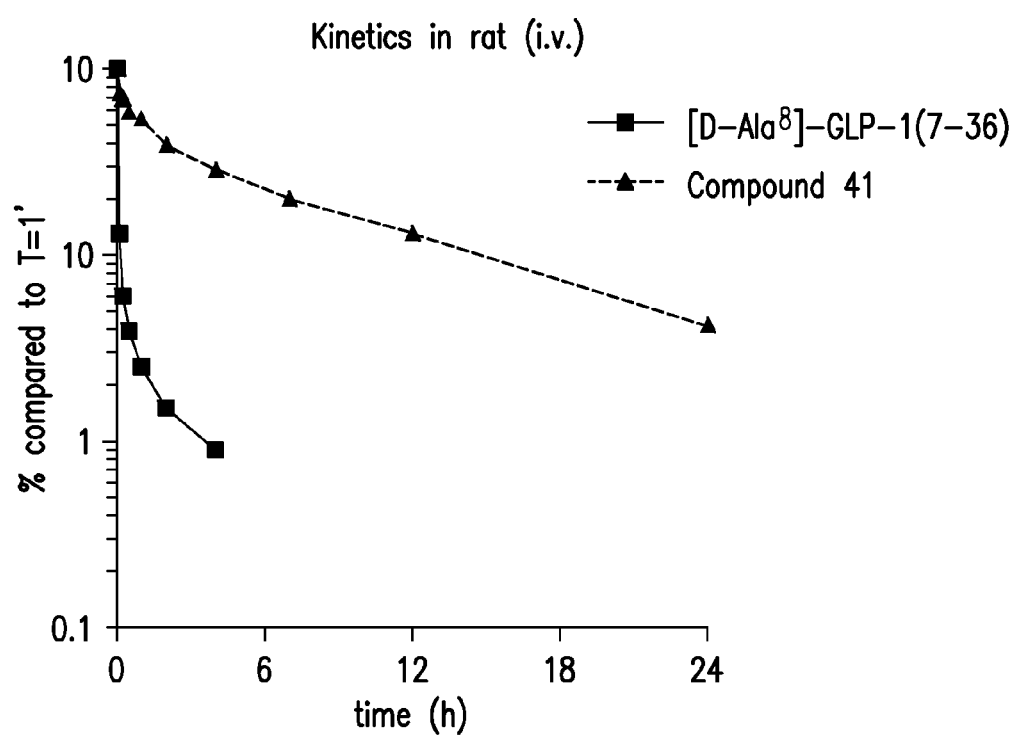

Conclusion: The pharmacokinetic properties of [D-Ala$^8$]-GLP1(7-36) were improved by conjugation to an ATIII binding carrier pentasaccharide (compound 41, FIG. 17, Table 7). The Cl of compound 41 was decreased ~100 fold and Vss 13 fold, resulting in a ~100 fold increase in AUC (exposure) compared to the non-conjugated peptide. Combined with the BIA data (FIG. 10) these observations support the conclusion that an improvement of pharmacokinetic properties of a (poly)peptide can be achieved by conversion into an ATIII binding conjugate.

Determination of (Poly)Peptide-Pentasaccharide-ATIII Complex in Rat Plasma

To ensure that (poly)peptide pentasaccharide conjugates bind to Antithrombin III in vivo, a sandwich-type ELISA employing an anti-insulin Mab as capture and a HRP-conjugated anti-ATIII antibodies as detector was carried out on plasma samples from the pharmacokinetic experiment of compound 6. Obviously, only intact pentasaccharide-insulin-ATIII complex can be detected in this type of assay in which recH insulin was used as a negative control).

Figure 18A:
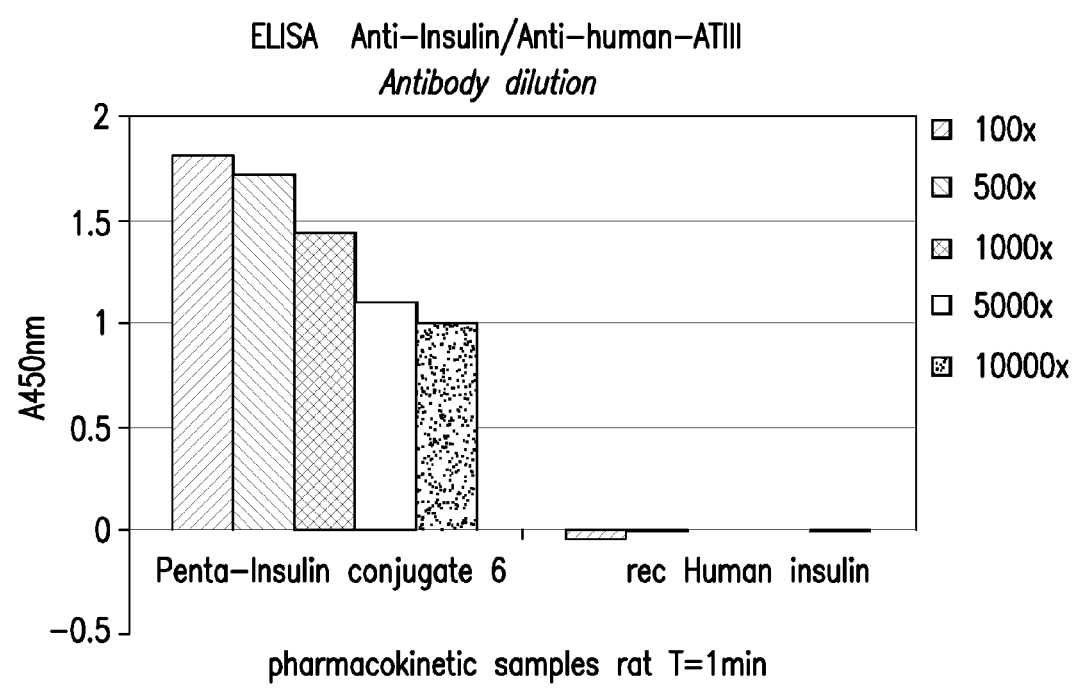
Figure 18B:
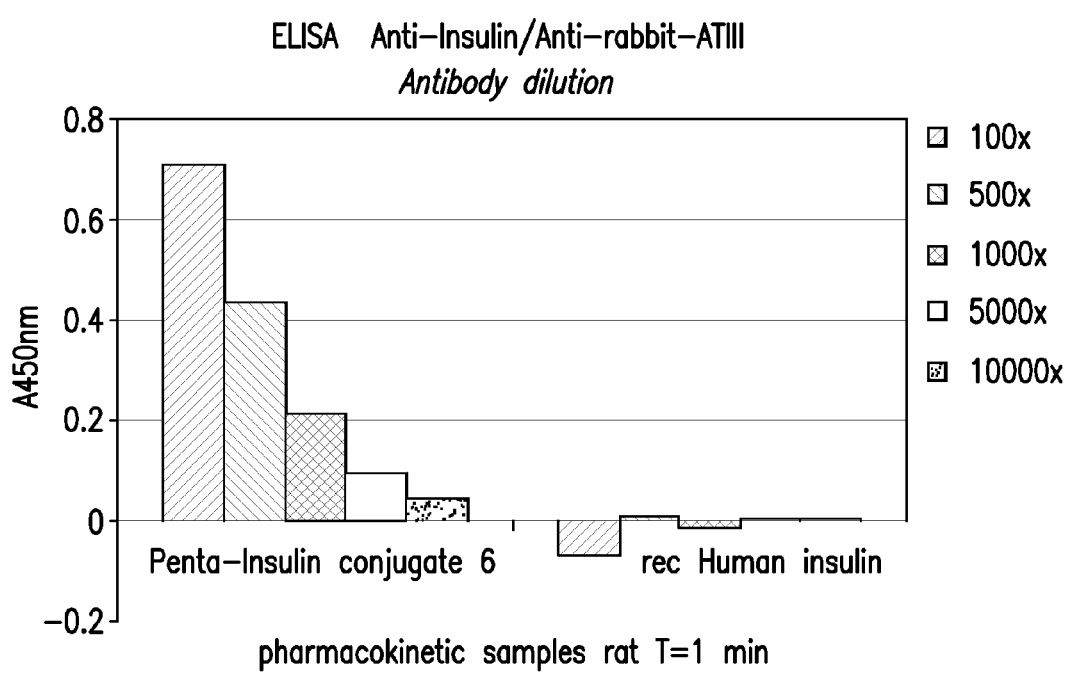

From the plasma sample obtained 1 min after i.v. administration of 3.5 nmol/kg compound 6 or recH insulin in rat, the binding of pentasaccharide-insulin conjugate 6 and recH insulin to rat ATIII was determined. The results are shown in FIG. 18.

Conclusion: Pentasaccharide-insulin conjugate 6 is bound to ATIII, in contrast with recH-insulin which cannot form a complex with ATIII. Although the anti-rabbit ATIII antibody was less sensitive, both ATIII antibodies were able to detect the pentasaccharide-insulin conjugate 6-ATIII complex. These results demonstrate that compound 6 is bound to ATIII in circulation and that the prolonged half-life of ATIII-binding pentasaccharides is the result of this complexation Therefore, it can be concluded that the improvement of the pharmacokinetic properties of (poly)peptide-pentasaccharide conjugates (such as compound 6) compared to those of the original non-conjugated (poly)peptide can be ascribed to specific binding of the conjugate to ATIII.

Glucose Suppression Test In Vivo in Rats

The biological activities of insulin and the insulin conjugates were tested in a rat model by measuring the glucose depression levels. The animals were fasted overnight (16 hours) prior to the experiment. In the morning blood was sampled from all the rats by cutting a little piece of the tail, after which the blood was dropped on a test strip and the glucose levels were measured with an ACCU-Check Sensor blood glucose monitor (Roche Diagnostics). The pentasaccharide-insulin conjugate 6 and insulin were i.v. administered in the tail vein after pre-heating of the rats in a heating box at 39° C. during 10 min. The applied doses were 7 nmol/kg for pentasaccharide-insulin conjugate 6 and 3.5 nmol/kg for recH-insulin. At various time intervals blood samples were taken by removing the crusted blood, after which the glucose content was determined immediately as described.

Pharmacodynamics of Pentasaccharide Insulin Conjugate 6

Figure 19:
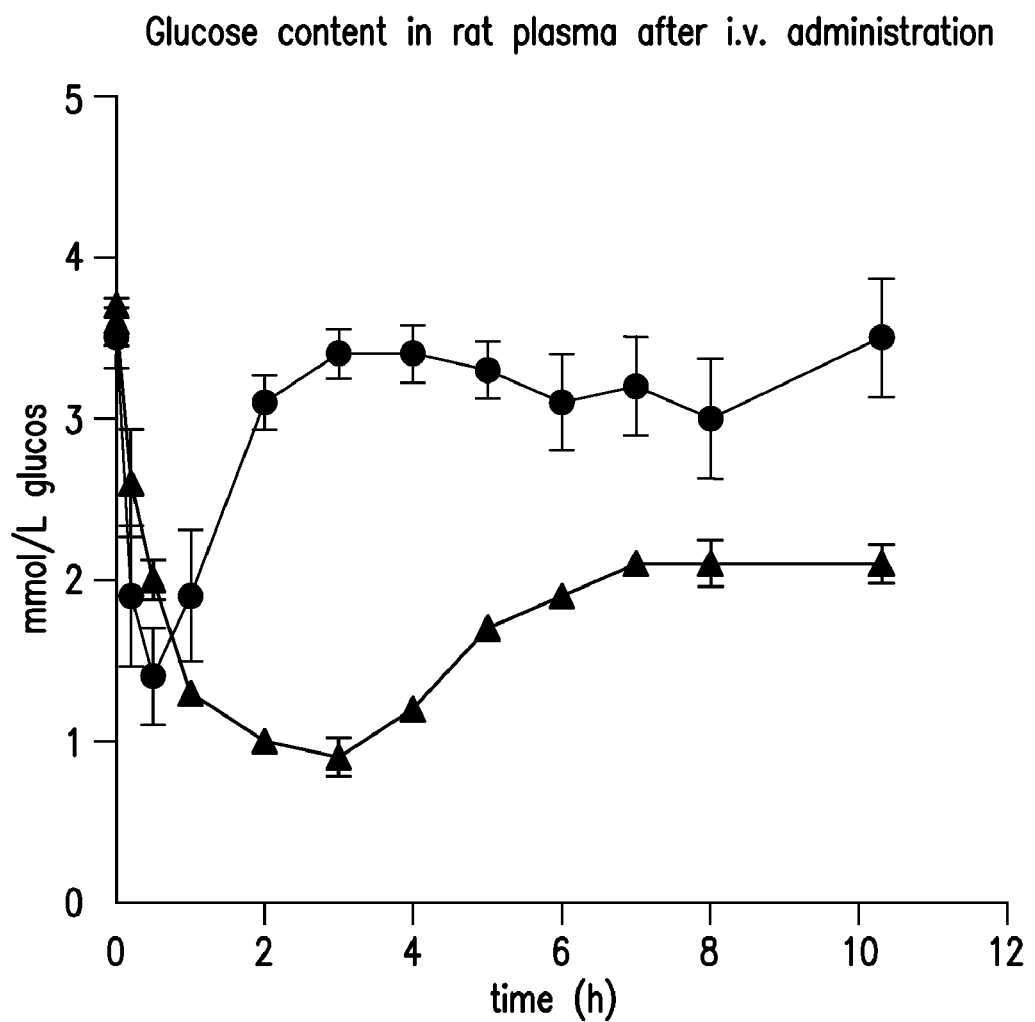

The improved pharmacokinetic properties of pentasaccharide-insulin conjugate 6 compared to those of recH-insulin are confirmed by the prolonged glucose suppression levels after i.v. administration (see FIG. 19).

In the experiments performed with compounds 24, 25, 26, 27 and insulin detemir (control), the rats were starved just prior to administration of compound (to warrant consistant glucose levels in control group).

Figure 20:
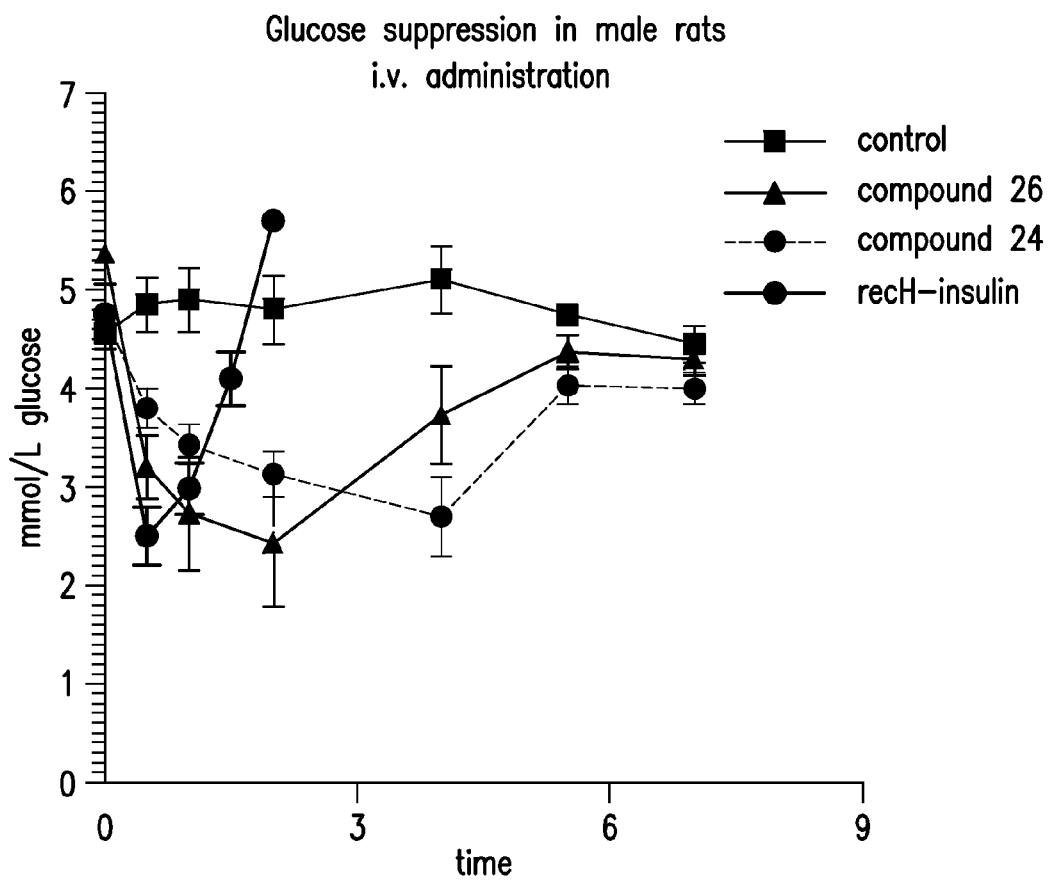

Comparison of the B29-insulin conjugate 24 with B29-insulin conjugate 26 (FIG. 20), and B1-insulin conjugate 25 with B1-insulin conjugate 27 (FIG. 21), reveals that similar prolonged glucose suppression activities are obtained irrespective of spacer length.

Surprisingly, it was found that the onset of action of all insulin-conjugates tested was slower than that of recH insulin or insulin detemir (i.v. administration) and that the exposure was enhanced by the longer duration of action.

Figure 21:
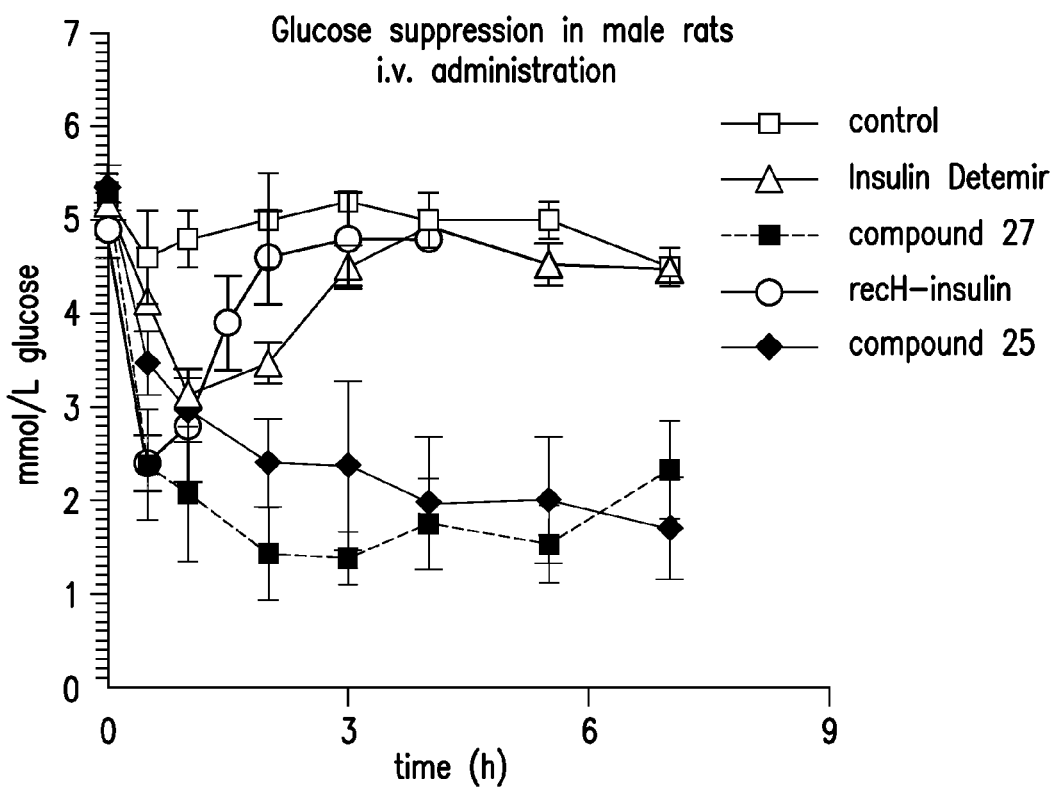
Figure 22:
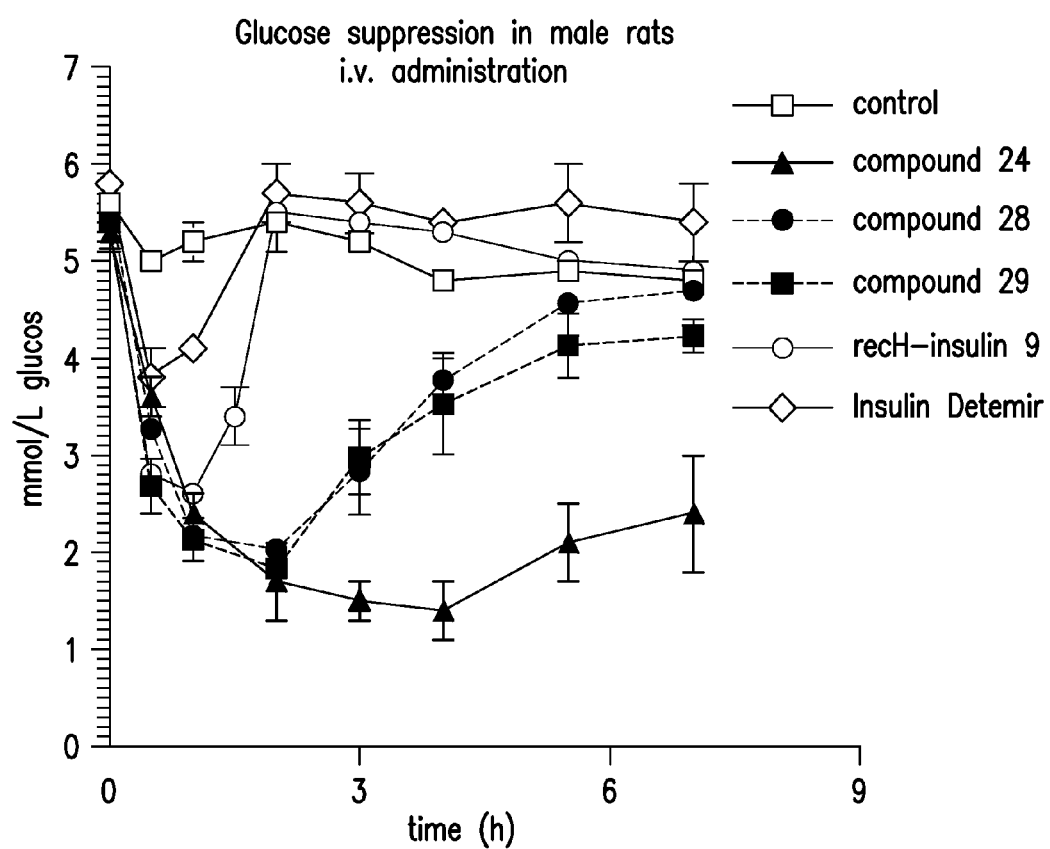

Direct comparison of B29-insulin conjugates 24, 28 and 29 within one experiment at the dose of 24 nmol/kg substantiates the difference in duration of action of their blood glucose lowering activities (see FIG. 22). Thus, suppression of glucose levels with compound 24 lasted beyond 7 h, while conjugates 28 and 29 were no longer active than 5.5 h after i.v. administration. The pharmacodynamic differences correspond with the earlier mentioned pharmacokinetic differences in distribution volume and clearance of compound 24 compared to compound 28 and 29, respectively. Finally, insulin detemir was tested as a comparative example showing less pronounced and less prolonged activity at doses of 24 and 48 nmol/kg (FIG. 21, 22).

What is claimed is:

1. A conjugate of insulin and an oligosaccharide, wherein the insulin is conjugated to at least one oligosaccharide-spacer residue having the structure (II)

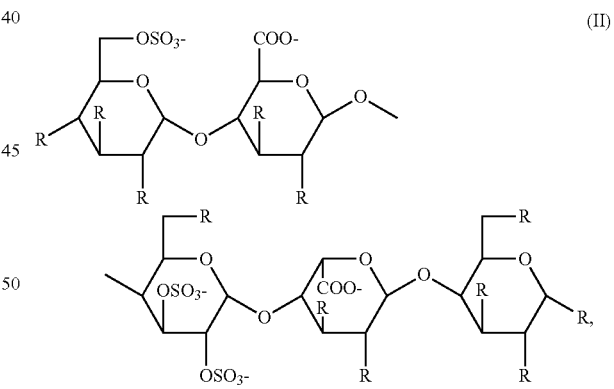

wherein R is independently OSO$_3^-$ or (1-8C)alkoxy, or a pharmacologically inactive flexible linking residue, the charge of OSO$_3^-$ and COO$^-$ being compensated by positively charged counter ions, and wherein one pharmacologically inactive flexible linking residue is present, or a pharmaceutically acceptable salt thereof.

2. The conjugate of claim 1, having a circulating plasma level of ≦50 nM.

3. The conjugate of claim 1, wherein the oligosaccharide per se has an anticoagulant activity which is of subtherapeutic level when compared to the pharmacological activity of the insulin per se.

4. The conjugate of claim 1, wherein the oligosaccharide residue has the structure (III)

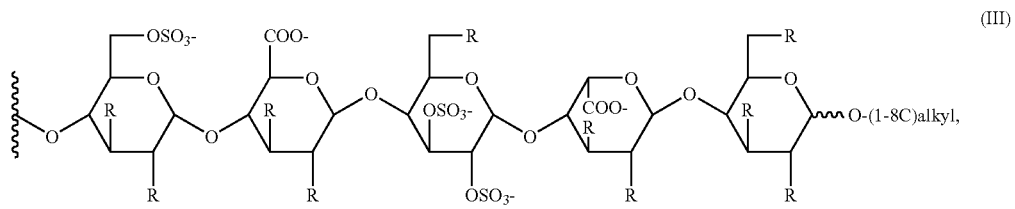

(III)

wherein R is independently OSO$_3^-$ or (1-8C)alkoxy, the charge of OSO$_3^-$ and COO$^-$ being compensated by positively charged counterions.

5. The conjugate of claim 4, wherein the oligosaccharide residue has the structure (IV)

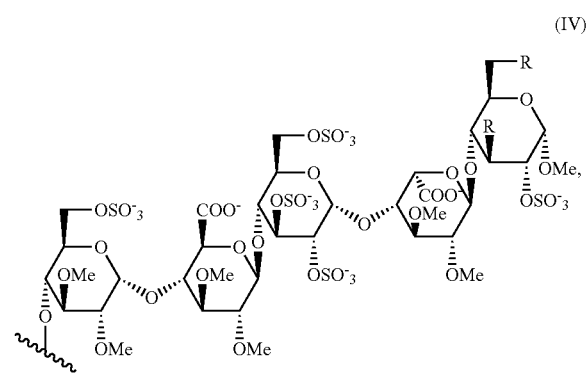

(IV)

wherein R is independently OCH$_3$ or OSO$_3^-$.

6. The conjugate of claim 5, wherein both R groups in (IV) are OSO$_3^-$.

7. The conjugate of claim 1, wherein the insulin is mono-substituted with an oligosaccharide-spacer residue.

8. The conjugate of claim 1, wherein the pharmacologically inactive flexible linking residue has a length of 10-50 atoms.

9. The conjugate of claim 1, wherein the pharmacologically inactive flexible linking residue comprises at least one —(CH$_2$CH$_2$O)— element.

10. The conjugate of claim 1, selected from the structures

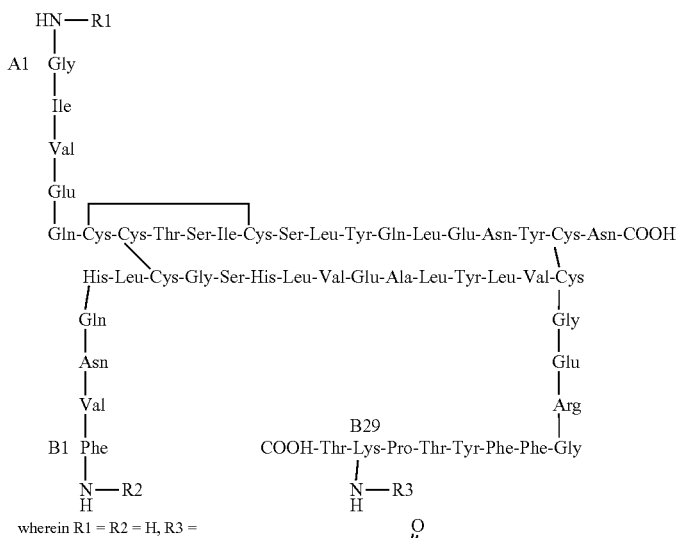

wherein R1 = R2 = H, R3 =

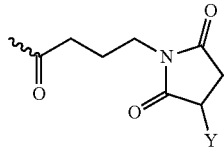

or wherein R1 = R3 = H, R2 =

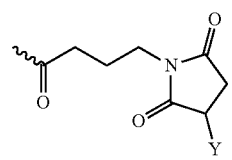

and wherein Y is selected from structures A, B, C and D
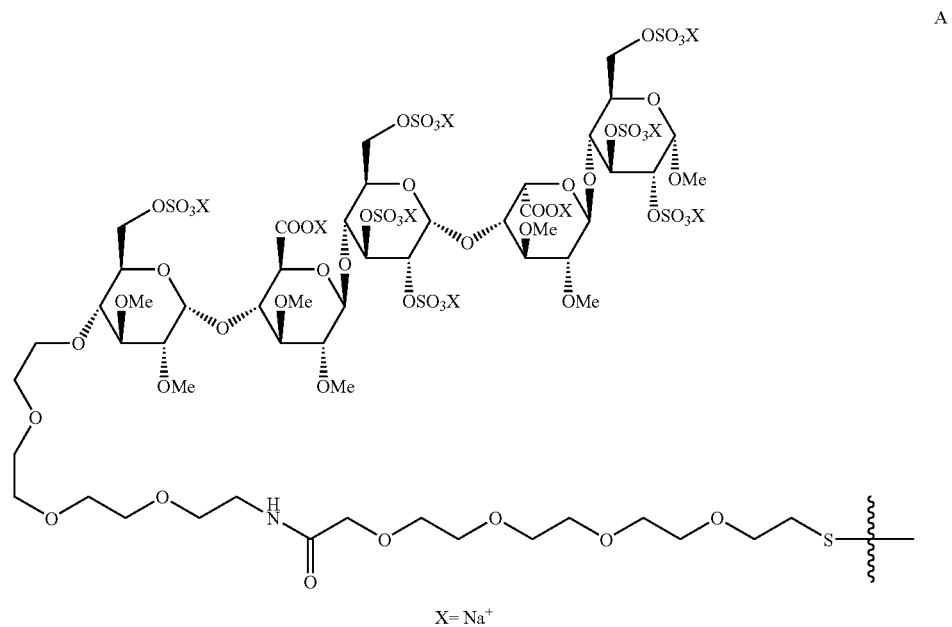
A
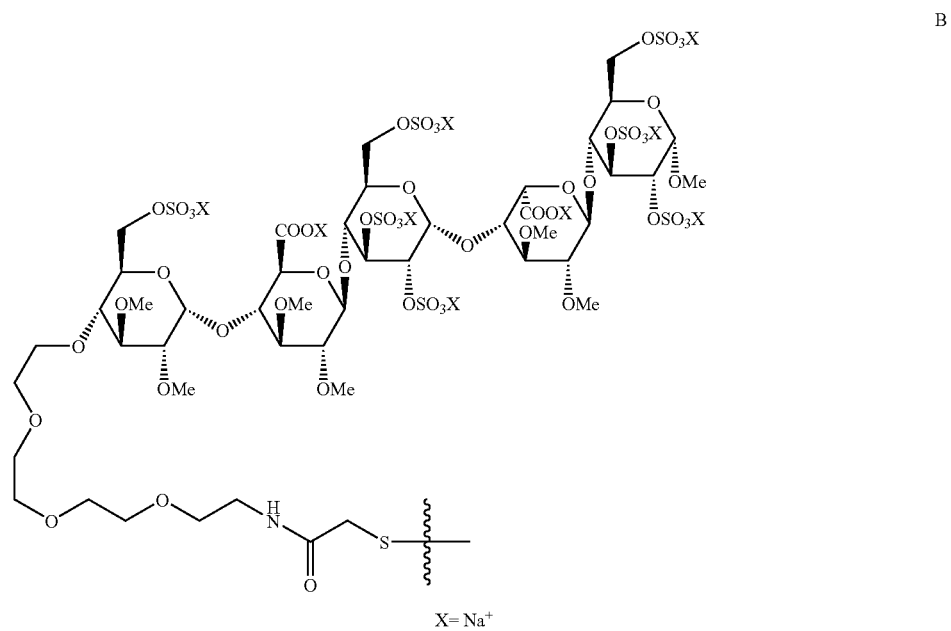
B -continued
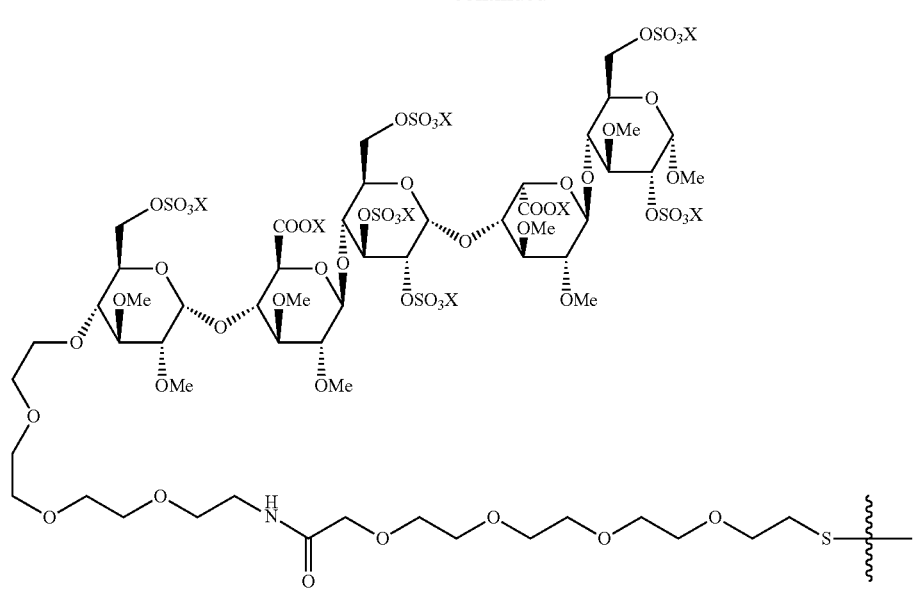
C
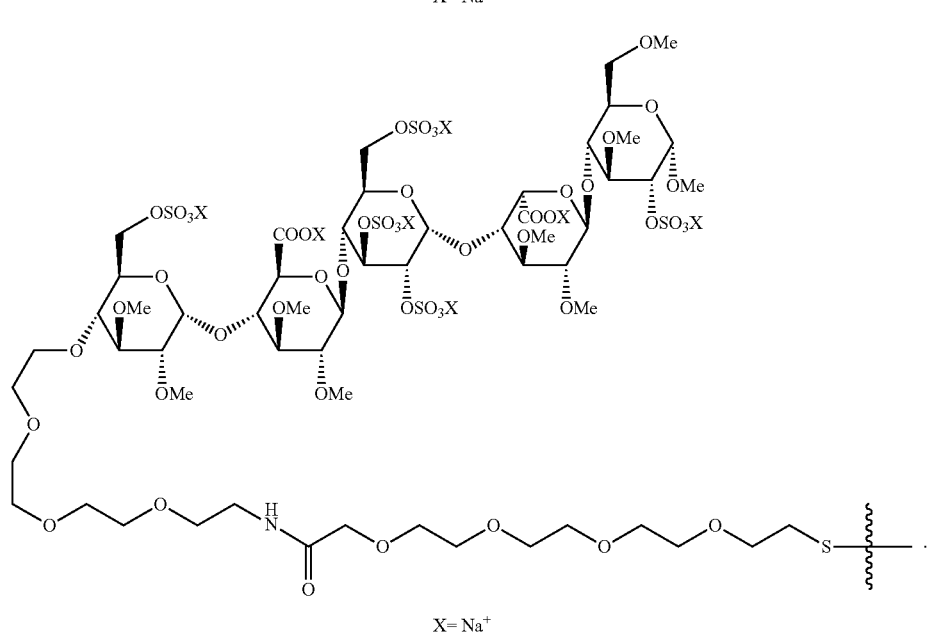
D
11. The conjugate of claim 10, wherein Y is selected from structures A and B.
12. A pharmaceutical composition comprising the conjugate of claim 1 and pharmaceutically suitable auxiliaries.
13. The conjugate of claim 1 for use as an anti-diabetic agent.
* * * * *